(12) United States Patent
Sheppeck et al.

(10) Patent No.: US 8,198,311 B2
(45) Date of Patent: Jun. 12, 2012

(54) MODULATORS OF GLUCOCORTICOID RECEPTOR, AP-1, AND/OR NF-κB ACTIVITY AND USE THEREOF

(75) Inventors: James E. Sheppeck, Newtown, PA (US); John L. Gilmore, Yardley, PA (US); T. G. Murali Dhar, Newtown, PA (US); Hai-Yun Xiao, Belle Mead, NJ (US); Jianmin Wang, Blacksburg, VA (US); Bingwei Vera Yang, Belle Mead, NJ (US); Lidia M. Doweyko, Long Valley, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 55 days.

(21) Appl. No.: 12/513,232

(22) PCT Filed: Oct. 31, 2007

(86) PCT No.: PCT/US2007/083085
§ 371 (c)(1),
(2), (4) Date: Jul. 30, 2009

(87) PCT Pub. No.: WO2008/057857
PCT Pub. Date: May 15, 2008

(65) Prior Publication Data
US 2010/0075961 A1    Mar. 25, 2010

Related U.S. Application Data

(60) Provisional application No. 60/855,953, filed on Nov. 1, 2006.

(51) Int. Cl.
*A61K 31/416* (2006.01)
*C07D 231/56* (2006.01)
(52) U.S. Cl. .................................. 514/406; 548/362.5
(58) Field of Classification Search .................. None
See application file for complete search history.

(56) References Cited

FOREIGN PATENT DOCUMENTS

| WO | WO 02/079143 | * 10/2002 |
|---|---|---|
| WO | WO 2004/019935 | 3/2004 |
| WO | WO 2005/056550 | * 6/2005 |
| WO | WO 2005/084672 | 9/2005 |
| WO | WO 2005/095383 | * 10/2005 |
| WO | WO 2005/103037 | 11/2005 |
| WO | WO 2006/135826 | * 12/2006 |
| WO | WO 2006/138373 | 12/2006 |
| WO | WO 2007/046747 | 4/2007 |
| WO | WO2008/021926 | 2/2008 |
| WO | WO2008/057856 | 5/2008 |
| WO | WO2008/057859 | 5/2008 |
| WO | WO2008/057862 | 5/2008 |
| WO | WO 2008/070507 | 6/2008 |
| WO | WO 2008/079073 | 7/2008 |

OTHER PUBLICATIONS

Morissette et al. "High-throughput crystallization: polymorphs, salts, co-crystals and solvates of pharmaceutical solids." Advanced Drug Delivery Reviews 2004, 56, 275-300.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta, Sudha R. "Crystalline Solids." Advanced Drug Delivery Reviews 48(2001): 3-26.*
Baldwin, Jr., A.S., "The transcription factor NF-κb and human disease", The Journal of Clinical Investigation, vol. 107, No. 1, pp. 3-6 (2001).
Burke, J.R., "Targeting IκB kinase for the treatment of inflammatory and other disorders", Current Opinion in Drug Discovery & Development, vol. 6, No. 5, pp. 720-728 (2003).
Caldenhoven, E. et al., "Negative Cross-Talk between RelA and the Glucocorticoid Receptor: A Possible Mechanism for the Antiinflammatory Action of Glucocorticoids", Molecular Endocrinology, vol. 9, No. 4, pp. 401-412 (1995).
Chakravarti, D. et al., "Role of CBP/P300 in nuclear receptor signaling", Nature, vol. 383, pp. 99-103 (1996).
Diamond, M.I. et al., "Transcription Factor Interactions: Selectors of Positive or Negative Regulation from a Single DNA Element", Science, vol. 249, pp. 1266-1272 (1990).
Firestein, G.S. et al., "Signal Transduction and Transcription Factors in Rheumatic Disease", Arthritis & Rheumatism, vol. 42, No. 4, pp. 609-621 (1999).
Jonat, C. et al., "Antitumor Promotion and Antiinflammation: Down-Modulation of AP-1 (Fos/Jun) Activity by Glucocorticoid Hormone", Cell, vol. 62, pp. 1189-1204 (1990).
Kamei, Y. et al., "A CBP Integrator Complex Mediates Transcriptional Activation and AP-1 Inhibition by Nuclear Receptors", Cell, vol. 85, pp. 403-414 (1996).

(Continued)

*Primary Examiner* — Rebecca Anderson
*Assistant Examiner* — Alicia L Otton
(74) *Attorney, Agent, or Firm* — Burton Rodney

(57) ABSTRACT

Novel non-steroidal compounds are provided which are useful in treating diseases associated with modulation of the glucocorticoid receptor, AP-1, and/or NF-κB activity including inflammatory and immune diseases, obesity and diabetes having the structure of formula (I), its enantiomers, diastereomers, or a pharmaceutically acceptable salt, or hydrate, thereof, wherein X is (Ia); or X is (Ib); or X is (Ic); (Id) is heterocycle or heteroaryl; E is —N—, —$NR_1$—, —O—, —S—, —$SO_2$— or —$CR_2$—; F is —N—, —$NR_{1a}$—, —O—, —S—, —$SO_2$— or —$CR_{2a}$—; G is N, —$NR_{1b}$—, —O—, —S—, —$SO_2$— or —$CR_{2b}$—, provided that the E-F-G containing heterocyclic ring formed does not contain a S—S or S—O bond, and at least one of E, F and G is a heteroatom; J, $J_a$, M, $M_a$, Q, $R_x$, $R_y$, $R_1$, $R_{1a}$, $R_{1b}$, $R_2$, $R_{2a}$, $R_{2b}$, and $R_3$ to $R_{21}$, Z, $Z_a$, $Z_b$, and $Z_c$ are as defined above.

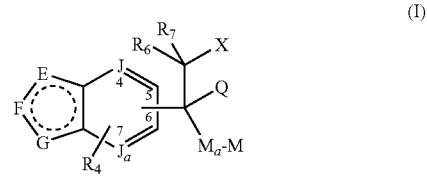

(I)

9 Claims, No Drawings

OTHER PUBLICATIONS

Manning, A.M., et al., "Targeting JNK for Therapeutic Benefit: from Junk to Gold?", Nature, vol. 2, pp. 554-565 (2003).

Miesfeld, R. et al., "Characterization of a steroid hormone receptor gene and mRNA in wild-type and mutant cells", Nature, vol. 312, pp. 779-781 (1984).

Peltz, G., "Transcription factors in immune-mediated disease", Current Opinion in Biotechnology, vol. 8, pp. 467-473 (1997).

Reichardt, H.M. et al., "DNA Binding of the Glucocorticoid Receptor is Not Essential for Survival", Cell, vol. 93, pp. 531-541 (1998).

Reichardt, H.M. et al., "Repression of inflammatory responses in the absence of DNA binding by the glucocorticoid receptor", The EMBO Journal, vol. 20, No. 24, pp. 7168-7173 (2001).

Schäcke, H. et al., "Dissociated non-steroidal glucocorticoid receptor modulators: an update on new compounds", Expert Opin, Ther. Patents, vol. 18, No. 3, pp. 339-352 (2008).

Weinberger, C. et al., "Domain structure of human glucocorticoid receptor and its relationship to the v-erb-A oncogene product", Nature, vol. 318, pp. 670-672 (1985).

Weinberger, C. et al., "Identification of Human Glucocorticoid Receptor Complementary DNA Clones by Epitope Selection", Science, vol. 228, pp. 740-742 (1985).

Yang-Yen, H.-F. et al., "Transcriptional Interference between c-Jun and the Glucocorticoid Receptor: Mutual Inhibition of DNA Binding Due to Direct Protein-Protein Interaction", Cell, vol. 62, pp. 1205-1215 (1990).

* cited by examiner

MODULATORS OF GLUCOCORTICOID RECEPTOR, AP-1, AND/OR NF-κB ACTIVITY AND USE THEREOF

FIELD OF THE INVENTION

The present invention relates to new non-steroidal compounds which are effective modulators of the glucocorticoid receptor, and/or AP-1, and/or NF-κB activity and thus are useful in treating diseases such as inflammatory or immune associated diseases, and to a method for using such compounds to treat these and related diseases.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A. S., *Journal of Clin. Investigation*, 107:3 (2001); Firestein, G. S., and Manning, A. M., *Arthritis and Rheumatism*, 42:609 (1999); and Peltz, G., *Curr. Opin. in Biotech.*, 8:467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/c-jun). Compounds which inhibit JNK have been shown to be efficacious in animal models of inflammatory disease. See Manning, A. M. and Davis, R. J., *Nature Rev. Drug Disc.*, 2:554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK has been shown to be efficacious in animal models of inflammatory disease. See Burke, J. R., *Curr. Opin. Drug Discov. Devel.*, 6(5):720-728 (September 2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger et al., *Science*, 228:740-742 (1985); Weinberger et al., *Nature*, 318:670-672 (1986) and for results in rats see Miesfeld, R., *Nature*, 312:779-781 (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C. et al., *Cell*, 62:1189 (1990); Yang-Yen, H. F. et al., *Cell*, 62:1205 (1990); Diamond, M. I. et al., *Science* 249:1266 (1990); and Caldenhoven, E. et al., *Mol. Endocrinol.*, 9:401 (1995). Other mechanisms such as sequestration of co-activators by GR have also been proposed. See Kamei, Y. et al., *Cell*, 85:403 (1996); and Chakravarti, D. et al., *Nature*, 383:99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Reichardt, H. M. et al., *Cell*, 93:531 (1998) and Reichardt, H. M., *EMBO J.*, 20:7168 (2001).

Compounds that modulate AP-1 and NF-κB activity would be useful in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents. However their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

DESCRIPTION OF THE INVENTION

The present invention relates to new non-steroidal compounds (such as compounds of formulae I and IA) which are effective modulators of the glucocorticoid receptor, and/or AP-1, and/or NF-κB activity and thus are useful in treating diseases such as inflammatory or immune associated diseases, and/or obesity and diabetes, and to a method for using such compounds to treat these and related diseases.

In accordance with one aspect of the invention, compounds are provided having the structure of formula I,

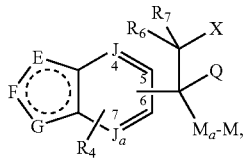

its enantiomers, diastereomers, tautomers, a prodrug ester thereof, or a pharmaceutically-acceptable salt, or hydrate, thereof,
wherein the side chain group

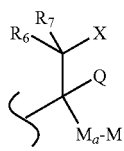

is attached to the bicyclic ring

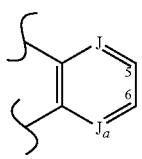

at the 5- or 6-position;
(A) X is

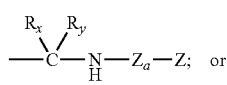

(B) X is

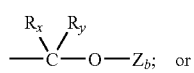

(C) X is

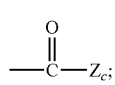

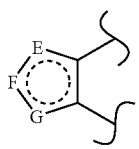

is heterocyclo or heteroaryl;

E is selected from —N—, —$NR_1$—, —O—, —C(=O)—, —S—, —$SO_2$—, and —$CR_2$—;

F is selected from —N—, —$NR_{1a}$—, —O—, —C(=O)—, —S—, $SO_2$—, and —$CR_{2a}$—;

G is selected from N, —$NR_{1b}$—, —O—, —C(=O)—, —S—, $SO_2$—, and —$CR_{2b}$—, provided that the E-F-G containing heterocyclic ring formed does not contain a S—S or S—O bond, and at least one of E, F and G is a heteroatom;

J is C or N;

$J_a$ is C or N, provided that only one of J and $J_a$ can be N, and each of J and $J_a$ can be C; and provided that when the bicyclic ring is an indazole, $J_a$ is C;

M is selected from hydrogen, alkyl, cycloalkyl, cycloalkenyl, aryl, heterocyclo, and heteroaryl;

$M_a$ is a linker between C and M and is selected from a bond; $C_1$-$C_5$ alkylene;

$C_1$-$C_5$ alkylene which includes at any position in the chain a) a nitrogen which is substituted with alkyl, b) an oxygen, c) a sulfur, or d) an $SO_2$ group;

—$C(R_{m^1})(R_{m^2})C(=O)N(R_{m^3})$—;   —$C(=O)N(R_{m^1})C(R_{m^2})(R_{m^3})$—;

—$C(R_{m^1})(R_{m^2})S(=O)_2N(R_{m^3})$—;   —$S(=O)_2N(R_{m^1})C(R_{m^2})(R_{m^3})$—; and —$N(R_{m^1})C(=O)N(R_{m^2})$—; where $R_{m^1}$, $R_{m^2}$ and $R_{m^3}$ are the same or different and at each occurrence independently selected from H and $C_1$-$C_4$ alkyl, or $R_{m^1}$ and $R_{m^2}$ combine to form a $C_{3-6}$ carbocyclic or heterocyclo ring;

Q is selected from
(i) hydrogen, halogen, nitro, cyano, hydroxy, or $C_1$-$C_4$ alkyl;
(ii) Q and $R_6$ are combined with the carbons to which they are attached to form a 3- to 6-membered cycloalkyl; or
(iii) Q and -$M_a$-M are combined with the carbons to which they are attached to form a 3- to 7-membered ring containing 0, 1 or 2 heteroatoms which are the same or different and are independently selected from the group consisting of O, S, $SO_2$, and

which ring may be optionally substituted with 0-2 $R_3$ groups or carbonyl;

Z is selected from H, alkyl, cycloalkyl, heterocyclo, aryl, heteroaryl, —C(=O)C(=O)$R_{22}$, —C(=O)$NR_8R_9$, —C(=O)$R_8$, —C(NCN)$NR_8R_9$, —C(=O)$OR_8$, —$SO_2R_8$,

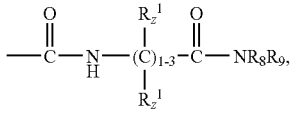

and —$SO_2NR_8R_9$;

$Z_a$ is a linker between N and Z and is selected from a bond; $C_1$-$C_5$ alkylene;

$C_1$-$C_5$ alkylene which includes at any position in the chain a nitrogen which is substituted with alkyl, or an $SO_2$ group;

—$C(R_{z^1})(R_{z^2})C(=O)N(R_{z^3})$—; and

—$C(R_{z^1})(R_{z^2})S(=O)_2N(R_{z^3})$— (where $R_{z^1}$ and $R_{z^2}$ at each occurrence are independently selected from H, $C_1$-$C_4$ alkyl and halogen, and $R_{z^3}$ is H or $C_1$-$C_4$ alkyl);

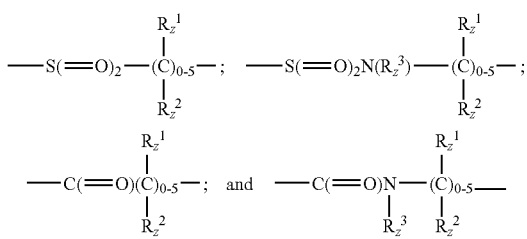

(wherein for each C in the chain

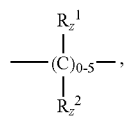

$R_z^1$ and $R_z^2$ are independently H, $C_1$-$C_4$ alkyl or halogen, and the right side of each $Z_a$ group is linked to Z);

$Z_b$ is H or alkylaminocarbonyl;

$Z_c$, $R_x$, $R_y$, $R_1$, $R_{1a}$ and $R_{1b}$ are the same or different and at each occurrence are independently selected from hydrogen, alkyl, alkenyl, alkynyl, cycloalkyl, cycloalkenyl, aryl, heteroaryl, and heterocyclo;

$R_2$, $R_{2a}$ and $R_{2b}$ are the same or different and at each occurrence are independently selected from hydrogen, halogen, alkyl, alkenyl, alkynyl, nitro, cyano, —$OR_{10}$, —$NR_{10}R_{11}$, —C(=O)$R_{10}$, —$CO_2R_{10}$, —C(=O)$NR_{10}R_{11}$, —O—C(=O)$R_{10}$, —$NR_{10}$C(=O)$R_{11}$, —$NR_{10}$C(=O)$OR_{11}$, —$NR_{10}$C(S)$OR_{11}$, —S(=O)$_pR_{12}$, —$NR_{10}SO_2R_{12}$, —$SO_2NR_{10}R_{11}$, cycloalkyl, cycloalkenyl, cycloalkynyl, heterocyclo, aryl, and heteroaryl;

$R_3$ at each occurrence is independently selected from hydrogen, halogen, alkyl, alkenyl, alkynyl, nitro, cyano, —$OR_{13}$, —$NR_{13}R_{14}$, —C(=O)$R_{13}$, —$CO_2R_{13}$, —C(=O)$NR_{13}R_{14}$, —O—C(=O)$R_{13}$, —$NR_{13}$C(=O)$R_{14}$, —$NR_{13}$C(=O)$OR_{14}$, —$NR_{13}$C(S)$OR_{14}$, —S(=O)$_pR_{15}$, —$NR_{13}SO_2R_{15}$, —$SO_2NR_{13}R_{14}$, cycloalkyl, cycloalkenyl, cycloalkynyl, heterocyclo, aryl, and heteroaryl;

$R_4$ is selected from hydrogen, alkyl, halogen, and $C_1$-$C_4$ alkoxy;

$R_6$ is selected from hydrogen, halogen, alkyl, alkenyl, alkynyl, nitro, cyano, —$OR_{16}$, —$NR_{16}R_{17}$, —C(=O)$R_{17}$, —$CO_2R_{17}$, —C(=O)$NR_{16}R_{17}$, —O—C(=O)$R_{16}$, —$NR_{16}$C(=O)$R_{17}$, —$NR_{16}$C(=O)$OR_{17}$, —$NR_{16}$C(=S)$OR_{17}$, —S(=O)$_pR_{18}$, —$NR_{16}SO_2R_{18}$, —$SO_2NR_{16}R_{17}$, cycloalkyl, cycloalkenyl, heterocyclo, aryl, and heteroaryl;

$R_7$ is selected from hydrogen, halogen, alkyl, alkenyl, alkynyl, nitro, cyano, —$OR_{19}$, —$NR_{19}R_{20}$, —C(=O)$R_{19}$, —$CO_2R_{19}$, —C(=O)$NR_{19}R_{20}$, —O—C(=O)$R_{19}$, —$NR_{19}$C(=O)$R_{20}$, —$NR_{19}$C(=O)$OR_{20}$, —$NR_{19}$C(=S)$OR_{20}$, —S(=O)$_pR_{21}$, —$NR_{19}SO_2R_{21}$, —$SO_2NR_{19}R_{20}$, cycloalkyl, cycloalkenyl, cycloalkynyl, heterocyclo, aryl, and heteroaryl, provided that where $R_6$ is H and $R_7$ is aryl, $R_7$ is substituted phenyl;

or $R_6$ and $R_7$ are taken together with the carbon to which they are attached to form a cycloalkyl, cycloalkenyl, or heterocyclo group;

$R_5$, $R_8$, $R_9$, $R_{10}$, $R_{11}$, $R_{13}$, $R_{14}$, $R_{16}$, $R_{17}$, $R_{19}$ and $R_{20}$ are the same or different and at each occurrence are independently selected from (i) hydrogen, alkyl, alkenyl, alkynyl, cycloalkyl, cycloalkenyl, aryl, heteroaryl, carboxy, alkoxycarbonyl, and heterocyclo; or (ii) with respect to Z, $R_8$ is taken together with $R_9$; and/or with respect to $R_3$, $R_{13}$ is taken together with $R_{14}$; and/or with respect to $R_6$, $R_{16}$ is taken together with $R_{17}$; and/or with respect to $R_7$, $R_{19}$ is taken together with $R_{20}$, each of which forms a 4- to 6-membered heteroaryl, and heterocyclo ring;

$R_{12}$, $R_{15}$, $R_{18}$, and $R_{21}$ are the same or different and are independently selected from alkyl, alkenyl, alkynyl, cycloalkyl, cycloalkenyl, aryl, heteroaryl, and heterocyclo; and $R_{22}$ is selected from alkyl and alkoxy;

p is 0, 1 or 2;

provided that where X is

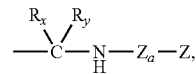

then 1) at least one of Q, $M_a$-M, $R_6$ and $R_7$ must be other than hydrogen; or 2) where E is $NR_1$, F is $CR_{2a}$ and G is $CR_{2b}$, or G is $NR_{1b}$, F is $CR_{2a}$ and E is $CR_2$, so that the resulting bicyclic ring is an indole, then $R_{1a}$, $R_{2a}$ and/or $R_{2b}$ cannot be —$NH_2$; or 3) where E is $NR_1$, F is N and G is $CR_{2b}$, or G is $NR_{1b}$, F is N and E is $CR_2$, so that the resulting bicyclic ring is an indazole, then $R_1$, $R_{1b}$, $R_2$ and $R_{2a}$ cannot be $NH_2$; or 4) —$Z_a$—Z is other than H; or 5) when Q and $R_6$ are combined with the carbons to which they are attached to form a 3- to 6-membered cycloalkyl, —$Z_a$—Z cannot be alkyl; or 6) $Z_a$—Z cannot be a substituted or unsubstituted 4-piperidinyl group; or 7) each of $R_1$, $R_{1a}$, $R_{1b}$, $R_2$, $R_{2a}$ and $R_{2b}$ is other than —C(=O)$CH_2NO_2$; or 8) when the bicyclic ring is an indazole and Q and M-$M_a$ (and the carbon to which they are attached) combine to form a 5- or 6-membered ring, then —$Z_a$—Z cannot be H or $C_1$-$C_5$ alkyl or —C(=O)C(=O)$NH_2$; or 9) when Q and $R_6$ (and the carbons to which they are attached) combine to form a substituted or unsubstituted 3- to 6-membered carbocyclic ring, neither $Z_a$ nor Z can be H or alkyl; or 10) when the bicyclic ring is benzofuranyl, isobenzofuranyl, indolyl or isoindolyl, $Z_a$ is other than $CH_2$ and neither $Z_a$ nor Z is cycloalkyl or cycloalkenyl; or 11) where —$Z_a$—Z is alkyl or arylalkyl, then
 a) at least one of -$M_a$-M, Q, $R_6$, $R_7$, $R_x$ and $R_y$ is other than H or alkyl, or
 b) Q is other than H, or
 c) $R_6$ and $R_7$ are each other than H, or
 d) $R_x$ and $R_y$ are each other than H.

Thus, the compounds of the invention include compounds of the

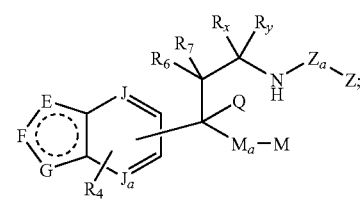

-continued
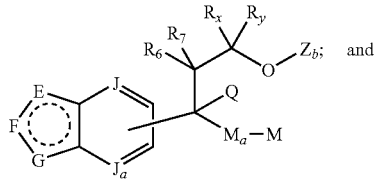
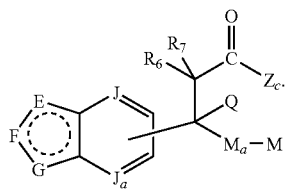
It is preferred that X is
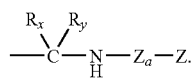
It is preferred that the group
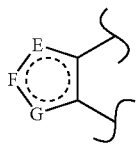
is a heteroaryl ring.
The ring system
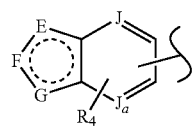
employed in the compounds of formula I includes the following ring systems:
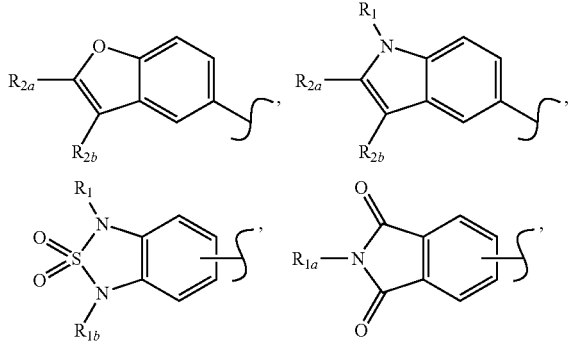
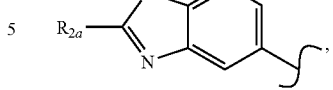
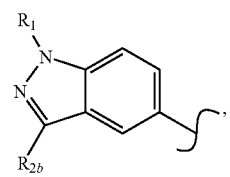
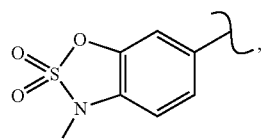
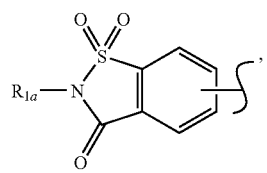
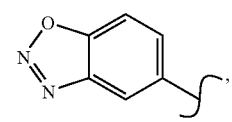
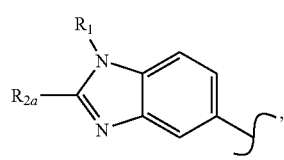
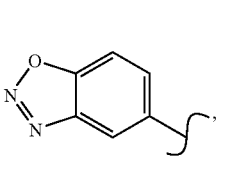
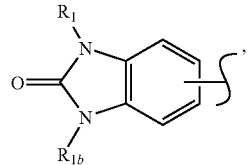
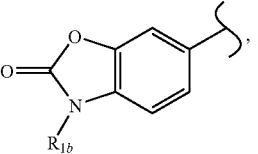
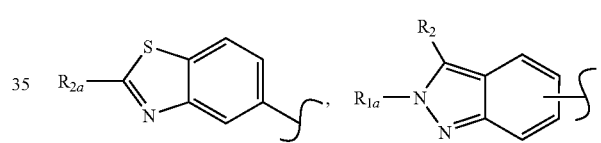
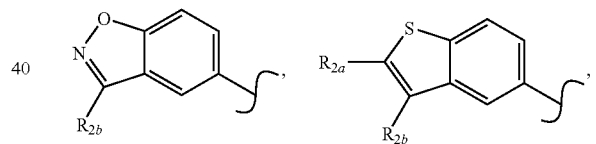
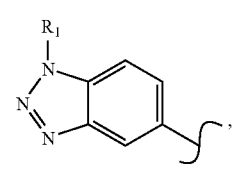
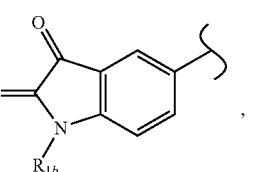
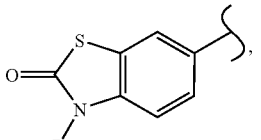
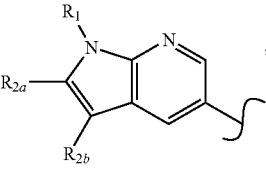
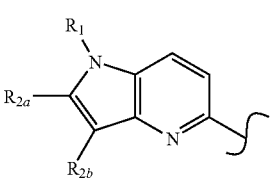
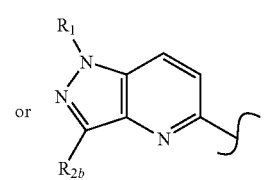
wherein each of the above ring systems may optionally include an $R_4$ group.

In addition, in compounds of formula I of the invention, where the ring system

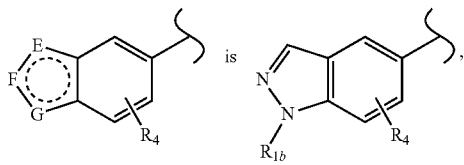

then where X is

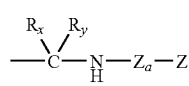

a) when -M$_a$-M is alkyl and —Z$_a$—Z is

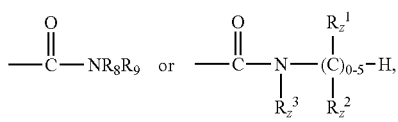

then —NR$_8$R$_9$ or

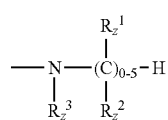

is other than

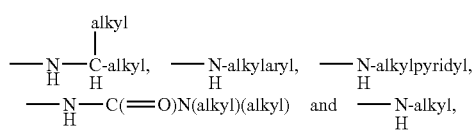

wherein the term "alkyl" by itself or as part of another group refers to unsubstituted straight chain or branched chain alkyl; or b) when -M$_a$-M is —C(R$_m{}^1$)(R$_m{}^2$)C(=O)N(R$_m{}^3$)H, then —Z$_a$—Z is other than

c) when —Z$_a$—Z is —SO$_2$R$_8$ or —SO$_2$C(R$_z{}^1$)(R$_z{}^2$)H, then -M$_a$-M is other than H, C$_1$-C$_4$ alkyl or —C(R$_m{}^1$)(R$_m{}^2$)C(=O)N(R$_m{}^3$)H; or d) where Q and/or M$_a$-M is H or C$_1$-C$_5$ alkyl or C$_1$-C$_5$ haloalkyl, and R$_6$ and R$_7$ are independently H, C$_1$-C$_5$ alkyl or C$_1$-C$_5$ haloalkyl, and R$_x$ and R$_y$ are independently H, C$_1$-C$_5$ alkyl or C$_1$-C$_5$ haloalkyl, and Z$_a$—Z is SO$_2$R$_8$, then R$_8$ is other than aryl or heteroaryl; or e) when -M$_a$-M is alkyl, aryl, heteroaryl, arylalkyl or heteroarylalkyl, then —Z$_a$—Z cannot be unsubstituted straight chain alkyl or unsubstituted branched chain alkyl, —SO$_2$—alkyl where alkyl is unsubstituted straight chain alkyl or unsubstituted branched chain alkyl, —SO$_2$H, —SO$_2$N(alkyl)(alkyl) where both alkyls are independently unsubstituted straight chain alkyl or unsubstituted branched chain alkyl, —SO$_2$NH—alkyl where alkyl is unsubstituted straight chain alkyl or unsubstituted branched chain alkyl, —C(=O) alkyl where alkyl is unsubstituted straight chain alkyl or unsubstituted branched chain alkyl, —SO$_2$NH$_2$, —C(=O)N(alkyl)(alkyl) where both alkyls are independently unsubstituted straight chain alkyl or unsubstituted branched chain alkyl, —C(=O)NH alkyl where alkyl is unsubstituted straight chain alkyl or unsubstituted branched chain alkyl or —C(=O)NH$_2$; or f) where the bicyclic ring is

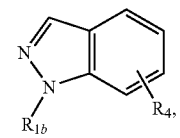

and -M$_a$-M is aryl or alkyl, then where —Z$_a$—Z is —SO$_2$-alkyl or —C(=O) alkyl, then the alkyl portion of the —Z$_a$—Z group is substituted straight chain alkyl or substituted branched chain alkyl where the substituent is other than alkyl.

It is preferred that in compounds of formula I,
E is CR$_2$ or NR$_1$;
F is N, NR$_{1a}$ or CR$_{2a}$;
G is NR$_{1b}$ or CR$_{2b}$; and
one of J$_a$ or J is optionally N;
or E is CR$_2$, F is N and G is

or E is NR$_1$, F is CR$_{2a}$ and G is CR$_{2b}$.

It is preferred that when the bicyclic ring is an indazole of the structure

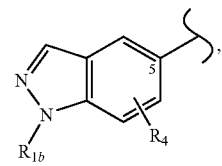

the side chain group is linked to the 5-position and not the 6-position.

It is preferred that in the compounds of formula I

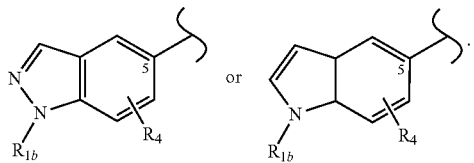

In more preferred embodiments of compounds of formula I,

G is $NR_{1b}$ and $R_{1b}$ is H, aryl, alkyl, heterocyclo, alkylsulfonylalkyl, heteroaryl, or hydroxyalkyloxyalkyl;

Z is heteroaryl, aryl, heterocyclo, cycloalkyl, alkylsulfonyl, haloalkylsulfonyl, or haloalkylcarbonyl;

$M_a$ is a bond;

M is aryl, alkyl, cycloalkyl, heteroaryl, arylalkyl, or hydroxyheteroaryl;

Q is hydrogen or alkyl, or Q and M-$M_a$ and the carbons to which they are attached can combine to form a heterocyclo ring, a cycloalkyl ring, or Q and $R_6$ and the carbons to which they are attached can combine to form a heterocyclo ring, a cycloalkyl ring.

In another preferred embodiment of the invention where (A) X is

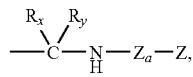

E is CH,

F is N or CH,

G is —$NR_{1b}$;

$R_{1b}$ is haloalkylaryl, haloaryl, haloalkylalkyl(halo)aryl, alkoxyaryl, alkoxycarbonylaryl, H, hydroxyalkyl, heterocyclo, alkylheterocyclo, alkylsulfonylalkyl, alkyl, heteroaryl, hydroxyaryl, alkoxyalkyl, arylalkyl, cycloalkyl, alkoxycarbonylaryl, or carboxyaryl;

Z is selected from heteroaryl, substituted heteroaryl, alkoxycarbonylheteroaryl, alkylheteroaryl, cycloalkyl, aminoheteroaryl, cyanoheteroaryl, cycloalkylheteroaryl, hydroxyheteroaryl, alkylthioheteroaryl, dialkylheteroaryl, haloalkylheteroaryl, haloheteroaryl, hydroxycycloalkyl, aminocycloalkyl, alkylcarbonylaminocycloalkyl, alkylsulfonyl, haloalkylsulfonyl, alkyl, and haloalkylcarbonyl;

$Z_a$ is a bond; alkyl;

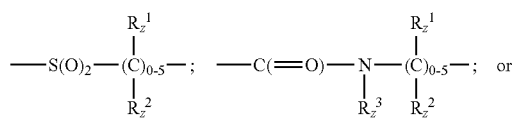

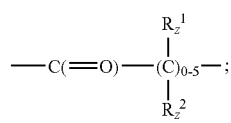

M is alkyl, aryl, cycloalkyl, heteroayl, arylalkyl, heterocyclo, alkylarylalkyl, alkylaryl, or haloaryl;

$M_a$ is a bond;

Q is H or alkyl; or

Q and $R_6$ and the carbons to which they are attached can be combined to form

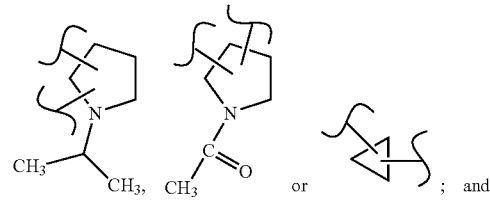

Q and M-$M_a$ and the carbons to which they are attached can be combined to form

In more preferred compounds of the invention where X is

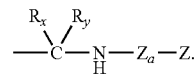

$R_x$ is H, alkyl or haloalkyl;
$R_y$ is H, alkyl or haloalkyl;
M is alkyl, haloalkyl, aryl, cycloalkyl, or alkenyl;
$M_a$ is a bond;
Q is H or $CH_3$;
$Z_a$ is a bond or alkyl; and
Z is H, amino, alkylcarbonyl, haloalkylcarbonyl (preferably $CF_3$, $CH_2CF_3$ or

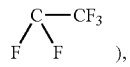), heteroarylcarbonyl, aminocarbonyl, alkoxycarbonylcarbonyl, carboxycarbonyl, heteroaryl, substituted heteroaryl, haloalkylsulfonyl, alkylaminocarbonyl, cyanoalkylcarbonyl, arylcarbonyl, alkylsulfonyl, alkoxyalkylcarbonyl, dialkylaminoalkylcarbonyl, alkylsulfonylalkylcarbonyl, arylalkylcarbonyl, heteroarylalkylcarbonyl, heterocyclocarbonyl, cycloalkylcarbonyl, heterocycloalkylcarbonyl (or cycloheteroalkylalkylcarbonyl), alkylcarbonylaminoalkylcarbonyl, alkoxyarylalkylcarbonyl, alkylsulfonyl, arylsulfonyl, arylalkylsulfonyl, arylaminocarbonyl, alkoxycarbonyl, carboxyalkylcarbonyl, alkylcarbonylalkylcarbonyl, aminosulfonylalkylcarbonyl, hydroxyalkylcarbonyl, haloalkylcycloalkylcarbonyl, haloalkylalkylcarbonyl, cycloalkylsulfonyl, alkylsulfonylalkylsulfonyl, haloalkylarylsulfonyl, dialkylaminosulfonyl, heterocycloaminocarbonyl, alkynylaminocarbonyl, diarylalkylaminocarbonyl, alkylthioalkyl(alkoxycarbonyl)aminocarbonyl, alkylcycloalkylaminocarbonyl, arylalkylaminocarbonyl, (hydroxylaryl)(alkoxyalkyl)aminocarbonyl, hydroxyheterocycloaminocarbonyl, arylalkylheterocycloaminocarbonyl, (haloarylalkyl)(hydroxyalkyl)aminocarbonyl, haloalkylalkylaminocarbonyl, cycloalkylaminocarbonyl, haloalkylalkoxycarbonyl, hydroxyalkylaminocarbonyl, alkyl(alkyl)aminocarbonyl (where alkyls are the same or different), heterocycloalkylaminocarbonyl,

hydroxyalkylheterocyclocarbonyl, aminoheterocyclocarbonyl, aminoalkylamino, alkoxycarbonylalkylaminocarbonyl, hydroxyalkylcycloalkylaminocarbonyl, alkylaminosulfonyl, alkylheterocyclo, dihydroxyalkyl(alkyl)aminocarbonyl, (hydroxyl)alkyl, carboxyalkylaminocarbonyl, cyanoheterocycloaminocarbonyl, heterocyclocarbonylalkylaminocarbonyl, haloarylalkylaminocarbonyl, dialkylaminocarbonyl, alkylcarbonylcarbonyl, arylaminocarbonylalkylaminocarbonyl, haloarylalkylcarbonyl, alkyl(hydroxyl)alkylcarbonyl, alkenylheterocycloaminocarbonyl, hydroxyalkyl(alkyl)aminoalkylaminocarbonyl.

In another preferred embodiment of the invention (B) X is

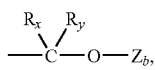

E is CH,
F is N or CH,
G is —$NR_{1b}$;
where $R_{1b}$ is aryl;
$R_6$ is alkyl or H;
$R_7$ is alkyl or H;
$R_x$ is H or alkyl;
$R_y$ is alkyl, aryl, cycloalkyl, or heteroalkyl;
$Z_b$ is H or

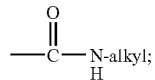

M-$M_a$ is aryl; and
Q is H;
or (C) X is

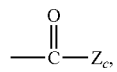

E is CH,
F is N or CH,
G is —$NR_{1b}$;
where $R_{1b}$ is aryl;
M-$M_a$ is aryl;
$Z_c$ is alkyl, aryl, cycloalkyl, or heteroaryl.

In still more preferred embodiments of compounds of formula I,

Z is substituted heteroaryl which is substituted with one, two or three groups which are the same or different and are independently selected from hydrogen, halogen, alkyl, substituted alkyl, alkenyl, substituted alkenyl, alkynyl, substituted alkynyl, nitro, cyano, $OR_1^c$, $NR_1^aR_1^b$, $C(=O)R_1^c$, $CO_2R_1^c$, $C(=O)NR_1^aR_1^b$, —O—$C(=O)R_1^c$, $NR_1^aC(=O)R_1^b$, $NR_1^aC(=O)OR_1^b$, $NR_1^aC(=S)OR_1^b$, $S(O)_{p_1}R^c$, $NR_1^aSO_2R_1^b$, $SO_2NR_1^aR_1^b$, cycloalkyl, cycloalkenyl, heterocyclo, aryl, or heteroaryl;

$R_1^a$, $R_1^b$, and $R_1^c$, are the same or different and are independently selected from (i) hydrogen, alkyl, substituted alkyl, alkenyl, substituted alkenyl, alkynyl, substituted alkynyl, cycloalkyl, cycloalkenyl, aryl, heteroaryl, and heterocyclo; or (ii) where possible $R_1^a$ is taken together with $R_1^b$ to form a heteroaryl or heterocyclo ring; and $p_1$ is 0, 1 or 2.

In more preferred compounds of formula I of the invention

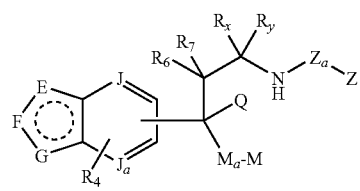

IA

E is CH;
F is N or CH, preferably N;
G is

$R_{1b}$ is

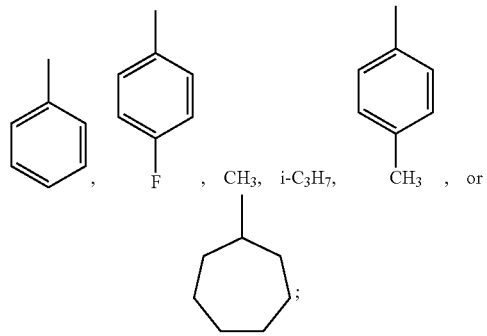

$R_6$ is H or $CH_3$;
$R_7$ is H, $CH_3$, $C_2H_5$, $C_3H_7$, $C_6H_5$,

i-$C_3H_7$, or —$CH_2$—CN=$CH_2$;
or $R_6$ and $R_7$ together form

$R_4$ is H;
$R_x$ is H, $CH_3$ or $CF_3$;

$R_y$ is H, $CH_3$ or $CF_3$;
$M_a$ is a bond;
$M-M_a$ is
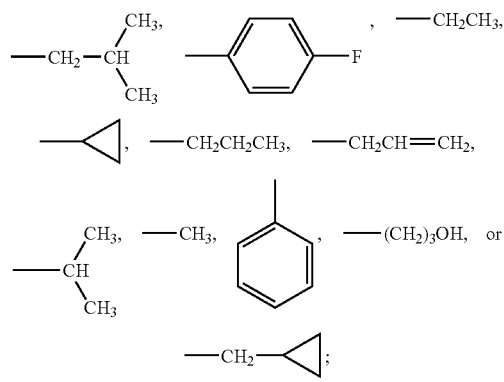
or Q and $M-M_a$ and the carbons to which they are attached are taken together to form
Q is H or $CH_3$;
$-Z_a-Z$ is
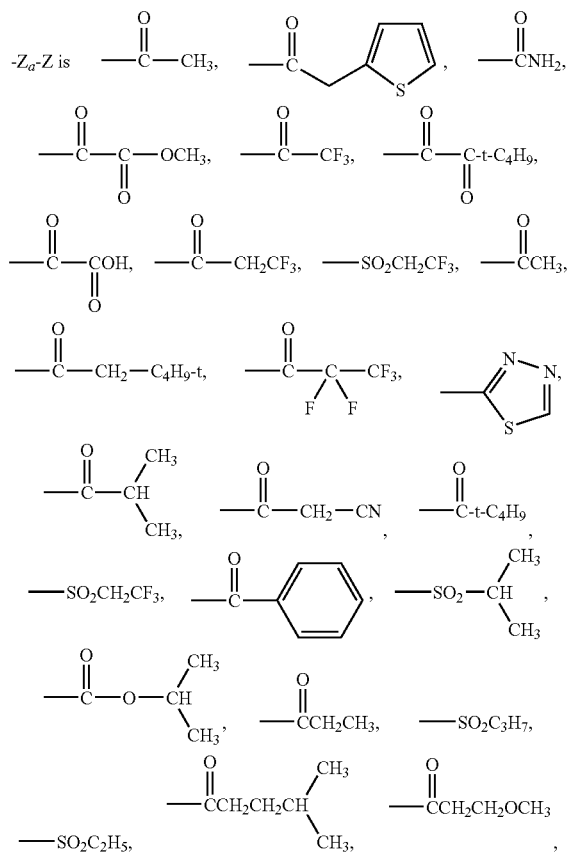
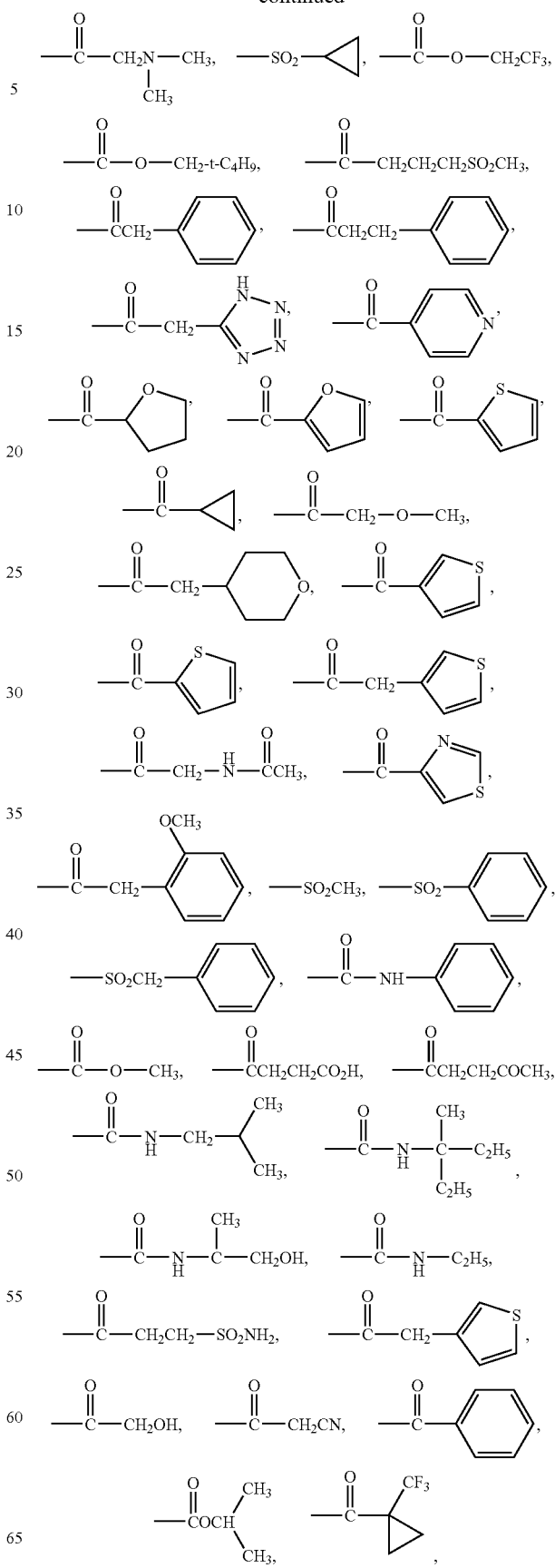

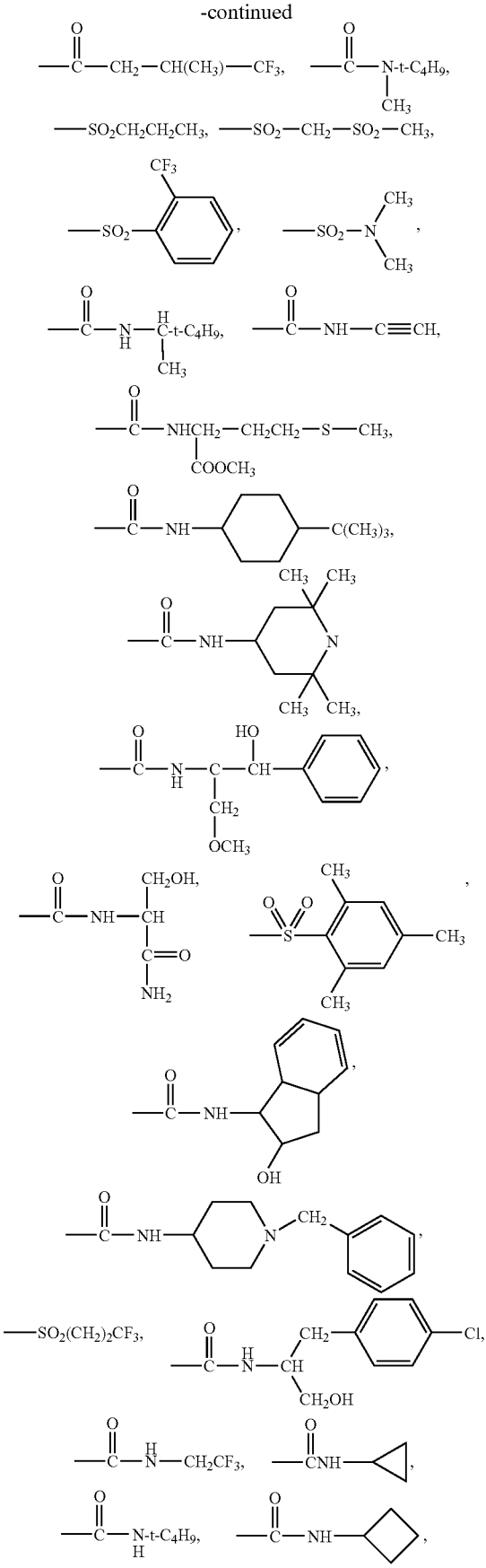
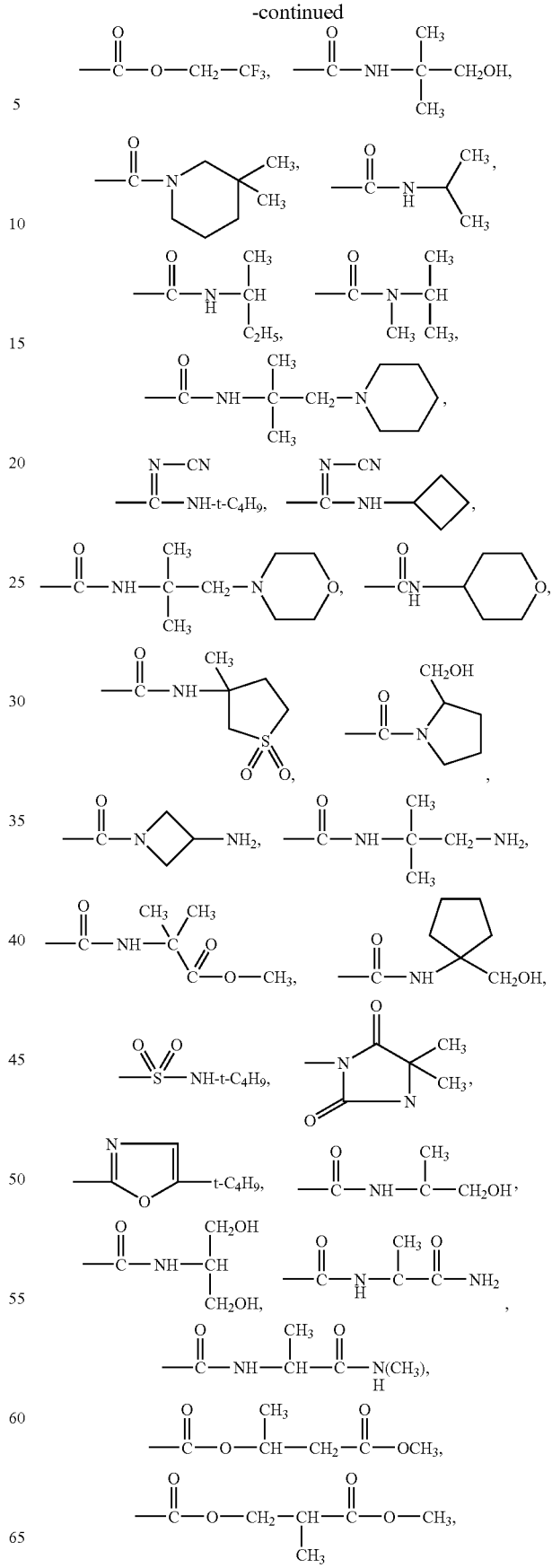

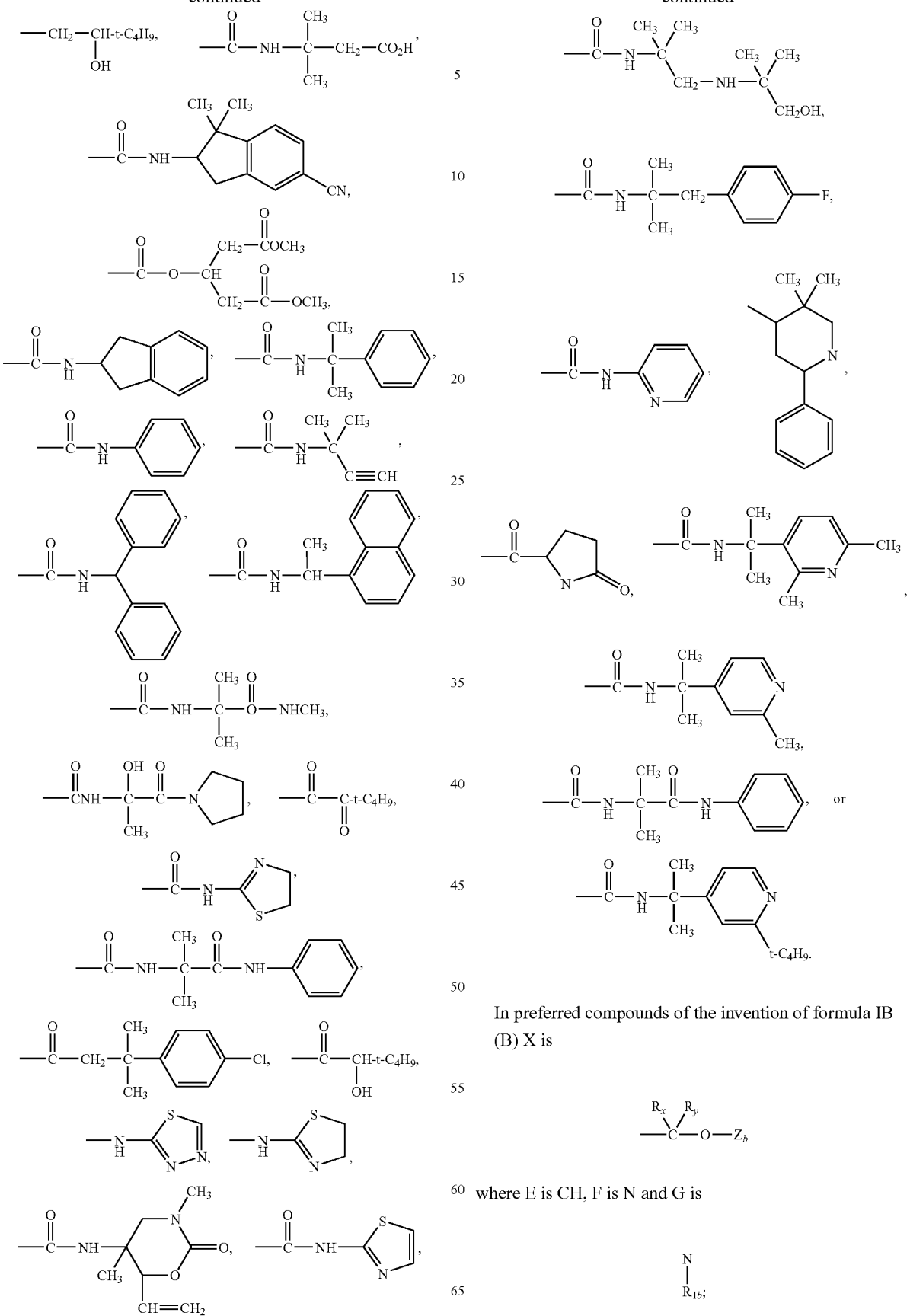
In preferred compounds of the invention of formula IB (B) X is
$$-\overset{R_x}{\underset{R_y}{C}}-O-Z_b$$
where E is CH, F is N and G is
$$\underset{R_{1b}}{\overset{N}{|}};$$

where $R_{1b}$ is

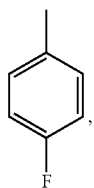

$R_6$ is $CH_3$ or H,
$R_7$ is $CH_3$ or H,
$R_x$ is H, $CH_3$, or $CF_3$,
$R_y$ is $CH_3$, phenyl, cyclopropyl,

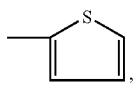

benzyl, or $CF_3$,
$Z_b$ is H or

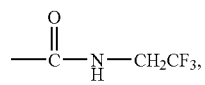

$M\text{-}M_a$ is phenyl,
Q is H.
In preferred compounds of the invention of formula IC
(C) X is

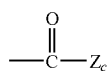

where E is CH, F is N and G is

where $R_{1b}$ is

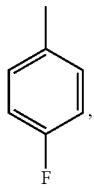

$Z_c$ is $CH_3$, phenyl, cyclopropyl,

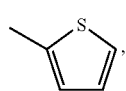

or $CF_3$,
$M\text{-}M_a\text{-}$ is phenyl,
or a pharmaceutically acceptable salt thereof.

More preferred are compounds of the structure

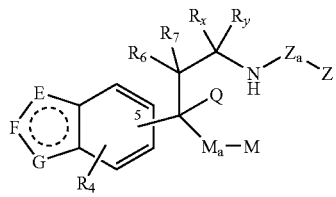

IA where E is CH,
F is CH or N, and
G is

where $R_{1b}$ is phenyl or 4-substituted phenyl;
$R_4$ is H or $CH_3$;
$R_6$ is H or $CH_3$;
$R_7$ is H or $CH_3$;
Q is H;
M is phenyl;
$M_a$ is a bond;
Z is haloalkyl;
$Z_a$ is $SO_2$ or CO;
$R_x$ is H;
$R_y$ is H;
or a pharmaceutically acceptable salt thereof The following compounds represent preferred embodiments of the invention

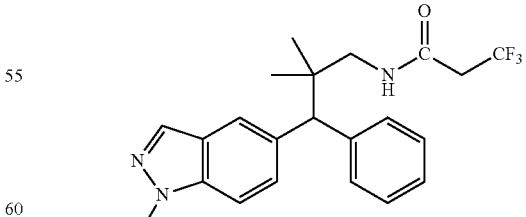

and

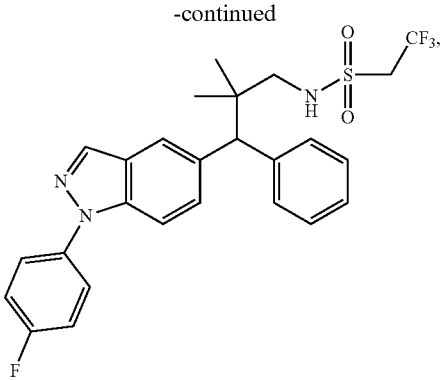

or a pharmaceutically acceptable salt thereof.

In addition, in accordance with the compounds of the invention within the scope of compounds of formula IA below are provided as listed below:

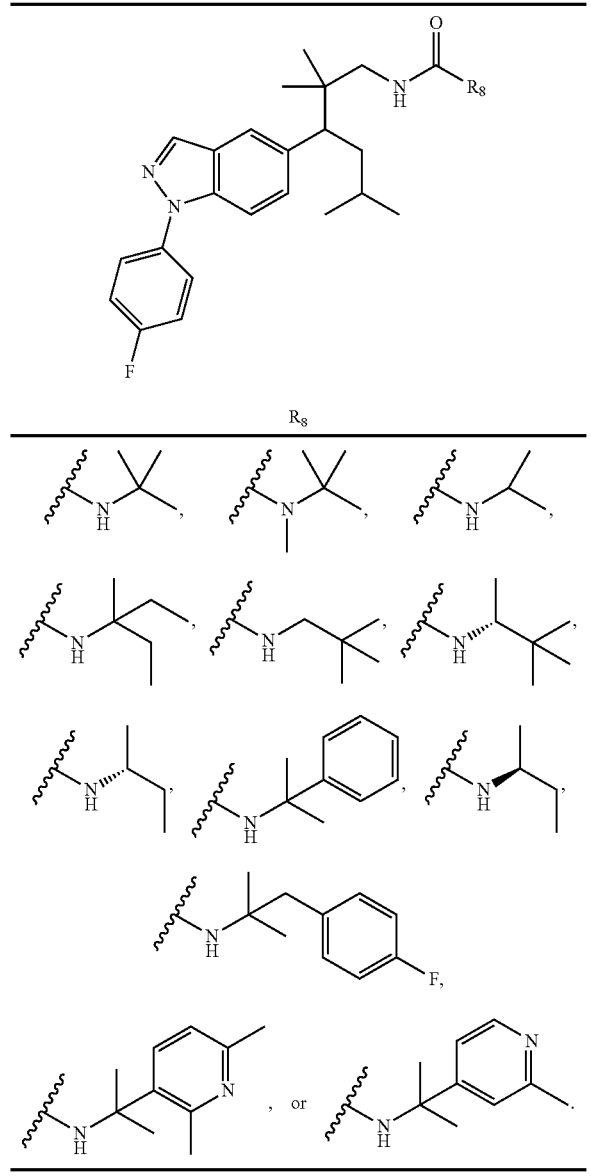

In another embodiment of the present invention, there is provided pharmaceutical compositions useful in treating endocrine disorders, rheumatic disorders, collagen diseases, dermatologic disease, allergic disease, ophthalmic disease, respiratory disease, hematologic disease, gastrointestinal disease, metabolic diseases, inflammatory disease, autoimmune disease, and neoplastic disease, as well as other uses as described herein, which including a therapeutically effective amount (depending upon use) of a compound of formula (I) of the invention and a pharmaceutically acceptable carrier.

In still another embodiment, the present invention provides a method of treating endocrine disorders, rheumatic disorders, collagen diseases, dermatologic disease, allergic disease, ophthalmic disease, respiratory disease, hematologic disease, gastrointestinal disease, inflammatory disease, immune disease, metabolic disease (diabetes and/or obesity), and neoplastic disease. A disease associated with the expression product of a gene whose transcription is stimulated or repressed by glucocorticoid receptors, or a disease associated with AP-1- and/or NF-κB-induced transcription, or a disease associated with AP-1 and/or NF-κB dependent gene expression, wherein the disease is associated with the expression of a gene under the regulatory control of AP-1 and/or NF-κB (particularly AP-1), including inflammatory and immune diseases and disorders as described hereinafter, which includes the step of administering a therapeutically effective amount of a compound of formula (I) of the invention to a patient.

Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κB- (particularly AP-1-) induced transcription, or a method for treating a disease or disorder associated with AP-1 and/or NF-κB (particularly AP-1) dependent gene expression, wherein the disease is associated with the expression of a gene under the regulatory control of AP-1 and/or NF-κB (particularly AP-1), such as inflammatory and immune disorders, cancer and tumor disorders, such as solid tumors, lymphomas and leukemia, and fungal infections such as mycosis fungoides.

Another embodiment of the present invention involves a) a method for treating a disease or disorder associated with or mediated by the expression product of a gene whose transcription is stimulated or repressed by glucocorticoid receptors, or b) a method of treating a disease or disorder associated with or mediated by AP-1- and/or NF-κB- (particularly AP-1-) induced transcription, or c) a method for treating a disease or disorder associated with or mediated by AP-1 and/or NF-κB (particularly AP-1) dependent gene expression, wherein the disease is associated with or mediated by the expression of a gene under the regulatory control of AP-1 and/or NF-κB (particularly AP-1), such as inflammatory and immune disorders, cancer and tumor disorders, such as solid tumors, lymphomas and leukemia, and fungal infections such as mycosis fungoides, which includes the step of administering to a patient in need of treatment a therapeutically effective amount of a compound of formula (IA) of the invention, which compound has the formula

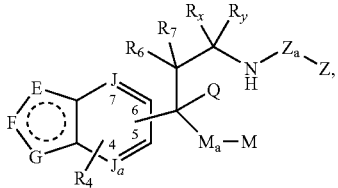

its enantiomers, diastereomers, tautomers, a prodrug ester thereof, or a pharmaceutically-acceptable salt, or hydrate, thereof, wherein:

the side chain group

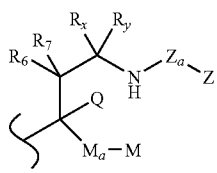

is attached to the bicyclic ring

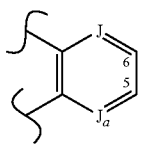

at the 5- or 6-position;

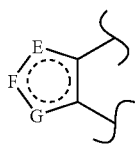

is heterocyclo or heteroaryl;
and wherein E, F, G, J, $J_a$, $R_4$, $R_6$, $R_7$, $R_x$, $R_y$, $M_a$, M, Q, $Z_a$ and Z are as defined above. The provisos 1) to 11) as defined above for the formula I compound of the invention do not apply to this embodiment of the invention.

In a preferred embodiment, in compound IA, —$Z_a$—Z is

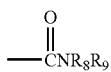

or

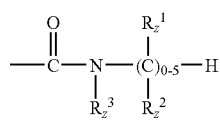

where $R_8$, $R_9$, $R_z^1$, $R_z^2$ and $R_z^3$ are as defined above.

The term "disease associated with GR transactivation," as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary andrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

The terms "glucocorticoid receptor" and "GR," as used herein, refer either to a member of the nuclear hormone receptor ("NHR") family of transcription factors which bind glucocorticoids and either stimulate or repress transcription, or to GR-beta.

These terms, as used herein, refer to glucocorticoid receptor from any source, including but not limited to: human glucocorticoid receptor as disclosed in Weinberger et al., *Science*, 228:740-742 (1985), and in Weinberger et al., *Nature*, 318:670-672 (1986); rat glucocorticoid receptor as disclosed in Miesfeld, R., *Nature*, 312:779-781 (1985); mouse glucocorticoid receptor as disclosed in Danielson, M. et al., *EMBO J.*, 5:2513 (1986); sheep glucocorticoid receptor as disclosed in Yang, K. et al., *J. Mol. Endocrinol.*, 8:173-180 (1992); marmoset glucocorticoid receptor as disclosed in Brandon, D. D. et al., *J. Mol. Endocrinol.* 7:89-96 (1991); and human GR-beta as disclosed in Hollenberg, S. M. et al., *Nature*, 318:635 (1985); Bamberger, C. M. et al., *J. Clin Invest.*, 95:2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I diabetes, juvenile diabetes, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhea, pulmonary inflammation, eye uveitis, hepatitis, Graves' disease, Hashimoto's thyroiditis, autoimmune thyroiditis, Behcet's or Sjorgren's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, vitiligo (depigmentation of the skin), alopecia greata, autoimmune alopecia, autoimmune hypopituitarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and atherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, chronic obstructive pulmonary disease, solid organ transplant rejection, and sepsis.

In a preferred embodiment of the invention, the disease to be treated is an inflammatory or immune disease or disorder as defined hereinbefore.

Accordingly, one embodiment of the present invention is a method of treating a disease or disorder selected from an endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease, which includes the step of administering to a patient in need of treatment, a therapeutically effective amount of a compound of formula I.

Metabolic diseases to be treated, in accordance with the method of the invention, can include Type II diabetes and/or obesity. Type I diabetes and juvenile diabetes may also be considered metabolic diseases and as such may also be treated by the method of the invention.

In a preferable embodiment the disease or disorder to be treated is an inflammatory or autoimmune disease selected from transplant rejection of kidney, liver, heart, lung, pancreas, bone marrow, cornea, small bowel, skin allografts, skin homografts, heart valve xenograft, serum sickness, and graft vs. host disease, rheumatoid arthritis, psoriatic arthritis, multiple sclerosis, asthma, inflammatory bowel disease, Crohn's disease, ulcerative colitis, pyoderma gangrenum, systemic lupus erythematosis, myasthenia gravis, psoriasis, dermatitis, dermatomyositis; eczema, seborrhoea, pulmonary inflammation, eye uveitis, hepatitis, Graves' disease, Hashimoto's thyroiditis, autoimmune thyroiditis, Behcet's or Sjorgren's syndrome, pernicious or immunohaemolytic anaemia, atherosclerosis, Addison's disease, idiopathic adrenal insufficiency, autoimmune polyglandular disease, glomerulonephritis, scleroderma, morphea, lichen planus, vitiligo, alopecia greata, autoimmune alopecia, autoimmune hypopituitarism, Guillain-Barre syndrome, and alveolitis; contact hypersensitivity, delayed-type hypersensitivity, contact dermatitis, uticaria, skin allergies, respiratory allergies, hayfever, allergic rhinitis and gluten-sensitive enteropathy, osteoarthritis, acute pancreatitis, chronic pancreatitis, acute respiratory distress syndrome, Sezary's syndrome, restenosis, stenosis and atherosclerosis, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetitformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, sepsis, and chronic obstructive pulmonary disease.

In an even more preferable embodiment, the disease or disorder to be treated is selected from transplant rejection, rheumatoid arthritis, psoriatic arthritis, multiple sclerosis, asthma, inflammatory bowel disease, systemic lupus, erythematosis, and psoriasis.

In addition, in accordance with the present invention a method of treating a disease associated with AP-1-induced and/or NF-κB-induced transcription (particularly AP-1-induced transcription) is provided wherein a compound of formula (I) of the invention is administered to a patient at risk of developing the disease in a therapeutically effective amount to induce NHR transrepression of the AP-1-induced and/or NF-κB-induced transcription (particularly AP-1-induced transcription), thereby treating the disease.

Other therapeutic agents, such as those described hereafter, may be employed with the compounds of the invention in the present methods. In the methods of the present invention, such other therapeutic agent(s) may be administered prior to, simultaneously with or following the administration of the compound(s) of the present invention.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

In still another embodiment, pharmaceutical combinations are contemplated which include a compound as defined in claim 1, an enantiomer, diastereomer, or tautomer thereof, or a prodrug ester thereof, or a pharmaceutically-acceptable salt thereof, and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an anorectic agent, wherein the lipid-lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

More preferred combinations are those wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, N,N-2344, L895645, YM-440, R-119702, AJ9677, repaglinide, nateglinide, KAD1129, AR-HO39242, GW-409544, KRP297, AC2993, LY315902, P32/98 and/or NVP-DPP-728A, wherein the anti-obesity agent is orlistat, ATL-962, AJ9677, L750355, CP331648, sibutramine, topiramate, axokine, dexamphetamine, phentermine, phenylpropanolamine, and/or mazindol, wherein the lipid-lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427, wherein the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl)amino]-2,2-dimethyl-7-oxo-1H-azepine-1-acetic acid (gemopatrilat) or CGS 30440;

an angiotensin II receptor antagonist which is irbesartan, losartan or valsartan;

amlodipine besylate, prazosin HCl, verapamil, nifedipine, nadolol, propranolol, carvedilol, or clonidine HCl, wherein the platelet aggregation inhibitor is aspirin, clopidogrel, ticlopidine, dipyridamole or ifetroban;

the immunosuppressant is a cyclosporin, mycophenolate, interferon-beta, deoxyspergolin, FK-506 or Ant.-IL-2;

the anti-cancer agent is azathiprine, 5-fluorouracel, cyclophosphamide, cisplatin, methotrexate, thiotepa, or carboplatin;

the anti-viral agent is abacavir, aciclovir, ganciclovir, zidanocin, or vidarabine; and the antiinflammatory drug is ibuprofen, celecoxib, rofecoxib, aspirin, naproxen, ketoprofen, diclofenac sodium, indomethacin, piroxicam, prednisone, dexamethasone, hydrocortisone, or triamcinolone diacetate.

The invention may be embodied in other specific forms without departing from the spirit or essential attributes thereof. This invention also encompasses all combinations of alternative aspects and embodiments of the invention noted herein. It is understood that any and all embodiments may be taken in conjunction with any other embodiment to describe additional embodiments of the present invention. Furthermore, any elements of an embodiment are meant to be combined with any and all other elements from any of the embodiments to describe additional embodiments.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Example compounds are typically prepared as racemic mixtures. Preparation of Homochiral Examples May be Carried Out by Techniques Known to One skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Synthesis

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

As shown in Scheme 1, intermediates on the path to compounds of Formula I may be synthesized from benzannulated heterocyclic aldehydes II which are reported in the literature or synthesized by one skilled in the art. Grignard or aryl (alkyl)lithium reagents add to give alcohol III. This compound may be reacted with a silyl ketene acetal III-A in the presence of $TiCl_4$ to yield the alkylated product IV, and finally hydrolyzed (e.g., NaOH, DMSO, MeOH) to acid V. Alternatively, compound III can be oxidized to the ketone/aldehyde VII using a suitable oxidant (e.g., Dess-Martin periodinane) and then reacted with various enolates (the aldol reaction) or with a silyl ketene acetal III-A in the presence of a Lewis acid such as $BF_3OEt_2$ (the Mukaiyama aldol reaction) to give compound VIII. Compound VIII may be readily deoxygenated using trifluoroacetic acid in the presence of triethylsilane (or via a Barton deoxygenation: *Org. Lett.*, 4:39-42 (2002); *J. Org. Chem.*, 69:4124 (2004)) to give compound IV or hydrolyzed to form compound IX. By starting with benzannulated heterocyclic ester VI, one can use the Weinreb amidation procedure followed by organometallic addition to also synthesize intermediate VII. In the cases where M and Q are the same (or form a symmetrical ring), a parallel route can be employed by using two equivalents of the M-$M_a$-organometallic reagent to form alcohol X (also accessible from VII) that undergoes $TiCl_4$-mediated alkylation with silyl ketene acetals followed by hydrolysis as before to yield acid XII.

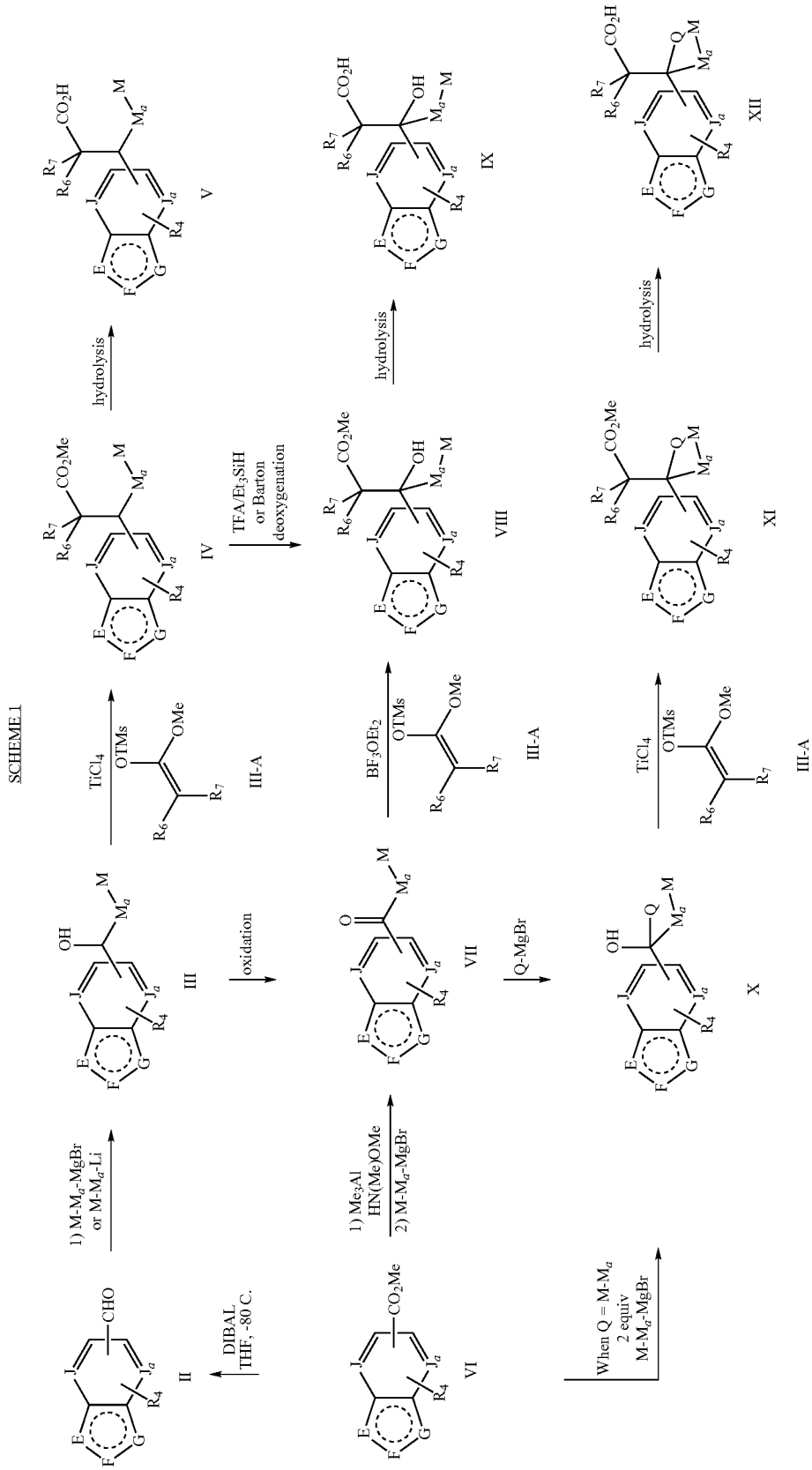

Many of the heterocyclic substituents of intermediates in Scheme 1 can be synthesized by one skilled in the art of organic synthesis. Other functional group manipulations that complement those in Scheme 1 are shown in Schemes 2 and 3.

Scheme 3 shows how an unsubstituted heterocycle XIV can be functionalized to intermediate VII using a modification of the classical Friedel-Crafts acylation (see *J. Med. Chem.*, 26:806 (1983)).

SCHEME 2

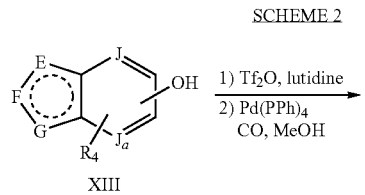

XIII

SCHEME 3

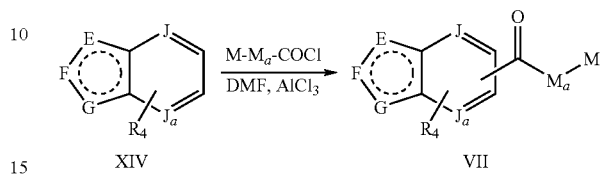

XIV                                    VII

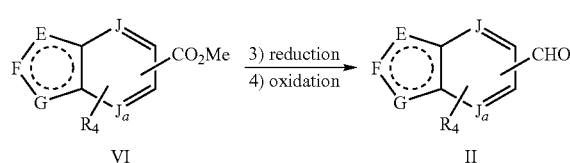

VI                                     II

Scheme 2 shows how phenolic intermediates such as XIII can be converted to a triflate followed by palladium-mediated carbonylation to form ester VI. The ester functionality can be transposed into an aldehyde (compound II) or other groups shown in Scheme 1.

A more specific implementation of the synthetic scheme outlined in Scheme 1 is shown in Scheme 4 using indazoles as a representative heterocycle. Starting aniline XV is converted to (1H-indazol-5-yl)methanol XVI-A using standard literature procedures (Sun et al., *J. Org. Chem.*, 62:5627-5629 (1997)). Functionalization of the indazole N-1 nitrogen (or N-2 nitrogen, not shown) via a Buchwald arylation procedure (*J. Org. Chem.*, 69:5578-5587 (2004); *J. Am. Chem. Soc.*, 123:7727-7729 (2001)) can be effected at multiple points during the synthetic scheme to ultimately provide compounds of Formula I. Alternatively, alkylation of the indazole N-1b nitrogen (or N-2 nitrogen) using a base and an $R_1$ alkylator (herein defined as a diverse electrophilic reagent that may undergo an SN2 reaction, e.g., a non-tertiary alkyl iodide or bromide, epoxide, etc.) in a suitable solvent may also provide intermediates in route to compounds of Formula I. Thus, compound XVI-A may be functionalized using a Buchwald arylation procedure or alkylated to give compound XVI-B.

SCHEME 4

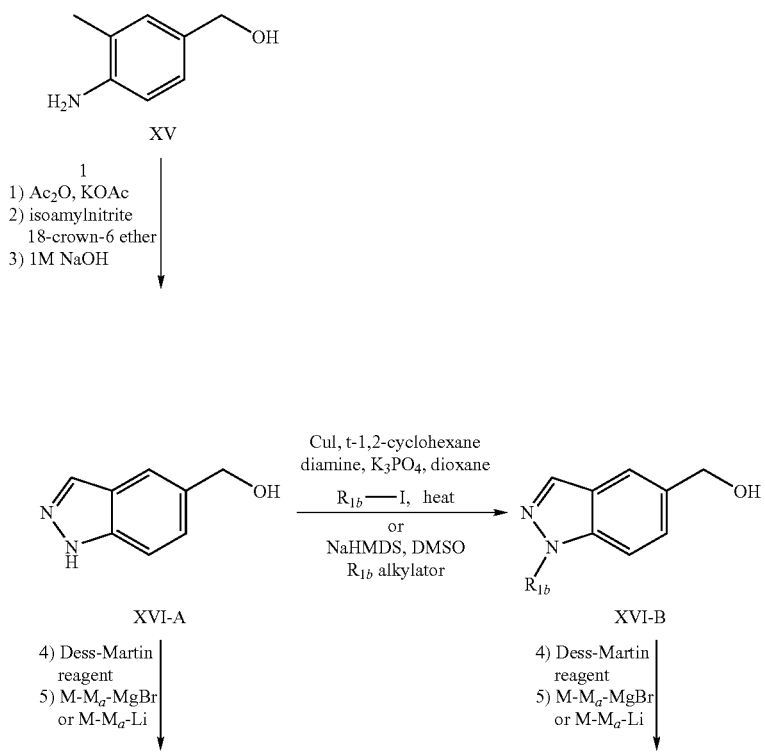

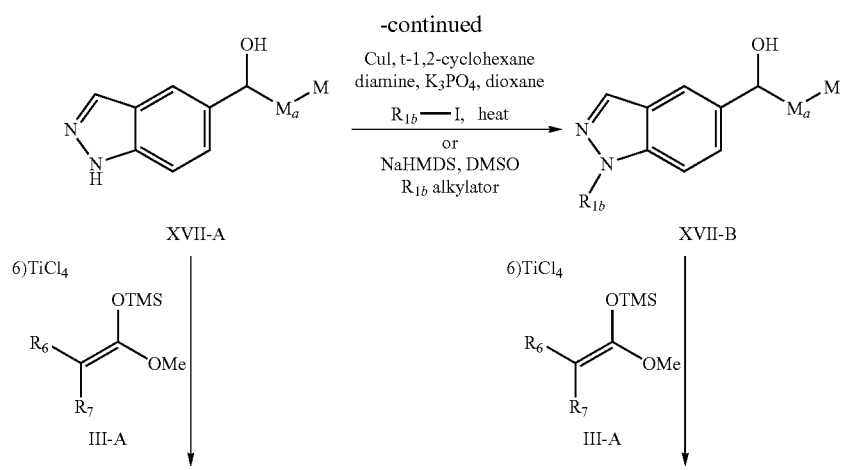

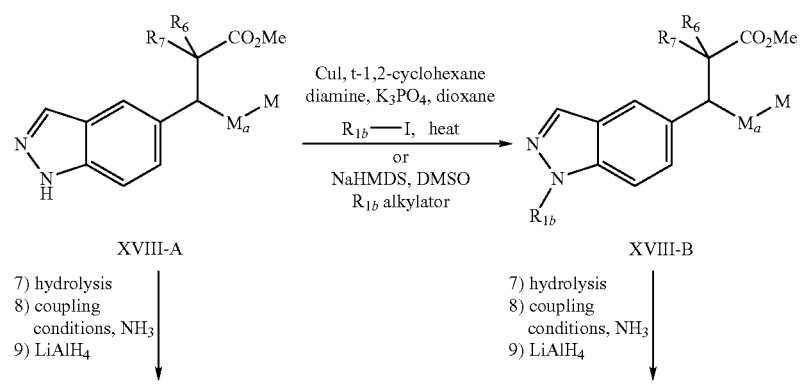

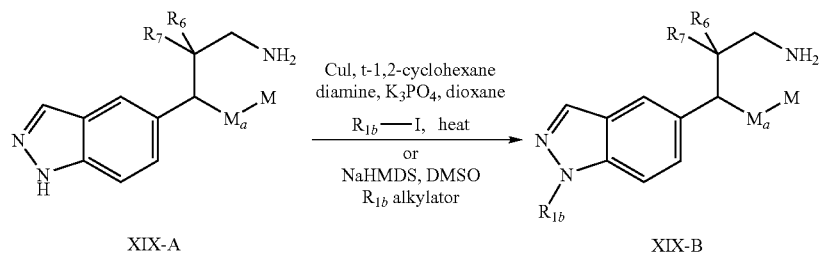

Oxidation of XVIA/B using a suitable oxidant (e.g., Dess-Martin reagent) followed by addition of a Grignard reagent or aryl/alkyllithium reagent provides XVII-A/B, respectively. XVII-A can be converted at this stage to XVII-B using the Buchwald arylation procedure or alkylated and XVII-A/B can be reacted with a silyl ketene acetal III-A in the presence of $TiCl_4$ to yield products XVIII-A/B. Again, XVIII-A may be optionally converted to XVIII-B at this point using the Buchwald procedure or alkylation. XVIII-A/B can then be hydrolyzed and coupled to ammonia to provide a carboxamide that in turn may be reduced with a reducing agent (e.g., $LiAlH_4$ or borane-THF) to give XIX-A/B. These intermediates may be converted to compounds of Formula I using coupling conditions described below in Scheme 11. Compound XIX-A can be converted to compound XIX-B using the Buchwald arylation procedure or alkylation.

A complementary route to Scheme 1 for making precursors to Formula I is shown in Scheme 5. Ketone/aldehyde VII can be homologated using the Horner-Wadsworth-Emmons procedure to make α,β-unsaturated ester XX which can be hydrogenated under palladium catalysis and then hydrolyzed to form compound XXII (same as compound V, where $R_6, R_7 = H$.). Alternatively, intermediate XX can be treated with a cuprate reagent (XX-A) containing the Q diversity to give XXIII and then hydrolyzed to XXIV. Alkylation of compound XXIII using LDA followed by an $R_6$ electrophile (such as an alkyl iodide) provides XXVI after hydrolysis. Intermediate XXV can be alkylated again using an $R_7$ electrophile to provide acid XII after hydrolysis.

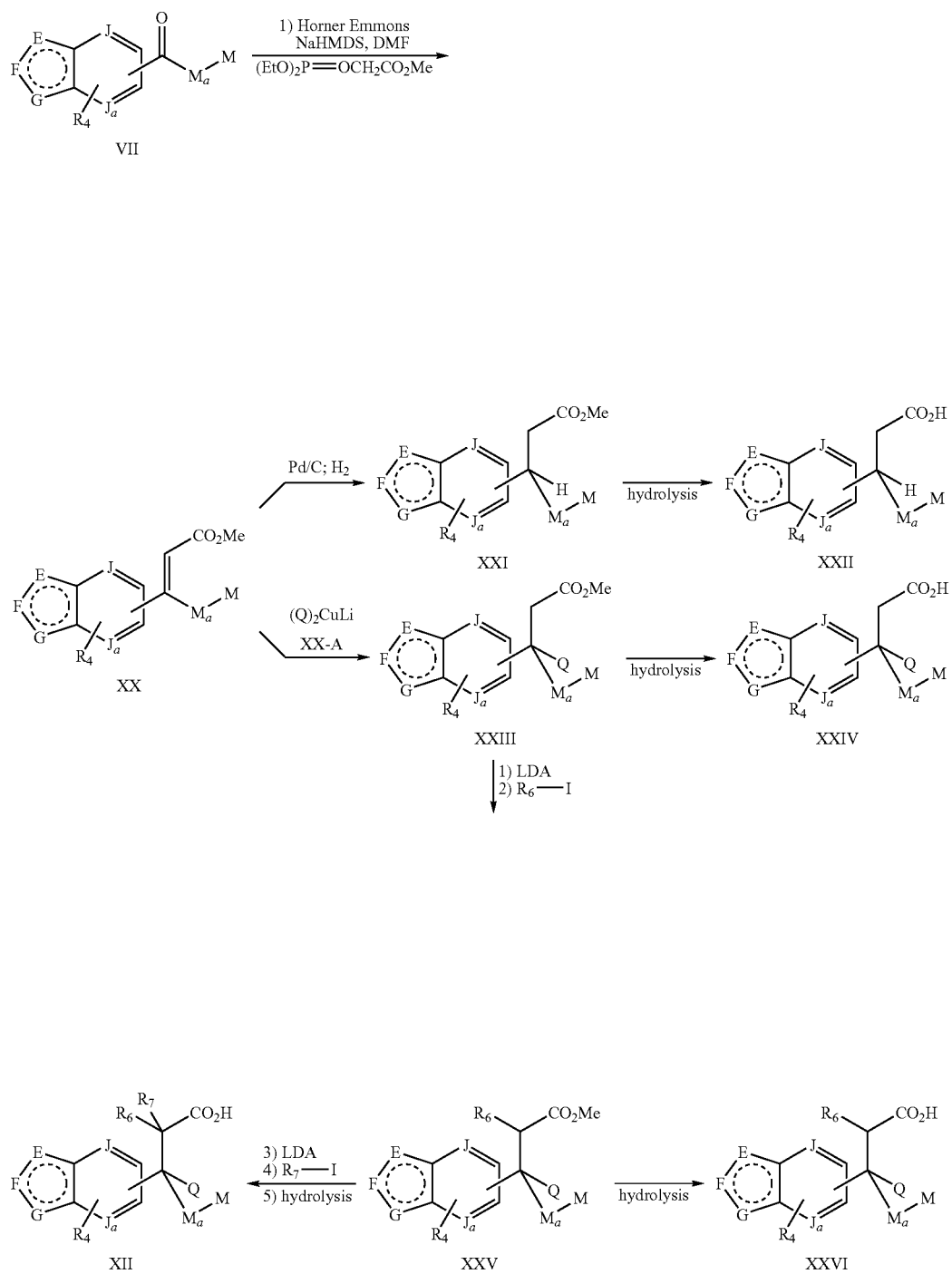

Another means of making intermediates on route to Formula I compounds is shown in Scheme 6. Metal-halogen exchange of compound XXVII using an alkyllithium reagent followed by treatment with a ketone or aldehyde provides compound X which can be transposed to compound XII as previously described in Scheme 1.

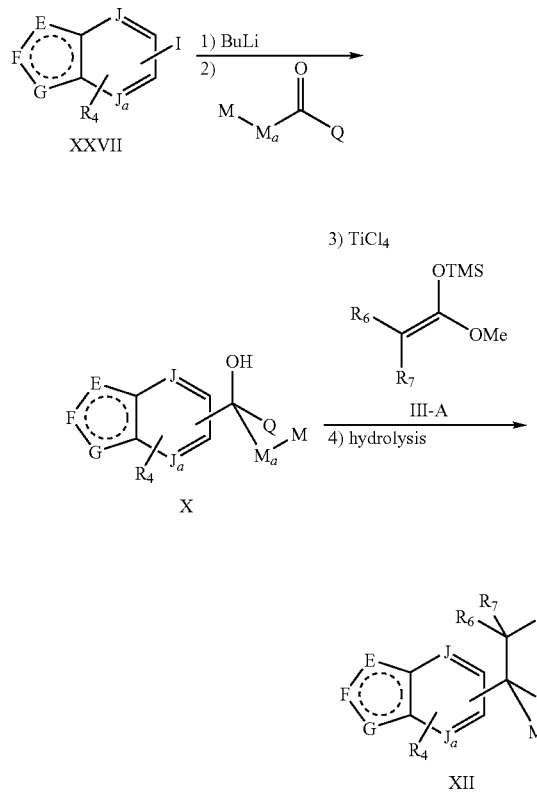

Scheme 7 illustrates a synthetic method to make precursors to compounds of Formula I. Treatment of compound VII with a nitrile-containing Horner-Emmons reagent followed by reduction with hydrogen and palladium gives primary amine XXVIII.

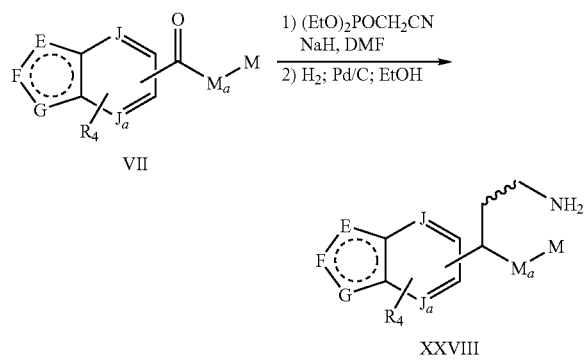

The synthetic Schemes 1, 2, 3, 5 and 6 above detail synthetic sequences that make carboxylic acids—precursors to compounds of Formula I. The final sequence involves converting the carboxylic acid to the carboxamide XXIX as shown in Scheme 8 for which there are many methods in the literature (Humphrey, *Chem. Rev.*, 97:2243-2266 (1997)). Reduction of the carboxamide to the primary amine using $LiAlH_4$ or borane or other suitable reagent yields compound XXX.

Scheme 9 shows a number of esters IV, VIII, etc. (methyl shown, but can be others) that can be converted into aldehyde IC' directly by low temperature DIBAL reduction or reduction all the way to a primary alcohol with a reducing agent (e.g., $LiAlH_4$) followed by oxidation using a numbers of reagents (e.g., Dess-Martin periodinane) to the aldehyde. Treatment of the aldehyde with an amine in the presence of a reducing agent (e.g., NaCNBH$_3$) effects a reductive amination to provide compounds of Formula I. The intermediate IC' can also be condensed with hydroxylamine to give an oxime that may be reduced with a reducing agent such as $LiAlH_4$ to provide compound XXX.

SCHEME 9

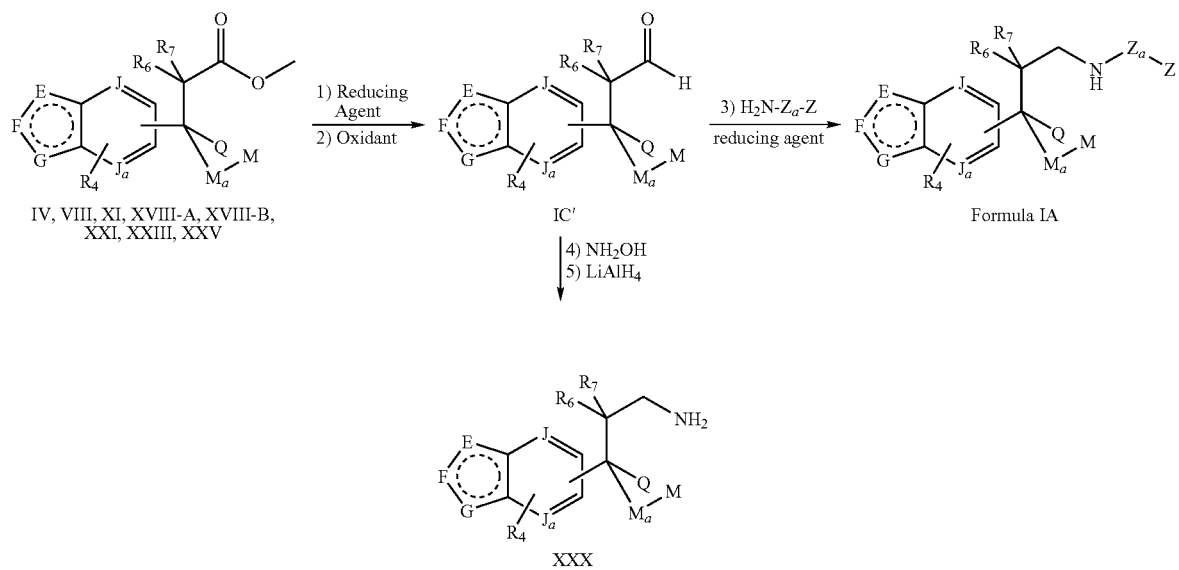

Alternatively, compound IC' can used to synthesize compounds that have substituents alpha to the amine (Scheme 10). Condensation of IC' with a sulfinamide yields a sulfinilimine that can be reacted with a nucleophile followed by hydrolysis to provide compound XXXII. Absolute stereochemistry can be controlled using a chiral sulfinamide using the method of Ellman (McMahon, J. P.; Ellman, J. A., *Org. Leu.*, 7:5393-5396 (2005); Cogan, D. A.; Liu, G.; Kim, K.; Backes, B. J.; Ellman, J. A., *J. Am. Chem. Soc.*, 120:8011 (1998); Kawano, Y.; Mukaiyama, T., *Chem. Lett.*, 34:894-895 2005). Converting the aldehyde XXXI to a ketone IC" followed by the same sulfinilimine sequence provides compound XXXIV that has both Rx and Ry substituents alpha to the amine

SCHEME 10

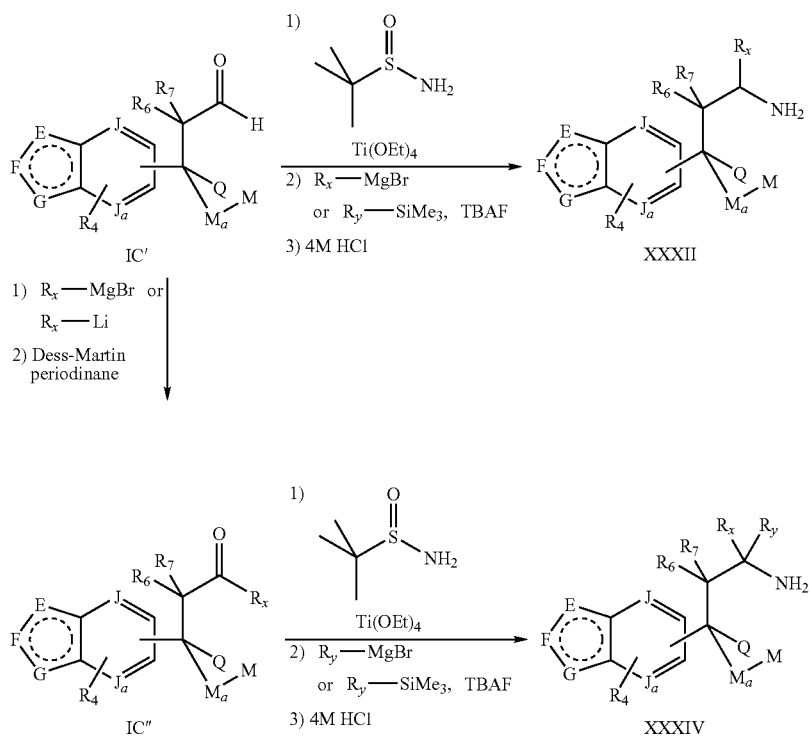

Scheme 11 illustrates a number of penultimate amines synthesized using the procedures detailed in the Schemes above that can be acylated using a variety of reagents to provide compounds of Formula IA.

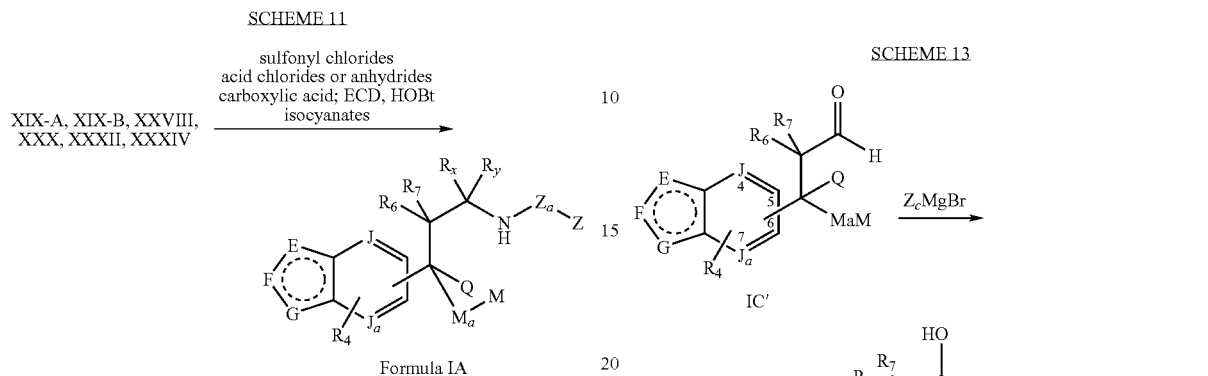

Scheme 12 shows an alternate route whereby compounds of Formula IA' bearing a urea side chain can be synthesized from starting amine XXX by reacting it with carbonyldiimidazole to form an intermediate isocyanate, XXXV, followed by reaction with an amine to provide the desired urea of Formula IA'.

Scheme 13 outlines general syntheses for a series of compounds of Formula I (that is, compounds of Formulae IB and IC). Compounds of Formula IB and IC are prepared by the addition of an organometallic compound such as the Grignard reagent $Z_c$—MgBr to the compound 1C' by one of the methods well known to those skilled in the art to give compound 1B'. Oxidation of the 1B' compound by one of the many methods for oxidizing secondary alcohols to ketones, such as using Dess-Martin periodinane, to afford compound IC''. Addition of Rx-Y, wherein Y is lithium, MgBr, or MgCl, or a trialkylsilyl group, such as $SiMe_3$ to the compound 1C'' provides compounds of Formula IB''. Treating Compound IB'' with CDI followed by an amine $Z_bNH_2$ (where $Z_b$ is alkylaminocarbonyl) affords the compound IB''' in accordance with the present invention.

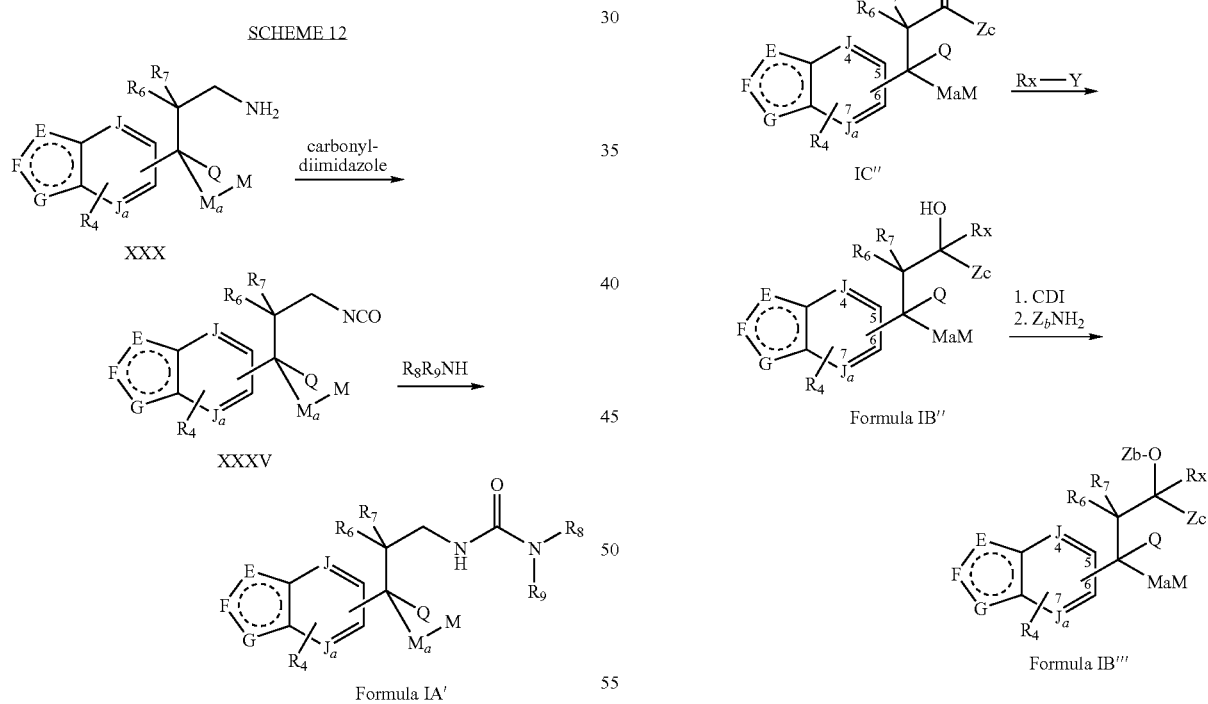

Protecting Groups for the Heterocyclic Core

It should be understood that protecting groups may be utilized as appropriate throughout synthetic Schemes 1 to 8 above. Common protecting groups for amine-containing heterocycles (where E, F, or G in Formula I are nitrogen, for example, indole, indazole, benzimidazole, and the like) are ureas, sulfonamides, carbamates, and alkyl groups (such as 4-methoxybenzyl). The judicious use of protecting groups is known to one skilled in the art and described in Greene et al., *Protecting Groups in Organic Synthesis, Vol. 3*.

DEFINITIONS

The following are definitions of terms used in this specification and appended claims. The initial definition provided for a group or term herein applies to that group or term throughout the specification and claims, individually or as part of another group, unless otherwise indicated.

The term "alkyl" alone or as part of another group refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$)hydroxyalkyl includes hydroxy, hydroxymethyl and hydroxyethyl.

"Alkyl" includes "unsubstituted" and "substituted alkyl" where the alkyl may be substituted with any of the substituents for substituted alkyl set out below.

The term "substituted alkyl" refers to an alkyl group as defined above having one, two, or three substituents independently selected from the group consisting of halo (e.g., trifluoromethyl), alkenyl, substituted alkenyl, alkynyl, nitro, cyano, oxo (=O), $OR_a$, $SR_a$, (=S), $-NR_aR_b$, $-N(alkyl)_3^+$, $-NR_aSO_2$, $-NR_aSO_2R_c$, $-SO_2R_c$, $-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}\text{alkylene})NR_aR_b$, $-C(=O)NR_a(SO_2)R_b$, $-CO_2(C_{1-4}\text{alkylene})NR_aR_b$, $-NR_aC(=O)R_b$, $-NR_aCO_2R_b$, $-NR_a(C_{1-4}\text{alkylene})CO_2R_b$, =N-OH, =N-O-alkyl, aryl, cycloalkyl, heterocyclo, and/or heteroaryl, wherein $R_a$ and $R_b$ are the same or different and are independently selected from hydrogen, alkyl, alkenyl, $CO_2H$, $CO_2$(alkyl), $C_{3-7}$cycloalkyl, phenyl, benzyl, phenylethyl, naphthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being the same or different and are independently selected from the group consisting of ($C_{1-6}$)alkyl, ($C_{2-6}$)alkenyl, hydroxy, halogen, cyano, nitro, $CF_3$, O($C_{1-6}$alkyl), $OCF_3$, C(=O)H, C(=O)($C_{1-6}$alkyl), $CO_2H$, $CO_2$($C_{1-6}$alkyl), $NHCO_2$($C_{1-6}$ alkyl), -S($C_{1-6}$alkyl), $-NH_2$, NH($C_{1-6}$alkyl), N($C_{1-6}$alkyl)$_2$, N($CH_3$)$_3^+$, $SO_2$($C_{1-6}$alkyl), $-NHC(=O)$alkyl, C(=O)($C_{1-4}$alkylene)$NH_2$, C(=O)($C_{1-4}$alkylene)NH(alkyl), C(=O)($C_{1-4}$alkylene)N($C_{1-4}$alkyl)$_2$, $C_{3-7}$cycloalkyl, phenyl, benzyl, phenylethyl, phenyloxy, benzyloxy, naphthyl, a four to seven membered heterocyclo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below and/or as defined for substituted alkyl.

One skilled in the field will understand that, when the designation "$CO_2$" is used herein, this is intended to refer to the group

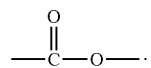

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl.

The term "alkenyl" (which includes unsubstituted or substituted alkenyl) alone or as part of another group refers to straight or branched chain hydrocarbon groups having 2 to 12 carbon atoms and at least one double bond. Alkenyl groups of 2 to 6 carbon atoms and having one double bond are most preferred.

The term "alkynyl" (which includes unsubstituted or substituted alkynyl) alone or as part of another group refers to straight or branched chain hydrocarbon groups having 2 to 12 carbon atoms and at least one triple bond. Alkynyl groups of 2 to 6 carbon atoms and having one triple bond are most preferred.

The term "alkylene" (which includes unsubstituted or substituted alkylene) alone or as part of another group refers to bivalent straight or branched chain hydrocarbon groups having 1 to 12 carbon atoms, preferably 1 to 8 carbon atoms, e.g., $\{-CH_2-\}_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "heteroalkylene" (which includes unsubstituted and "substituted heteroalkylene") alone or as part of another group is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from -O-, -S-, -S(=O)-, -SO$_2$-, -NH-, and -NHSO$_2$-. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as -S-(CH$_2$)$_{1-5}$NH-CH$_2$-, -O-(CH$_2$)$_{1-5}$S(=O)-CH$_2$-, -NHSO$_2$-CH$_2$-, -CH$_2$-NH-, and so forth. Preferably, a heteroalkylene does not have two adjacent atoms simultaneously selected from -O- and -S-. When a subscript is used with the term heteroalkylene, e.g., as in $C_{2-3}$heteroalkylene, the subscript refers to the number of carbon atoms in the group in addition to heteroatoms. Thus, for example, a $C_{1-2}$heteroalkylene may include groups such as -NH-CH$_2$-, -CH$_2$-NH-CH$_2$-, -CH$_2$-CH$_2$-NH-, -S-CH$_2$-, -CH$_2$-S-CH$_2$-, -O-CH$_2$-NH-CH$_2$-, CH$_2$-O-CH$_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen.

Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or $A_1$-Q-$A_2$-$R_h$, wherein $A_1$ is a bond, $C_{1-2}$alkylene, or $C_{2-3}$alkenylene; Q is a bond, —C(=O)—, —C(=O)NR$_d$—, —C(=S)NR$_d$—, —SO$_2$—, —SO$_2$NR$_d$—, —CO$_2$—, or —NR$_d$CO$_2$—; $A_2$ is a bond, $C_{1-3}$alkylene, $C_{2-3}$alkenylene, —$C_{1-4}$alkylene-NR$_d$—, —$C_{1-4}$alkylene-NR$_d$C(=O)—, —$C_{1-4}$alkylene-S—, —$C_{1-4}$alkylene-SO$_2$—, or —$C_{1-4}$alkylene-O—, wherein said $A_2$ alkylene groups are branched or straight chain and optionally substituted as defined herein for substituted alkylene; $R_h$ is hydrogen, alkyl, substituted alkyl, alkenyl, substituted alkenyl, aryl, heteroaryl, heterocyclo, or cycloalkyl; and $R_d$ is selected from hydrogen, alkyl, and substituted alkyl, as defined herein, provided, however, that for a substituted heteroalkylene $R_h$ is not hydrogen when $A_1$, Q and $A_2$ are each bonds. When $R_h$ is aryl, heteroaryl, cycloalkyl, or heterocyclo, these rings are, in turn, optionally substituted with one to three groups as defined below in the definitions for these terms.

The term "alkoxy" refers to an unsubstituted alkyl or substituted alkyl group as defined above having one or two oxygen atoms (—O—) in the alkyl chain. For example, the term "alkoxy" includes the groups —O—$C_{1-12}$alkyl, —($C_{1-6}$alkylene)-O—$C_{1-6}$alkyl, —($C_{1-4}$alkylene-O—$C_{1-4}$alkylene)-O—$C_{1-4}$alkyl, and so forth.

The term "thioalkyl" or "alkylthio" refers to an unsubstituted alkyl or substituted alkyl group as defined having one or two sulfur atoms in the alkyl chain. For example, the term "thioalkyl" or "alkylthio" includes the groups —S—$C_{1-12}$alkyl, —(S—$C_{1-6}$alkylene)-S—$C_{1-6}$alkyl, and so forth.

The terms "aminoalkyl" or "alkylamino" refer to an unsubstituted alkyl or substituted alkyl group as defined above having one or two nitrogen (—NR—) atoms in the alkyl chain. For example, the term "aminoalkyl" includes the groups —NR—$C_{1-12}$alkyl, —NR—$C_{1-6}$alkylene-NR—$C_{1-6}$alkyl, etc. (where R is preferably hydrogen but may include alkyl or substituted alkyl as defined above.) When a subscript is used with reference to an alkoxy, thioalkyl or aminoalkyl, the subscript refers to the number of carbon atoms that the group may contain in addition to heteroatoms. Thus, for example, monovalent $C_{1-2}$-aminoalkyl includes the groups —CH$_2$—NH$_2$, —NH—CH$_3$, —(CH$_2$)$_2$—NH$_2$, —NH—CH$_2$—CH$_3$, —CH$_2$—NH$_2$—CH$_3$, and —N—(CH$_3$)$_2$. A lower aminoalkyl comprises an aminoalkyl having one to four carbon atoms.

"Amino" refers to the group NH$_2$.

The term "substituted amino" alone or in part of another group refers to the group —NR$_a$R$_b$ (or other substituent groups other than R$_a$ or R$_b$ linked to an N atom) wherein the groups R$_a$ and R$_b$ and other substituent groups are defined above in the definition of substituted alkyl groups.

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—$C_{1-12}$alkyl, —O—$C_{1-6}$alkylene-O—$C_{1-6}$alkyl, —$C_{1-4}$alkylene-O—$C_{1-4}$alkylene-O—$C_{1-4}$alkyl, whereas a bivalent alkoxy includes groups such as —O—$C_{1-12}$alkylene-, —$C_{1-6}$alkylene-O—$C_{1-6}$alkylene-, —$C_{1-4}$alkylene-O—$C_{1-4}$alkylene-O—$C_{1-4}$alkylene-, and so forth.

The term "carbonyl" is intended to designate the group —C(O)—.

It should be understood that the selections for alkoxy, thioalkyl, and aminoalkyl will be made by one skilled in the field to provide stable compounds. Thus, for example, in compounds of formula I, when $R_5$, $R_6$, $R_7$ or $R_8$ is attached to a nitrogen atom (N*) of ring B and is selected from an alkoxy or alkylthio group, the alkoxy and alkylthio groups will have at least one carbon atom bonded directly to ring B (at N*), with the oxygen or sulfur atoms being at least one atom away from said nitrogen atom.

The term "acyl" alone or as part of another group refers to a carbonyl group linked to an organic radical, more particularly, the group C(=O)R$_e$, as well as the bivalent groups —C(=O) or —C(=O)R$_e$—, which are linked to organic radicals or a ring in compounds of formula I. The group R$_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, etc. Accordingly, in compounds of formula I, when it is recited that $R_1$ to $R_8$ can be "acyl," this is intended to encompass a selection for $R_1$ to $R_8$ of —C(=O)— and also the groups —C(=O)R$_e$— or —R$_e$C(=O)—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "alkoxycarbonyl" alone or as part of another group refers to a carboxy group

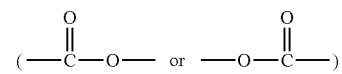

linked to an organic radical (CO$_2$R$_e$), as well as the bivalent groups —CO$_2$—, —CO$_2$R$_e$— which are linked to organic radicals in compounds of formula I, wherein R$_e$ is as defined above for acyl. The organic radical to which the carboxy group is attached may be monovalent (e.g., —CO$_2$-alkyl or —OC(=O)alkyl), or bivalent (e.g., —CO$_2$-alkylene, —OC(=O)alkylene, etc.). Accordingly, "alkoxycarbonyl," is intended to encompass the groups —CO$_2$R$_e$— or —R$_e$CO$_2$—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "amide" or "amidyl" alone or as part of another group refers to the group C(=O)NR$_a$R$_b$ (or other R groups other than R$_a$ or R$_b$ linked to an N atom), wherein the groups R$_a$ and R$_b$ are defined as recited above in the definition for substituted alkyl groups.

The term "sulfonyl" alone or as part of another group refers to a sulphoxide group linked to an organic radical in compounds of formula I, more particularly, the monovalent group S(O)$_{1-2}$—R$_e$, or the bivalent group —S(O)$_{1-2}$-linked to organic radicals in compounds of formula I. Accordingly, in compounds of formula I, "sulfonyl," is intended to encompass —S(=O)— or —SO$_2$— as well as the groups —S(=O)R$_e$—, —R$_e$S(=O)—, —SO$_2$R$_e$—, or —R$_e$SO$_2$—, wherein in this instance, the group R$_e$ will be selected from those recited above for acyl and alkoxycarbonyl groups.

The term "sulfonamidyl" alone or as part of another group refers to the group —S(O)$_2$NR$_a$R$_b$ (or other R groups other than R$_a$ or R$_b$ linked to an N atom), wherein R$_a$ and R$_b$ are as defined above for substituted alkyl groups. Additionally, the sulfonamidyl group may be bivalent, in which case one of the groups $R_a$ and $R_b$ will be a bond. Thus, in compounds of formula I, sulfonamidyl is intended to mean the group —S(O)$_2$ NR$_a$—.

The term "cycloalkyl" alone or as part of another group (includes unsubstituted cycloalkyl and substituted cycloalkyl) refers to fully saturated and partially unsaturated hydrocarbon rings of 3 to 15, preferably 3 to 10 carbon atoms. Accordingly, the term "cycloalkyl" is intended to include a cycloalkenyl (e.g., cyclohexenyl) ring. The term "cycloalkyl" includes monocyclic, bicyclic and tricyclic rings, such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3$$^+$, —NR$_a$SO$_2$, —NR$_a$SO$_2$R$_c$, —SO$_2$R$_c$—SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$, R$_b$ and R$_c$, are as defined above for substituted alkyl groups, and are also in turn optionally substituted as recited above in the definition for substituted alkyl groups. The term "cycloalkyl" also includes such rings having a second ring fused thereto (e.g., including benzo, cycloalkyl, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of (C$_{1-4}$alkyl, (C$_{2-4}$)alkenyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3$$^+$, SO$_2$(C$_{1-4}$alkyl), C(=O)(C$_{1-4}$alkylene)NH$_2$, C(=O)(C$_{1-4}$alkylene)NH(alkyl), and/or C(=O)(C$_{1-4}$alkylene)N(C$_{1-4}$alkyl)$_2$.

Accordingly, in compounds of formula (I), the term "cycloalkyl" includes cyclopropyl, cyclobutyl, cyclopentyl, cyclohexyl, cycloheptyl, cyclooctyl, etc., as well as the following ring systems,

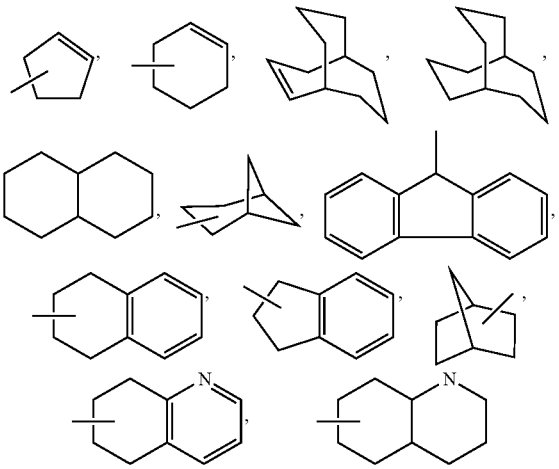

and the like, which optionally may be substituted at any available atoms of the ring(s). Preferred cycloalkyl groups include cyclopropyl, cyclobutyl, cyclopentyl, cyclohexyl,

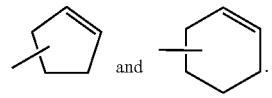

The term "halo" or "halogen" alone or as part of another group refers to chloro, bromo, fluoro and iodo.

The term "haloalkyl" alone or as part of another group means a substituted alkyl having one or more halo substituents. For example, "haloalkyl" includes mono, bi, and trifluoromethyl.

The term "haloalkoxy" alone or as part of another group means an alkoxy group having one or more halo substituents. For example, "haloalkoxy" includes OCF$_3$.

The term "aryl" alone or as part of another group (includes unsubstituted aryl and substituted aryl) refers to phenyl, biphenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, OR$_a$, SR$_a$, (=S), —NR$_a$R$_b$, —N(alkyl)$_3$$^+$, —NR$_a$SO$_2$, —NR$_a$SO$_2$R$_c$, —SO$_2$R$_c$—SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, aryl, cycloalkyl, heterocyclo, and/or heteroaryl, wherein R$_a$, R$_b$ and R$_c$ are as defined above for substituted alkyl groups, and are also in turn optionally substituted as recited above, or any of the substituents for alkyl set out hereinbefore. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to four, preferably one or two of (C$_{1-4}$)alkyl, (C$_{2-4}$)alkenyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3$$^+$, C(=O)NH$_2$, SO$_2$(C$_{1-4}$alkyl), C(=O)(C$_{1-4}$alkylene)NH$_2$, C(=O)(C$_{1-4}$alkylene)NH(alkyl), and/or C(=O)(C$_{1-4}$alkylene)N(C$_{1-4}$alkyl)$_2$.

Thus, examples of aryl groups include:

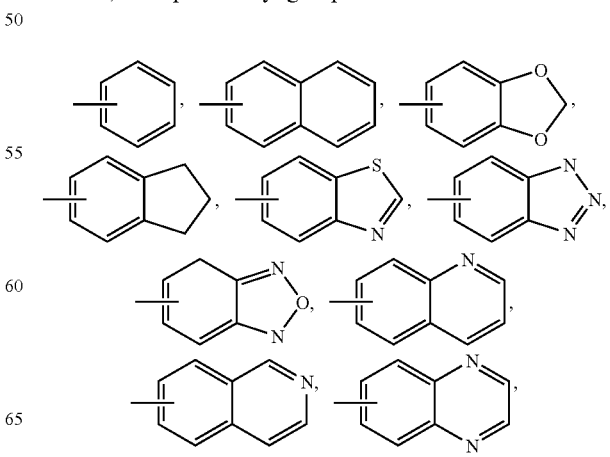

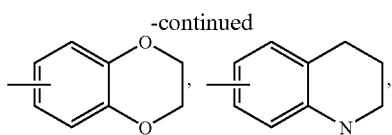

and the like, which optionally may be substituted at any available carbon or nitrogen atom. A preferred aryl group is optionally-substituted phenyl.

The terms "heterocyclo" or "heterocyclic" or "cycloheteroalkyl" alone or as part of another group refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N) (also referred to as cycloheteroalkyl or heterocycloalkyl). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), $-NR_aR_b$, $-N(alkyl)_3^+$, $-NR_aSO_2$, $-NR_aSO_2R_c$, $-SO_2R_c-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, $=N-OH$, $=N-O-alkyl$, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of $(C_{1-4})$alkyl, $(C_{2-4})$alkenyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, $-S(C_{1-4}alkyl)$, $-NH_2$, $NH(C_{1-4}alkyl)$, $N(C_{1-4}alkyl)_2$, $N(C_{1-4} alkyl)_3^+$, $SO_2(C_{1-4}alkyl)$, $C(=O)(C_{1-4}alkylene)NH_2$, $C(=O)(C_{1-4}alkylene)NH(alkyl)$, and/or $C(=O)(C_{1-4}alkylene)N(C_{1-4}alkyl)_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Preferred heterocyclo groups in compounds of formula (I) include

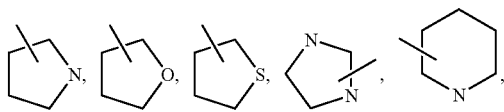

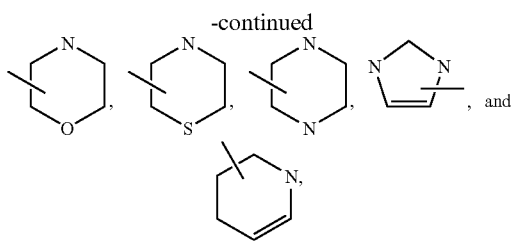

which optionally may be substituted.

The term "heteroaryl" alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), $-NR_aR_b$, $-N(alkyl)_3^+$, $-NR_aSO_2$, $-NR_aSO_2R_c$, $-SO_2R_c-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, oxo(=O), $-NR_aC(=O)R_b$, $-NR_aCO_2R_b$, $-NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of $(C_{1-4})$alkyl, $(C_{2-4})$alkenyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4} alkyl)$, $NHCO_2(C_{1-4}alkyl)$, $-S(C_{1-4}alkyl)$, $-NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, and/or $C(=O)(C_{1-4}alkylene)N(C_{1-4}alkyl)_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

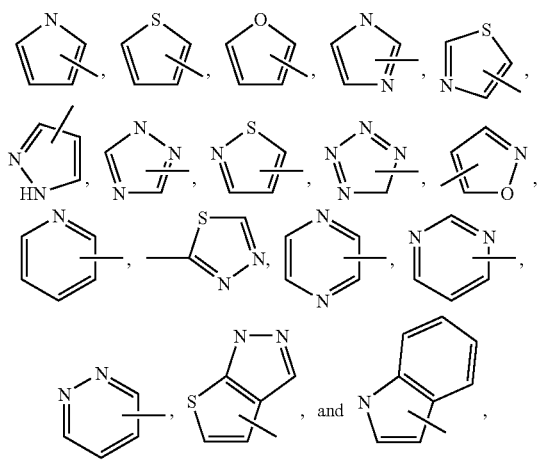

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Prodrug ester examples include the following groups: (1-alkanoyloxy)alkyl such as,

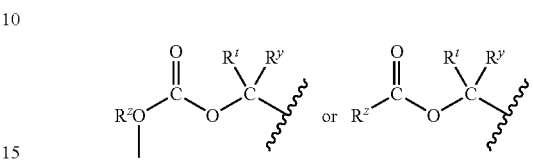

wherein $R^z$, $R^t$ and $R^y$ are H, alkyl, aryl or arylalkyl; however, $R^zO$ cannot be HO.

Examples of such prodrug esters include

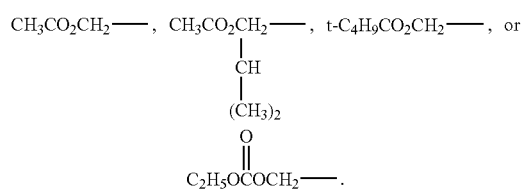

Other examples of suitable prodrug esters include

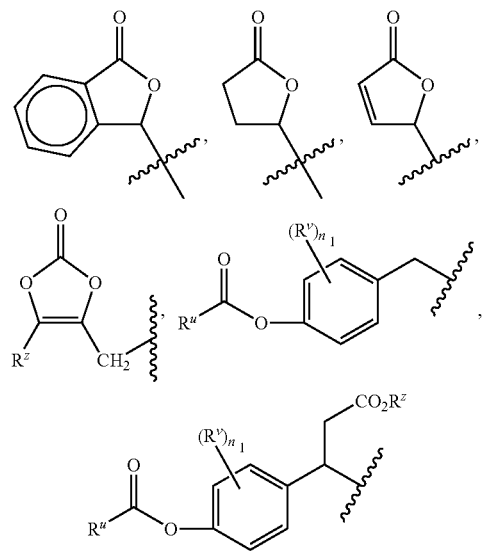

wherein $R^z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl or alkoxyl, and $n_1$ is 0, 1 or 2.

For further examples of prodrug derivatives, see:

a) *Design of Prodrugs*, edited by H. Bundgaard, (Elsevier, 1985) and *Methods in Enzymology*, 112:309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews,* 8:1-38 (1992).

The term "tautomer" refers to compounds of the formula (I) and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

The terms pharmaceutically acceptable "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methanesulfonic acid or p-toluenesulfonic acid.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The inventive compounds may be in the free or solvate (e.g., hydrate) form.

Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, anti-obesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula I of the invention include cyclosporins, for example cyclosporin A, mycophenolate, interferon-beta, deoxyspergolin, FK-506 or Ant.-IL-2.

The anti-cancer agents which may be optionally employed in combination with compounds of formula I of the invention include azathiprine, 5-fluorouracil, cyclophosphamide, cisplatin, methotrexate, thiotepa, carboplatin, and the like.

The anti-viral agents which may be optionally employed in combination with compounds of formula I of the invention include abacavir, aciclovir, ganciclovir, zidanocin, vidarabine, and the like.

The anti-inflammatory agents which may be optionally employed in combination with compounds of formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g., CD401g and CD8gp39), inhibitors, such as nuclear translocation inhibitors, of NF-kappa B function, such as deoxyspergualin (DSG).

The anti-fungal agents which may be optionally employed in combination with compounds of formula I of the invention include fluconazole, miconazole, amphotericin B, and the like.

The antibiotics which may be optionally employed in combination with compounds of formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula I of the invention include methotrexate, leflunomide, FK506 (tacrolimus, Prograf).

The hypolipidemic agent or lipid-lowering agent or lipid modulating agents which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

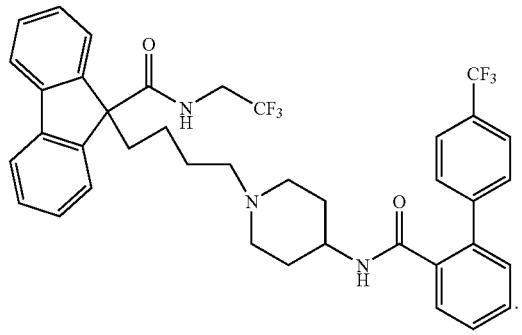

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl]pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propanephosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., J. Med. Chem., 31(10):1869-1871 (1988), including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2:1-40 (1996).

In addition, other squalene synthetase inhibitors suitable for use herein include the terpenoid pyrophosphates disclosed by Ortiz de Montellano, P. et al., J. Med. Chem., 20:243-249 (1977), the farnesyl diphosphate analog A and presqualene pyrophosphate (PSQ-PP) analogs as disclosed by Corey and Volante, J. Am. Chem. Soc., 98:1291-1293 (1976), phosphinylphosphonates reported by McClard, R. W. et al., J. Am. Chem. Soc., 109:5544 (1987), and cyclopropanes reported by Capson, T. L., Ph.D., dissertation, Dept. Med. Chem. U. of Utah, Abstract, Table of Contents, pp. 16, 17, 40-43, 48-51, Summary (June, 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future, 24:9-15 (1999), (Avasimibe); Nicolosi et al., "The ACAT inhibitor, C1-1011 is effective in the prevention and regression of aortic fatty streak area in hamsters", Atherosclerosis (Shannon, Irel.), 137(1):77-85 (1998), Ghiselli, G., "The pharmacological profile of FCE 27677: a novel ACAT inhibitor with potent hypolipidemic activity mediated by selective suppression of the hepatic secretion of ApoB100-containing lipoprotein", Cardiovasc. Drug Rev., 16(1):16-30 (1998); Smith, C., et al., "RP 73163: a bioavailable alkylsulfinyl-diphenylimidazole ACAT inhibitor", Bioorg. Med. Chem. Lett., 6(1):47-50 (1996); Krause et al., "ACAT inhibitors: physiologic mechanisms for hypolipidemic and anti-atherosclerotic activities in experimental animals", Inflammation: Mediators Pathways, Publisher: CRC, Boca Raton, Fla., Editor(s): Ruffolo, Robert R., Jr., Hollinger, Mannfred A., pp. 173-198 (1995); Sliskovic et al., "ACAT inhibitors: potential anti-atherosclerotic agents", Curr. Med. Chem., 1(3):204-225 (1994); Stout et al., "Inhibitors of acyl-CoA:cholesterol O-acyl transferase (ACAT) as hypocholesterolemic agents. 6. The first water-soluble ACAT inhibitor with lipid-regulating activity Inhibitors of acyl-CoA:cholesterol acyltransferase (ACAT). 7. Development of a series of substituted N-phenyl-N'-[(1-phenylcyclopentyl) methyl]ureas with enhanced hypocholesterolemic activity", Chemtracts: Org. Chem. 8(6):359-362 (1995), or TS-962 (acetamide, N-[2,6-bis(1-methylethyl)phenyl]-2-(tetradecylthio)-) (Taisho Pharmaceutical Co. Ltd).

The hypolipidemic agent may be an upregulator of LD2 receptor activity such as MD-700 (1(3H)-isobenzofuranone, 3-(13-hydroxy-10-oxotetradecyl)-5,7-dimethoxy) (Taisho Pharmaceutical Co. Ltd) and LY295427 (cholestan-3-ol, 4-(2-propenyl)-, (3a, 4a, 5a)-) (Eli Lilly).

The hypolipidemic agent may be a cholesterol absorption inhibitor preferably Schering-Plough's ezetimibe (SCH58235) and SCH48461 as well as those disclosed in *Atherosclerosis*, 115:45-63 (1995) and *J. Med. Chem.* 41: 973 (1998).

The hypolipidemic agent may be an ileal $Na^+$/bile acid cotransporter inhibitor such as disclosed in *Drugs of the Future*, 24:425-430 (1999).

The lipid-modulating agent may be a cholesteryl ester transfer protein (CETP) inhibitor such as Pfizer's CP 529,414 (torcetrapib) (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference.

The amounts and dosages employed will be as indicated in the Physicians' Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physicians' Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al., "Attenuation of diet-induced atherosclerosis in rabbits with a highly selective 15-lipoxygenase inhibitor lacking significant antioxidant properties", *Brit. J. Pharmacology*, 120:1199-1206 (1997), and Cornicelli et al., "15-Lipoxygenase and its Inhibition: A Novel Therapeutic Target for Vascular Disease", *Current Pharmaceutical Design*, 5:11-20 (1999).

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1, 2, 3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Wellcome's GL-262570 (farglitazar), englitazone (CP-68722, Pfizer) or darglitazone (CP-86325, Pfizer), isaglitazone (MIT/J&J), JTT-501 (reglitazar) (JPNT/P&U), L-895645 (Merck), R-119702 (rivoglitazone) (Sankyo/WL), N,N-2344 (balaglitazone) (Dr. Reddy/NN), or YM-440 ((Z)-1,4-bis-4[(3,5-dioxo-1,2,4-oxadiazolidin-2-yl-methyl)]phenoxybut-2-ene) (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (exenatide) (Amylin) and LY-315902 (8-37-glucagon-like peptide I (human), N-[3-(1H-imidazol-4-yl)-1-oxopropyl]-26-L-arginine-34-[N6-(1-oxooctyl)-L-lysine]-) (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physicians' Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physicians' Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-HO39242 (tesaglitazar) (Astra/Zeneca), GW-409544 (Glaxo-Wellcome), KRP297 (benzamide, 5-[(2,4-dioxo-5-thiazolidinyl)methyl]-2-methoxy-N-[[4-(trifluoromethyl)phenyl]methyl]- (Kyorin Merck) as well as those disclosed by Murakami et al., "A Novel Insulin Sensitizer Acts As a Coligand for Peroxisome Proliferation-Activated Receptor Alpha (PPAR alpha) and PPAR gamma Effect on PPAR alpha Activation on Abnormal Lipid Metabolism in Liver of Zucker Fatty Rats", *Diabetes*, 47:1841-1847 (1998).

The antidiabetic agent may be an SGLT2 inhibitor such as disclosed in U.S. application Ser. No. 09/679,027, filed Oct. 4, 2000, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000, employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al., *Biochemistry*, 38(36):11597-11603 (1999), TSL-225 (tryptophyl-1,2,3,4-tetrahydro-isoquinoline-3-carboxylic acid (disclosed by Yamada et al., *Bioorg. & Med. Chem. Lett.*, 8:1537-1540 (1998), 2-cyanopyrrolidides and 4-cyanopyrrolidides as disclosed by Ashworth et al., *Bioorg. & Med. Chem. Lett.*, 6(22):1163-1166 and 2745-2748 (1996) employing dosages as set out in the above references.

The meglitinide which may optionally be employed in combination with the compound of formula I of the invention may be repaglinide, nateglinide (Novartis) or KAD1229 (mitiglinide) (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (rafabegron) (Takeda/Dainippon), L750355 (benzenesulfonamide, N-[4-[2-[[(2S)-3-[(6-amino-3-pyridinyl)oxy]-2-hydroxypropyl]amino]ethyl]phenyl]-4-(1-methylethyl)-) (Merck), or CP331684 (4-[2-[[2-(6-aminopyridin-3-yl)-2(R)-hydroxyethyl]-amino]ethoxy]phenyl]acetic acid) (Pfizer) or other known beta 3 agonists as disclosed in U.S. Pat. Nos. 5,541,204, 5,770,615, 5,491,134, 5,776,983 and 5,488,064, with AJ9677, L750,355 (benzenesulfonamide, N-[4-[2-[[(2S)-3-[(6-amino-3-pyridinyl)oxy]-2-hydroxypropyl]amino]ethyl]phenyl]-4-(1-methylethyl)-) and CP331684 being preferred.

The lipase inhibitor which may be optionally employed in combination with a compound of formula I may be orlistat or ATL-962 (Alizyme), with orlistat being preferred.

The serotonin (and dopamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), WO00/039077 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol., 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol., 40:373 (1986); Ciba-Geigy's CGS 14824 (3-([1-ethoxy-carbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res., 39:671, 40:543 (1986); ramipril (Hoechst) disclosed in Euro. Patent No. 79-022 and Curr. Ther. Res., 40:74 (1986); Ru 44570 (Hoechst) disclosed in Arzneimittelforschung, 34:1254 (1985), cilazapril (Hoffman-LaRoche) disclosed in J. Cardiovasc. Pharmacol., 9:39 (1987); R 31-2201 (Hoffman-LaRoche) disclosed in FEBS Lett., 165: 201 (1984); lisinopril (Merck), indalapril (delapril) disclosed in U.S. Pat. No. 4,385,051; indolapril (Schering) disclosed in J. Cardiovasc. Pharmacol., 5:643, 655 (1983), spirapril (Schering) disclosed in Acta. Pharmacol. Toxicol., 59(Supp. 5):173 (1986); perindopril (Servier) disclosed in Eur. J. Clin. Pharmacol., 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl) disclosed in Pharmacologist, 26:243, 266 (1984), WY-44221 (Wyeth) disclosed in J. Med. Chem., 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366, 973, 5,225,401, 4,722,810, 5,223,516, 4,749,688, 5,552,397, 5,504,080, 5,612,359, 5,525,723, European Patent Application 0599444, 0481522, 0599444, 0595610, European Patent Application 0534363A2, 534396 and 534492, and European Patent Application 0629627A2.

Preferred are those NEP/ACE inhibitors and dosages thereof which are designated as preferred in the above patents/applications which U.S. patents are incorporated herein by reference; most preferred are omapatrilat ([S—(R*,R*)]-hexahydro-6-[(2-mercapto-1-oxo-3-phenylpropyl)amino]-2, 2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physicians' Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl)(Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®).

Dosages employed for the above drugs will be as set out in the Physicians' Desk Reference.

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$- and $\gamma$-cyclodextrin, or chemically modified derivatives such as hydroxyalkylcyclodextrins, including 2- and 3-hydroxypropyl-$\beta$-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of the examples are inhibitors of AP-1 activity and/or compete with known ligands of the glucorcorticoid receptor.

Compounds of the invention, including the compounds described in the examples hereof, have been tested in at least one of the assays described below and have glucocorticoid receptor (GR)/Dexamethasone (Dex) inhibitory activity and/or AP-1 inhibitory activity.

Assays

GR Binding Assays
Glucocorticoid Receptor Binding Assay (I)

In order to assess the affinity of test compounds for the human glucocorticoid receptor, a commercially available kit was used (Glucocorticoid Receptor Competitor Assay Kit, Invitrogen Part # 2893). Briefly, purified human recombinant full-length glucocorticoid receptor (2 nM) was mixed with fluorescently labeled glucocorticoid (1 nM Fluormone GS Red) in the presence or absence of test compound. After two hour incubation at room temperature in the dark, the fluorescence polarization (FP) of the samples was measured. The FP of a mixture of receptor, fluorescent probe (i.e. Fluormone GS Red) and 5 µM dexamethasone represented background fluorescence or 100% inhibition, whereas, the FP of the mixture without dexamethasone (but in the presence of vehicle) was taken to be 100% binding. The percentage inhibition of test compounds were then compared to the sample with 5 µM dexamethasone and expressed as % relative binding activity with dexamethasone being 100% and no inhibition being 0%. Test compounds were analyzed in the concentration range from 8.5E-05 µM to 5 µM.

Glucocorticoid Receptor Binding Assay (II)

In order to measure the binding of compounds on the glucocorticoid receptor a commercially available kit was used (Glucocorticoid receptor competitor assay kit, PanVera Co., Madison, Wis., P2816). Briefly, a cell lysate containing recombinantly expressed human full-length glucocorticoid receptor was mixed with a fluorescently labeled glucocorticoid (1 nM Fluormone GS1) in the presence or absence of test compound. After one hour at room temperature, the fluorescence polarization (FP) of the samples were measured. The FP of a mixture of receptor, fluorescent probe (i.e. Fluormone GS1) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition being 0%. Test molecules were analyzed in the concentration range from 2.4 nM to 40 microMolar.

Cellular Transrepressional Assay

To measure the ability of test molecules to inhibit AP-1 induced transcriptional activity an A549 cell was utilized which was stably transfected with a plasmid containing 7×AP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 µM. EC50s were determined by using standard curve fitting methods such as Excel fit (Microsoft Co.). An EC50 is the test molecule concentration at which there is a 50% repression of the maximal inhibition of transcription, i.e. a 50% reduction of AP-1 activity. In the absence of an EC50 the maximum % inhibition recorded is the inhibition of AP-1 at a compound concentration of 10 micromolar.

Other reporters and cell lines also may be used in a cellular transrepressional assay. A similar assay is performed in which NF-κB activity is measured. A plasmid containing NF-κB DNA binding sites is used, such as pNF-kB-Luc, (Stratagene, LaJolla Calif.), and PMA or another stimulus, such as TNF-α or lipopolysaccharide, is used to activate the NF-κB pathway. NF-κB assays similar to that described in Yamamoto, K. et al., *J. Biol. Chem.*, 270(52):31315-31320 (Dec. 29, 1995) may be used.

The cellular transrepressional assays described above may be used to measure transrepression by any NHR. One of skill in the art will understand that assays may require the addition of components, such as a stimulus (e.g., PMA, lipopolysaccharide, TNF-α, etc.) which will induce transcription mediated by AP-1 or NF-κB.

Additionally, AR mediated transrepression may be measured by the assay described in Palvimo, J. J. et al., *J. Biol. Chem.*, 271(39):24151-24156 (Sep. 27, 1996), and PR mediated transrepression may be measured by the assay described in Kalkhoven, E. et al., *J. Biol. Chem.*, 271(11):6217-6224 (Mar. 15, 1996).

ABBREVIATIONS

The following abbreviations are employed in the following Preparations and Examples:
ACN=acetonitrile
Ph=phenyl
Bn=benzyl
t-Bu=tertiary butyl
Me=methyl
Et=ethyl
TMS=trimethylsilyl
TMSN$_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
Et$_2$O=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane
HMPA=hexamethyl phosphoric triamide
HOAc or AcOH=acetic acid
TFA=trifluoroacetic acid
TFAA=trifluoroacetic anhydride
i-Pr$_2$NEt=diisopropylethylamine Et₃N=triethylamine
NMM=N-methyl morpholine
DMAP=4-dimethylaminopyridine
NaBH$_4$=sodium borohydride
NaBH(OAc)$_3$=sodium triacetoxyborohydride
DIBALH=diisobutyl aluminum hydride
LAH or LiAlH$_4$=lithium aluminum hydride
n-BuLi=n-butyllithium
LDA=lithium diisopropylamide
Pd/C=palladium on carbon
PtO$_2$=platinum oxide
KOH=potassium hydroxide
NaOH=sodium hydroxide
LiOH=lithium hydroxide
K$_2$CO$_3$=potassium carbonate
NaHCO$_3$=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H$_2$O=1-hydroxybenzotriazole hydrate
HOAT=1-Hydroxy-7-azabenzotriazole
BOP reagent=benzotriazol-1-yloxy-tris(dimethylamino)phosphonium hexafluorophosphate
NaN(TMS)$_2$=sodium hexamethyldisilazide or sodium bis(trimethylsilyl)amide
Ph$_3$P=triphenylphosphine
Pd(OAc)$_2$=Palladium acetate
(Ph$_3$P)$_4$Pd°=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
N$_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
rt or RT=room temperature
sat or sat'd=saturated
aq.=aqueous
TLC=thin layer chromatography
HPLC=high performance liquid chromatography
Reverse phase HPLC=reverse phase high performance liquid chromatography, using a YMC ODS S5 column and a binary solvent A/solvent B eluents
Solvent A=10% MeOH-90% H$_2$O-0.1% TFA
Solvent B=90% MeOH-10% H$_2$O-0.1% TFA; or
Solvent A=H$_2$O containing 0.1% TFA
Solvent B=ACN containing 0.1% TFA
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point

EXAMPLES

The following Examples illustrate embodiments of the inventive compounds and starting materials, and are not intended to limit the scope of the claims.

Preparations

The preparations set out below are for the synthesis of reagents that were not obtained from commercial sources and were employed for the preparation of compounds of formula I of the invention. All chiral compounds in the tables and schemes are racemic unless specified otherwise.

Reverse-phase preparative high performance liquid chromatography ("HPLC") was performed with Shimadzu 8A liquid chromatographs using YMC S5 ODS columns (20×100, 20×250 or 30×250 millimeter ("mm")). Gradient elution was performed with methanol ("MeOH")/water mixtures in the presence of 0.1% trifluoroacetic acid ("TFA").

Analytical HPLC Method Employed in Characterization of Examples

Analytical HPLC was performed on Shimadzu LC10AS liquid chromatographs using the following methods:
Method A (Used in all Cases, Unless Otherwise Indicated):
  Linear gradient of 0 to 100% solvent B over 4 minutes ("min"), with 1 minute ("min") hold at 100% B.
  Ultraviolet ("UV") visualization at 220 nanometers ("nm")
  Column: YMC S5 ODS Ballistic 4.6×50 mm
  Flow rate: 4 milliliters ("mL")/min
  Solvent A: 0.2% phosphoric acid, 90% water, 10% methanol
  Solvent B: 0.2% phosphoric acid, 90% methanol, 10% water
Method B:
Column: Phenomenex Luna C18(2), 4.6×50 mm×5 um
Mobile Phase: (A) 10:90 methanol:water; (B) 90:10 methanol:water
Buffer: 0.1% TFA
Gradient Range: 0-100% B
Gradient Time: 4 min
Flow Rate: 4 mL/min
Analysis Time: 5 min
Detection:
Detector 1: UV at 220 nm
Detector 2: MS (ESI+)
Detector 3: ELSD
Purification of Final Compounds of Formula I All of the examples that are described below that contain one or more chiral centers can be resolved using standard or chiral HPLC chromatography. Purification of diastereomers or regioisomers was performed using HPLC (Phenomenex Luna column: 3×25 cm 5 mM C18; solvent: water (containing 0.5% TFA) with increasing acetonitrile (containing 0.5% TFA) gradients over 25 min; flow rate: 40 mL/min; uv detection at 215 nM). Another HPLC method makes use of a YMC S5 CombiScreen column: 4.6×50 mm C18; solvent: 10-90% aqueous methanol over 4 minutes containing 0.2% phosphoric acid; flow rate: 4 mL/min; uv detection at 220 nM.

Chiral separation of enantiomers was performed using preparative Chiracel AD, OJ, or AS columns and isocratic mobile phases of EtOH or MeOH mixed with heptane. Alternatively, the same Chiracel columns could be run using SFC methods with mobile phases such as CO$_2$, MeOH, and diethylamine. Note that enantiomers may be separated after the final stage of synthesis or earlier at any intermediate chiral precursor in the synthetic route and then taken to the end of the synthetic sequence enantiomerically pure.

Synthetic Intermediate I 3-(1-(4-Fluorophenyl)-1H-indazol-5-yl)-2,2-dimethyl-3-phenylpopan-1-amine

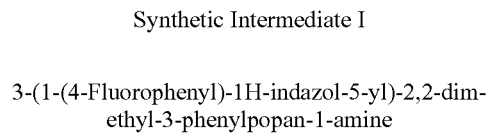

SCHEME A

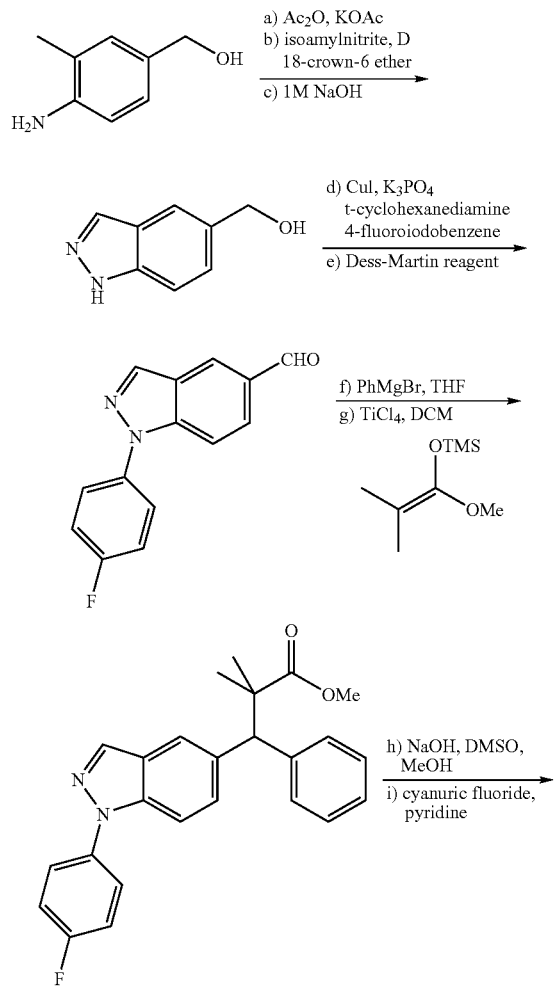

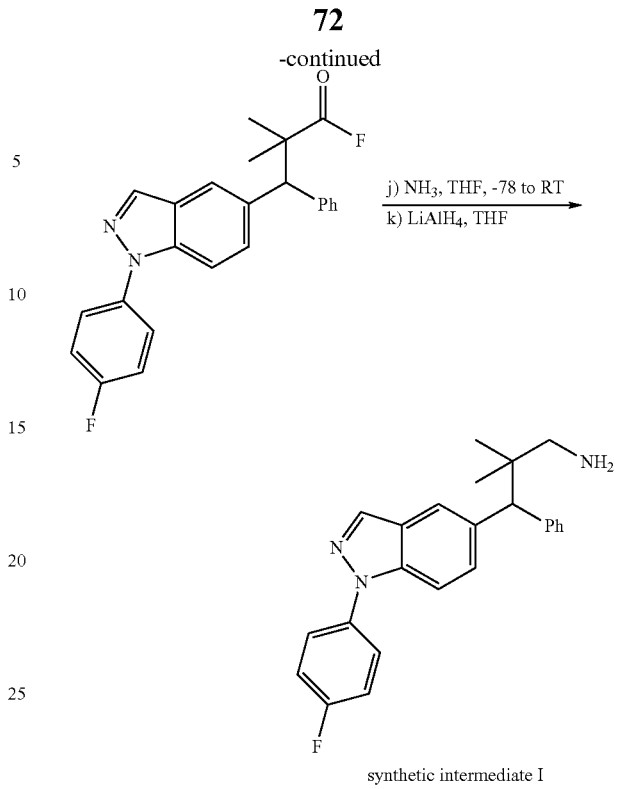

synthetic intermediate I (a) Following the general procedure of Sun et al. (*J. Org. Chem.*, 62:5627-5629 (1997)), 4-amino-3-methyl-benzyl alcohol (36.8 g, 269 mmol) was dissolved in dry chloroform (1 L) followed by potassium acetate (53 g, 540 mmol), and acetic anhydride (83 g, 810 mmol). After 2 h, the reaction was refluxed for 3 h and then cooled to rt and stirred overnight.

(b) The next day, 18-crown-6 ether (3.6 g, 13.5 mmol) was added followed by isoamyl nitrite (71.3 g, 608 mmol). The reaction was refluxed for 20 h, cooled to rt, washed with sat NaHCO$_3$, and the organic layer was dried over MgSO$_4$, filtered, and concentrated in vacuo. The crude oil was passed through a SiO$_2$ plug first with 5% EtOAc in hexanes, then 20% EtOAc in hexanes and concentrated. The residue was triturated with Et$_2$O/hexane to obtain 23.3 g of solid, bis-acetylated product. The supernatant was concentrated and the titration procedure repeated twice to give an additional 12.2 g. Total yield: 35.5 g (57% yield). MS found: (M+H)$^+$=233.

(c) The solid was dissolved in MeOH (350 mL) and treated with 1 M NaOH (150 mL). After stirring overnight, the MeOH was removed in vacuo, the residue acidified with conc HCl to pH 4-5 and extracted with EtOAc×3. The organic layer was dried with MgSO$_4$, filtered, concentrated in vacuo to give 20.1 g (90%) of (1H-indazol-5-yl)methanol. MS found: (M+H)$^+$=149.

(d) (1H-Indazol-5-yl)methanol (2.7 g, 18.2 mmol) was dissolved in 20 mL dry dioxane in a stainless steel pressure tube. Trans-1,2-cyclohexanediamine (1.1 mL, 9.12 mmol) was added followed by CuI (174 mg, 0.91 mmol) and then K$_3$PO$_4$ (6.97 g, 32.8 mmol). After the addition of 4-fluoro-1-iodobenzene (2.1 mL, 18.2 mmol), the reactor was sealed and heated at 100° C. for 24 h. The reactor was cooled and the contents were taken up in EtOAc, filtered through a SiO$_2$ plug with EtOAc and concentrated in vacuo. The crude product was chromatographed using 31:1 EtOAc/hexanes to give 4.25 g (96% yield) of a pale yellow oil (1-(4-fluorophenyl)-1H-indazol-5-yl)methanol that solidified on standing. MS found: (M+H)$^+$=243.

(e) (1-(4-Fluorophenyl)-1H-indazol-5-yl)methanol (2.46 g, 10.2 mmol) was dissolved in 80 mL DCM and treated with commercially available Dess-Martin periodinane (4.3 g, 10.2 mmol). The reaction was complete in 2 h and was filtered through a plug of $SiO_2$ using DCM/hexane (3:1) and concentrated to give 2.47 g (100%) of 1-(4-fluorophenyl)-1H-indazol-5-carboxaldehyde. MS found: $(M+H)^+=241$.

(f) 1-(4-Fluorophenyl)-1H-indazol-5-carboxaldehyde (2.47 g, 10.2 mmol) was dissolved in 25 mL THF, cooled in a 0° C. ice bath, and treated with PhMgBr (4.6 mL of 1.0 M in THF, 4.58 mmol). After 1 h, the reaction was quenched with sat. $NH_4Cl$ and extracted with EtOAc×3. The organic layers were dried over $MgSO_4$, filtered, and concentrated to give 3.2 g (100%) of product (1-(4-fluorophenyl)-1H-indazol-5-yl)(phenyl)methanol. MS found: $(M+H)^+=319$.

(g) (1-(4-Fluorophenyl)-1H-indazol-5-yl)(phenyl)methanol (16.0 g, 50 mmol) was dissolved in 400 mL of dry THF and $TiCl_4$ (60 mL of 1.0 M DCM solution, 60 mmol) was added portionwise and then stirred 30 min. The flask was put on a rotary evaporator until the THF began to distill to degas the HCl and then the reaction was treated with 1-methoxy-2-methyl-1-(trimethylsiloxy)propene (17.4 g, 100 mmol). The reaction was quenched with aqueous sodium bicarbonate and extracted 2× EtOAc, the organic layers dried over $MgSO_4$, filtered, concentrated, and then chromatographed using DCM to give 16.2 g (81% yield) of methyl 3-(1-(4-fluorophenyl)-1H-indazol-5-yl)-2,2-dimethyl-3-phenylpropanoate. MS found: $(M+H)^+=403$.

(h) Methyl 3-(1-(4-fluorophenyl)-1H-indazol-5-yl)-2,2-dimethyl-3-phenylpropanoate (16.2 g, 40.2 mmol) was heated to 100° C. overnight in a mixture of 2 M NaOH/MeOH/DMSO (1:1:1). The next day, the reaction was cooled, acidified to pH 5 with HCl and extracted 2× EtOAc. The organic layers were washed with water×2, dried over $MgSO_4$, filtered, and concentrated in vacuo to give 15.4 g (99% yield) of acid 3-(1-(4-fluorophenyl)-1H-indazol-5-yl)-2,2-dimethyl-3-phenylpropanoic acid. MS found: $(M+H)^+=389$.

(i)(j) To a solution of 3-(1-(4-fluorophenyl)-1H-indazol-5-yl)-2,2-dimethyl-3-phenyl-propanoic acid) (16 mmol) and pyridine (1.5 mL, 18.5 mmol) in 300 mL of $CH_2Cl_2$ was added cyanuric fluoride (1.6 mL, 18.8 mmol). The reaction was stirred for 1 hr, then quenched with 1N HCl and extracted with 2×$CH_2Cl_2$. The $CH_2Cl_2$ extracts were dried over $MgSO_4$, filtered, and concentrated by rotary evaporator to give the corresponding crude acid fluoride. This intermediate was characterized using MS and $^1$H-NMR. To a solution of 3-(1-(4-fluorophenyl)-1H-indazol-5-yl)-2,2-dimethyl-3-phenylpropanoyl fluoride (1.65 g, 4.23 mmol) in anhydrous THF (30 mL) at −78° C. was bubbled $NH_3$ (g) for 10 minutes. The reaction mixture was sealed and stirred at −78° C. for 15 min and at rt for 1 hr. Water (100 mL) was added, the reaction mixture was extracted with ethyl acetate (100 mL), dried ($Na_2SO_4$), and concentrated to give 1.62 g (100% yield) of 3-(1-(4-fluorophenyl)-1H-indazol-5-yl)-2,2-dimethyl-3-phenylpropanamide, the NMR spectrum of which was consistent with the desired structure.

(k) To a stirred solution of 3-(1-(4-fluorophenyl)-1H-indazol-5-yl)-2,2-dimethyl-3-phenylpropanamide (1.62 g, 4.23 mmol) in anhydrous THF (100 mL) was added 1.0M lithium aluminum hydride in diethyl ether (8.0 mL, 8.0 mmol) portionwise at RT under nitrogen. After stirring at RT for 24 hr, the mixture was carefully quenched with MeOH, poured into a 1N sodium hydroxide solution (100 mL), extracted with ethyl acetate (2×100 mL), dried ($Na_2SO_4$) and concentrated to give 1.3 g (82% yield) of 3-(1-(4-fluorophenyl)-1H-indazol-5-yl)-2,2-dimethyl-3-phenylpropan-1-amine (Synthetic Intermediate I) as a yellow oil, the NMR spectrum of which was consistent with the desired structure.

Scheme B illustrates the conversion of amine precursors (e.g., Synthetic Intermediates I-IV) into compounds of Formula I using the methods of General Coupling Methods A, B, or C.

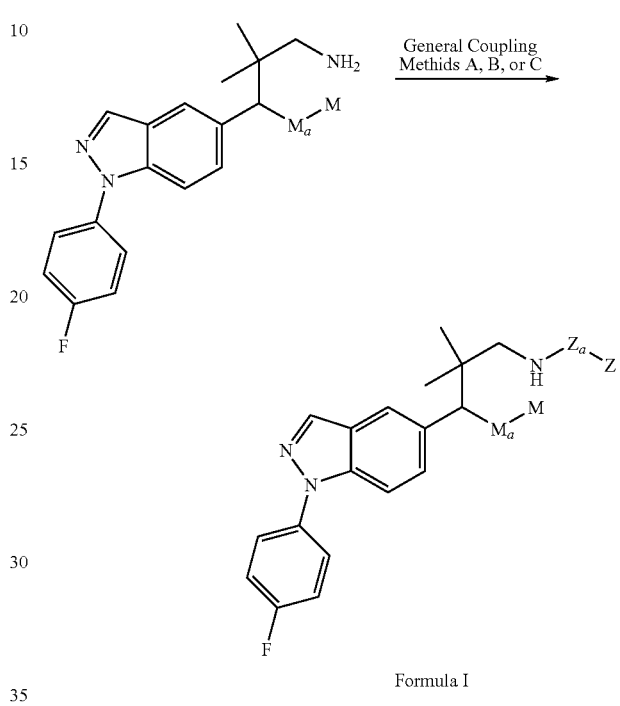

Formula I

General Coupling Method A

To a solution of $R_8$—$CO_2H$ (0.15 mmol) in DMF (1-2 mL) is added hydroxybenzotriazole (31 mg, 0.23 mmol), triethylamine (0.3 mmol), and N-(3-dimethylaminopropyl)-N'-ethylcarbodiimide (43 mg, 0.23 mmol). After stirring for 10 min, Synthetic Intermediate I to IV (e.g., 3-(1-(4-fluorophenyl)-1H-indazol-5-yl)-2,2-dimethyl-3-phenylpropan-1-amine) (0.23 mmol) is added and the reaction is stirred at rt for 3-24 h. The reaction is cooled and the reaction purified by HPLC. Products were identified by MS and showed consistent $^1$H-NMR spectra.

General Coupling Method B

To a solution of Synthetic Intermediate I to IV (e.g., 3-(1-(4-fluorophenyl)-1H-indazol-5-yl)-2,2-dimethyl-3-phenyl-propan-1-amine) (0.12 mmol) and triethylamine (50 μL, 0.36 mmol) in 2 mL of $CH_2Cl_2$ was added anhydride, acid chloride, sulfonyl chloride, or isocyanate (0.36 mmol). The reaction was stirred for 1 hr, then concentrated by rotary evaporator. The final products are purified using HPLC and the final products were identified by MS and showed consistent $^1$H-NMR spectra.

General Coupling Method C

Synthetic Intermediate I to IV (e.g., 3-(1-(4-fluorophenyl)-1H-indazol-5-yl)-2,2,5-trimethylhexan-1-amine) (30 mg, 0.08 mmol) was dissolved in THF (0.5 mL) and to this was added CDI (19.4 mg, 0.12 mmol) at RT. The mixture was stirred at RT for 2 h to form an intermediate isocyanate. $R_8(R_9)NH$ (31 mg, 0.4 mmol) was added to the reaction and the mixture was heated to 50° C. for 6 h. The reaction was concentrated in vacuo, the residue was dissolved in methanol (1.0 mL) and purified using preparative HPLC(YMC VP ODS 20×100 mm, 10 min. run, solvent A: 10% MeOH: 90%

$H_2O$: 0.1% TFA, solvent B: 90% MeOH, 10% $H_2O$, 0.1% TFA). The desired fractions were collected and concentrated to yield the desired compounds of Formula I shown below in Table 2. Final compounds were identified by MS and showed consistent $^1$H-NMR spectra.

Examples 1 to 24

The compounds in Table 1 were synthesized via the transformation shown in Scheme B using Synthetic Intermediate I and the acylating agent indicated in the table.

TABLE 1

| Ex. | Name | Product Structure | (M + H)+ | Alkylating Agent | Coupling Method |
|---|---|---|---|---|---|
| 1 | (S)-N-(3-(1-(4-fluorophenyl)-1H-indazol-5-yl)-2,2-dimethyl-3-phenylpropyl)-3,3-dimethylbutanamide | | 472 | t-butylacetic acid | A |
| 2 | (S)-N-(3-(1-(4-fluorophenyl)-1H-indazol-5-yl)-2,2-dimethyl-3-phenylpropyl)-4-methylpentanamide | | 472 | 4-methyl-pentanoic acid | A |
| 3 | (S)-N-(3-(1-(4-fluorophenyl)-1H-indazol-5-yl)-2,2-dimethyl-3-phenylpropyl)-2-phenylacetamide | | 492 | phenylacetic acid | A |

TABLE 1-continued

| Ex. | Name | Product Structure | (M + H)+ | Alkylating Agent | Coupling Method |
|---|---|---|---|---|---|
| 4 | (S)-N-(3-(1-(4-fluorophenyl)-1H-indazol-5-yl)-2,2-dimethyl-3-phenylpropyl)isobutyramide | | 444 | isobutyric acid | A |
| 5 | (S)-N-(3-(1-(4-fluorophenyl)-1H-indazol-5-yl)-2,2-dimethyl-3-phenylpropyl)pivalamide | | 458 | pivalic acid | A |
| 6 | (S)-N-(3-(1-(4-fluorophenyl)-1H-indazol-5-yl)-2,2-dimethyl-3-phenylpropyl)methanesulfonamide | | 452 | methanesulfonyl chloride | B |
| 7 | (S)-N-(3-(1-(4-fluorophenyl)-1H-indazol-5-yl)-2,2-dimethyl-3-phenylpropyl)propane-2-sulfonamide | | 480 | isopropylsulfonyl chloride | B |

TABLE 1-continued

| Ex. | Name | Product Structure | (M + H)+ | Alkylating Agent | Coupling Method |
|---|---|---|---|---|---|
| 8 | (S)-1-(3-(1-(4-fluorophenyl)-1H-indazol-5-yl)-2,2-dimethyl-3-phenylpropyl)-3-(2,2,2-trifluoroethyl)urea | | 499 | 2,2,2-trifluoroethylisocyanate | B |
| 9 | (S)-1-tert-butyl-3-(3-(1-(4-fluorophenyl)-1H-indazol-5-yl)-2,2-dimethyl-3-phenylpropyl)urea | | 473 | t-butyl-isocyanate | B |
| 10 | (S)-N-(3-(1-(4-fluorophenyl)-1H-indazol-5-yl)-2,2-dimethyl-3-phenylpropyl)-1-(trifluoromethyl)cyclopropanecarboxamide | | 510 | 1-$CF_3$-cyclopropanecarboxylate | A |
| 11 | (S)-N-(3-(1-(4-fluorophenyl)-1H-indazol-5-yl)-2,2-dimethyl-3-phenylpropyl)ethanesulfonamide | | 466 | ethanesulfonylchloride | B |

TABLE 1-continued

| Ex. | Name | Product Structure | (M + H)+ | Alkylating Agent | Coupling Method |
|---|---|---|---|---|---|
| 12 | (S)-N-(3-(1-(4-fluorophenyl)-1H-indazol-5-yl)-2,2-dimethyl-3-phenylpropyl)cyclopropanesulfonamide | | 478 | cyclopropylsulfonyl chloride | B |
| 13 | (S)-N-(3-(1-(4-fluorophenyl)-1H-indazol-5-yl)-2,2-dimethyl-3-phenylpropyl)propane-1-sulfonamide | | 480 | propanesulfonylchloride | B |
| 14 | (S)-N-(3-(1-(4-fluorophenyl)-1H-indazol-5-yl)-2,2-dimethyl-3-phenylpropyl)-1-(methylsulfonyl)methanesulfonamide | | 530 | 1-chlorosulfonyldimethyl sulfone | B |
| 15 | (S)-N-dimethyl-N'-(3-(1-(4-fluorophenyl)-1H-indazol-5-yl)-2,2-dimethyl-3-phenylpropyl)propane-1-sulfamide | | 481 | N,N-dimethylsulfamoyl chloride | B |

TABLE 1-continued

| Ex. | Name | Product Structure | (M + H)+ | Alkylating Agent | Coupling Method |
|---|---|---|---|---|---|
| (S)-16 | (S)-2,2,2-trifluoro-N-(3-(1-(4-fluorophenyl)-1H-indazol-5-yl)-2,2-dimethyl-3-phenylpropyl)acetamide | | 470 | trifluoroacetic acid | A |
| (R)-16 | (R)-2,2,2-trifluoro-N-(3-(1-(4-fluorophenyl)-1H-indazol-5-yl)-2,2-dimethyl-3-phenylpropyl)acetamide | | 470 | trifluoroacetic acid | A |
| (S)-17 | (S)-3,3,3-trifluoro-N-(3-(1-(4-fluorophenyl)-1H-indazol-5-yl)-2,2-dimethyl-3-phenylpropyl)-propanamide | | 484 | 3,3,3-trifluoropropionic acid | A |

NMR(CDCL$_3$) δ 8.15 (d, 1H), 7.85 (s, 1H), 7.63-7.66 (m, 2H); 7.58-7.60 (d, 1H); 7.50-7.52 (dd, 1H); 7.47-7.49 (dd, 2H); 7.31-7.34 (t, 2H); 7.20-7.25 (m, 3H); 3.94 (s, 1H), 3.31-3.32 (d, 2H); 2.95-3.01, (q, 1H); 1.10-1.12 (d, 6H).

| Ex. | Name | Product Structure | (M + H)+ | Alkylating Agent | Coupling Method |
|---|---|---|---|---|---|
| (R)-17 | (R)-3,3,3-trifluoro-N-(3-(1-(4-fluorophenyl)-1H-indazol-5-yl)-2,2-dimethyl-3-phenylpropyl)-propanamide | | 484 | 3,3,3-trifluoropropionic acid | A |

TABLE 1-continued

| Ex. | Name | Product Structure | (M + H)+ | Alkylating Agent | Coupling Method |
|-----|------|-------------------|----------|------------------|-----------------|
| 18 | (S)-2,2,2-trifluoro-N-(3-(1-(4-fluorophenyl)-1H-indazol-5-yl)-2,2-dimethyl-3-phenylpropyl)ethane-sulfonamide | | 520 | 2,2,2-trifluoroethanesulfonyl chloride | B |

NMR(CDCL$_3$) δ 8.21 (d, 1H); 7.86 (s, 1H); 7.60-7.63 (m, 2H); 7.56-7.58 (d, 1H); 7.51-7.53 (dd, 1H); 7.46-7.47 (dd, 2H); 7.32-7.35 (t, 2H); 7.21-7.25 (m, 3H); 4.01 (s, 1H), 3.63-3.69 (q, 2H); 3.07-3.08, (d, 1H); 1.16-1.17 (d, 6H).

| Ex. | Name | Product Structure | (M + H)+ | Alkylating Agent | Coupling Method |
|-----|------|-------------------|----------|------------------|-----------------|
| 19 | (S)-2,2,3,3,3-pentafluoro-N-(3-(1-(4-fluorophenyl)-1H-indazol-5-yl)-2,2-dimethyl-3-phenylpropyl)propan-amide | | 519 | pentafluoropropionic acid | A |
| 20 | (R)-N-(3-(1-(4-fluorophenyl)-1H-indazol-5-yl)-2,2-dimethyl-3-phenylpropyl)thiophene-2-carboxamide | | 484 | thiophene-2-carboxylic acid | A |

TABLE 1-continued

| Ex. | Name | Product Structure | (M + H)⁺ | Alkylating Agent | Coupling Method |
|---|---|---|---|---|---|
| 21 | (R)-N-(3-(1-(4-fluorophenyl)-1H-indazol-5-yl)-2,2-dimethyl-3-phenylpropyl)-2-(thiophen-2-yl)acetamide | | 498 | 2-(2-thienyl)acetic acid | A |
| 22 | (R)-N-(3-(1-(4-fluorophenyl)-1H-indazol-5-yl)-2,2-dimethyl-3-phenylpropyl)acetamide | | 416 | acetic anhydride | B |
| 23 | (R)-methyl 2-(3-(1-(4-fluorophenyl)-1H-indazol-5-yl)-2,2-dimethyl-3-phenylpropylamino)-2-oxoacetate | | 460 | methyl oxalyl chloride | B |
| 24 | (R)-2-(3-(1-(4-fluorophenyl)-1H-indazol-5-yl)-2,2-dimethyl-3-phenylpropylamino)-2-oxoacetic acid | | 446 | oxalyl chloride | B |

Synthetic Intermediate II 3-(1-(4-Fluorophenyl)-1H-indazol-5-yl)-2,2,5-trimethylhexan-1-amine

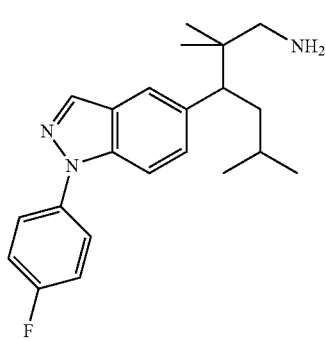

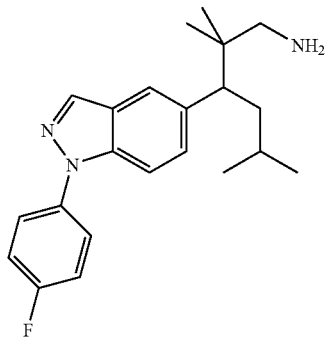

synthetic intermediate II

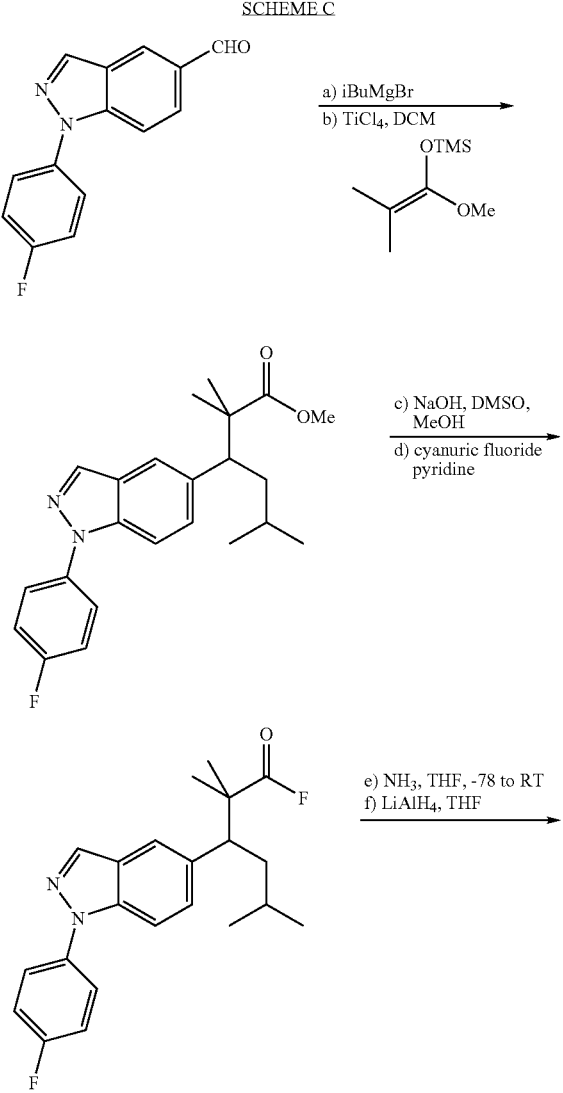

SCHEME C (a) To a solution of 1-(4-fluorophenyl)-1H-indazole-5-carboxaldehyde (100 mg, 0.416 mmol, from experimental 1(e)) in 5 mL of THF was added a solution of 2.0M isobutylmagnesium bromide in THF (0.5 mmol) dropwise. After 1 hr, the reaction was quenched with sat. NH$_4$Cl and extracted with 2× EtOAc. The EtOAc extracts were dried over MgSO$_4$, filtered, and concentrated by rotary evaporator to give 1-(1-(4-fluorophenyl)-1H-indazol-5-yl)-3-methylbutan-1-ol. MS found: (M+H)$^+$=299.

(b) To a solution of 1-(1-(4-fluorophenyl)-1H-indazol-5-yl)-3-methylbutan-1-ol (0.41 mmol) in 20 mL of CH$_2$Cl$_2$ at 0° C. was added 1M TiCl$_4$ in CH$_2$Cl$_2$ (0.5 mmol) all at once. After 30 min, (1-methoxy-2-methylprop-1-enyloxy)trimethylsilane (0.24 mL, 1.2 mmol) was added and the reaction was warmed to rt and stirred overnight. The reaction was quenched with water and extracted with CH$_2$Cl$_2$. The CH$_2$Cl$_2$ extracts were dried over MgSO$_4$, filtered, and concentrated by rotary evaporator to give methyl 3-(1-(4-fluorophenyl)-1H-indazol-5-yl)-2,2,5-trimethylhexanoate. MS found: (M+H)$^+$=383.

(c) Methyl 3-(1-(4-fluorophenyl)-1H-indazol-5-yl)-2,2,5-trimethylhexanoate (0.4 mmol) was dissolved in 5 mL of DMSO, 10 mL of 1 NaOH and 5 mL of MeOH and heated at 100° C. overnight. The reaction was quenched with sat. KH$_2$PO$_4$ and extracted with 2× EtOAc. The EtOAc extracts were dried over MgSO$_4$, filtered, and concentrated by rotary evaporator to give 3-(1-(4-fluorophenyl)-1H-indazol-5-yl)-2,2,5-trimethylhexanoic acid. MS found: (M+H)$^+$=369.

(d)(e) 3-(1-(4-Fluorophenyl)-1H-indazol-5-yl)-2,2,5-trimethylhexanoic acid (0.2 mmol) was converted into the acid fluoride using the identical procedure to that for Synthetic Intermediate I above.

A solution of 3-(1-(4-fluorophenyl)-1H-indazol-5-yl)-2,2,5-trimethylhexanoyl fluoride (1.65 g, 4.23 mmol) in anhydrous THF (30 mL) at −78° C. was bubbled NH$_3$ (g) for 10 minutes. The reaction mixture was sealed and stirred at −78° C. for 15 min and at rt for 1 hr. Water (100 mL) was added, the reaction mixture was extracted with ethyl acetate (100 mL), dried (Na$_2$SO$_4$), and concentrated to give 1.62 g (100% yield) of 3-(1-(4-fluorophenyl)-1H-indazol-5-yl)-2,2,5-trimethylhexanamide, the NMR spectrum of which was consistent with the desired structure.

(f) To a stirred solution of 3-(1-(4-fluorophenyl)-1H-indazol-5-yl)-2,2,5-trimethylhexanoyl fluoride (1.62 g, 4.23 mmol) in anhydrous THF (100 mL) was added 1.0M lithium aluminum hydride in diethyl ether (8.0 mL, 8.0 mmol) portionwise at RT under nitrogen. After stirring at RT for 24 hr, the mixture was carefully quenched with MeOH, poured into a 1N sodium hydroxide solution (100 mL), extracted with ethyl acetate (2×100 mL), dried ($Na_2SO_4$) and concentrated to give 1.3 g (82% yield) of 3-(1-(4-fluorophenyl)-1H-indazol-5-yl)-2,2,5-trimethylhexan-1-amine (Synthetic Intermediate II) as a yellow oil, the NMR spectrum of which was consistent with the desired structure.

Examples 25 to 81

The compounds in Table 2 were synthesized via the transformation shown in Scheme B using Synthetic Intermediate II and the acylating agent indicated in the table.

TABLE 2

| Ex. | Name | Structure | (M + H)⁺ | Acylating Reagent | Coupling Method |
|---|---|---|---|---|---|
| 25 | 2,2,2-trifluoro-N-(3-(1-(4-fluorophenyl)-1H-indazol-5-yl)-2,2,5-trimethylhexyl)acetamide | 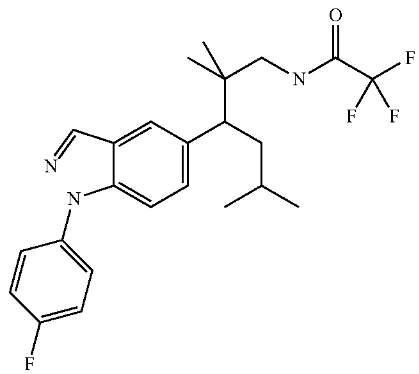 | 450 | (CF₃CO)₂O | B |
| 26 | 1-cyclopropyl-3-(3-(1-(4-fluorophenyl)-1H-indazol-5-yl)-2,2,5-trimethylhexyl)urea | 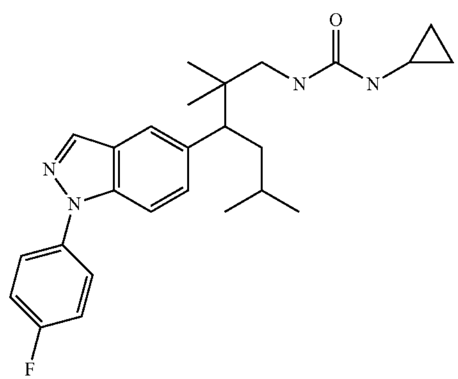 | 437 | isopropyl-isocyanate | B |

TABLE 2-continued

| Ex. | Name | Structure | (M + H)+ | Acylating Reagent | Coupling Method |
|---|---|---|---|---|---|
| 27 | 1-cyclobutyl-3-(3-(1-(4-fluorophenyl)-1H-indazol-5-yl)-2,2,5-trimethylhexyl)urea | 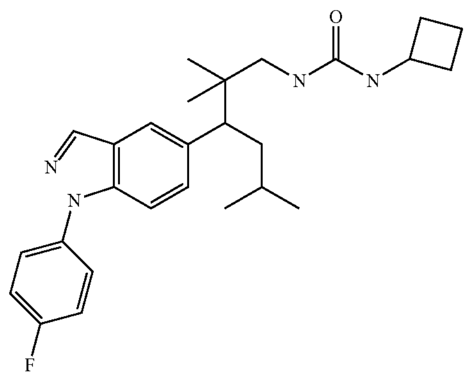 | 451 | cyclobutyl-isocyanate | B |
| 28 | 1-tert-butyl-3-(3-(1-(4-fluorophenyl)-1H-indazol-5-yl)-2,2,5-trimethylhexyl)urea | 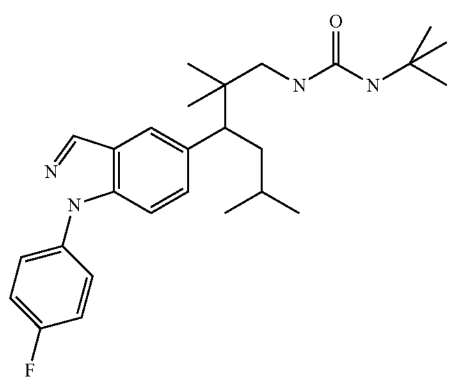 | 453 | tBuNCO | B |

TABLE 2-continued

| Ex. | Name | Structure | (M + H)+ | Acylating Reagent | Coupling Method |
|---|---|---|---|---|---|
| 29 | 1-(3-(1-(4-fluorophenyl)-1H-indazol-5-yl)-2,2,5-trimethylhexyl)-3-(1-hydroxy-2-methylpropan-2-yl)urea | 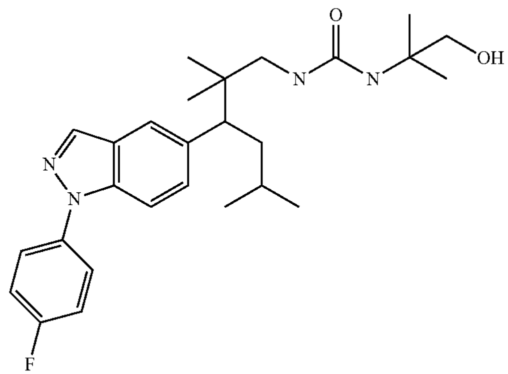 | 469 | | B |
| 30 | N-(3-(1-(4-fluorophenyl)-1H-indazol-5-yl)-2,2,5-trimethylhexyl)-3,3-dimethylpiperidine-1-carboxamide | 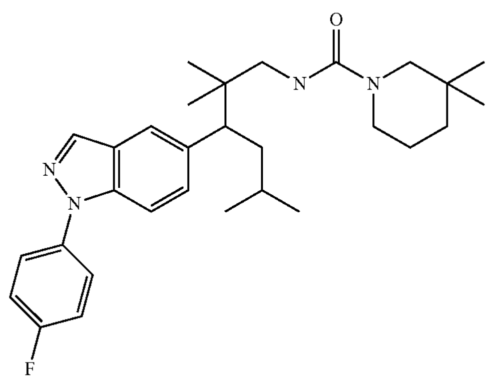 | 493 | | B |

TABLE 2-continued
| Ex. | Name | Structure | (M + H)+ | Acylating Reagent | Coupling Method |
|---|---|---|---|---|---|
| 31 | 1-tert-butyl-3-(3-(1-(4-fluorophenyl)-1H-indazol-5-yl)-2,2,5-trimethylhexyl)-1-methylurea | 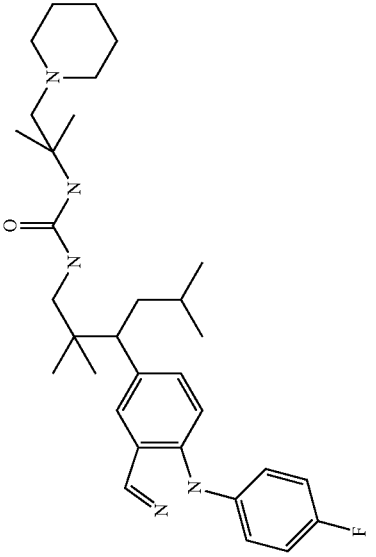 | 467 | 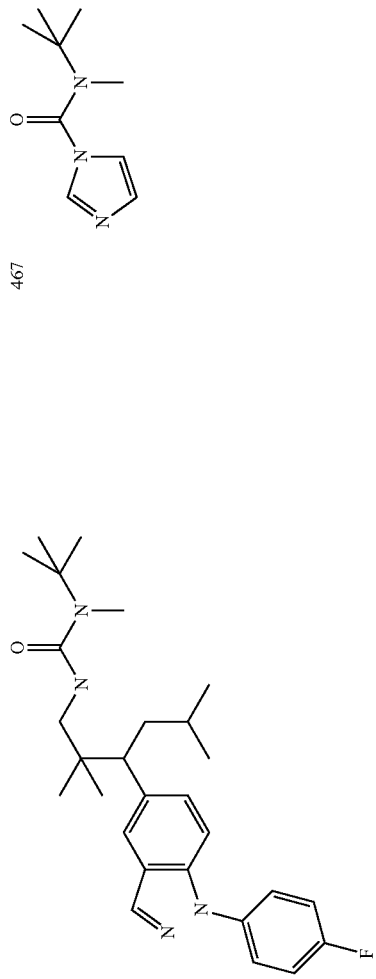 | C |
| 32 | 1-(3-(1-(4-fluorophenyl)-1H-indazol-5-yl)-2,2,5-trimethylhexyl)-3-(2-methyl-1-(piperidin-1-yl)propan-2-yl)urea | 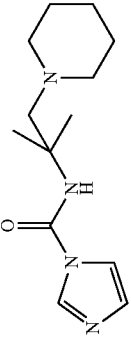 | 536 | 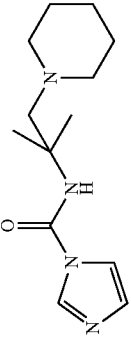 | C |

TABLE 2-continued

| Ex. | Name | Structure | (M + H)+ | Acylating Reagent | Coupling Method |
|---|---|---|---|---|---|
| 33 | 1-(3-(1-(4-fluorophenyl)-1H-indazol-5-yl)-2,2,5-trimethylhexyl)-3-(2-methyl-1-morpholinopropan-2-yl)urea | 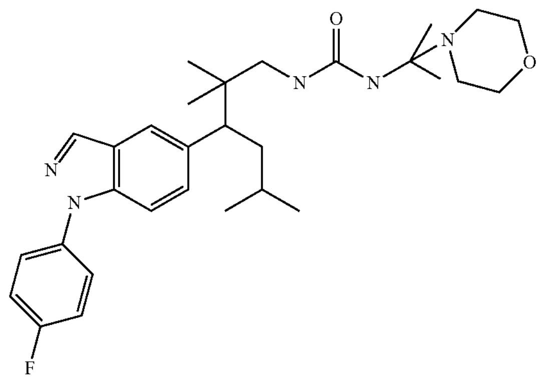 | 538 | | C |
| 34 | 1-(3-(1-(4-fluorophenyl)-1H-indazol-5-yl)-2,2,5-trimethylhexyl)-3-isopropylurea | 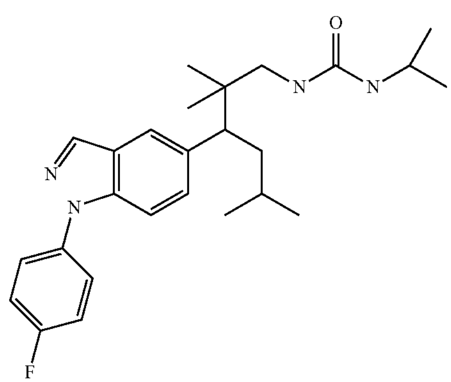 | 439 | isopropyl-isocyanate | B |

TABLE 2-continued

| Ex. | Name | Structure | (M + H)⁺ | Acylating Reagent | Coupling Method |
|---|---|---|---|---|---|
| 35 | 1-(3-(1-(4-fluorophenyl)-1H-indazol-5-yl)-2,2,5-trimethylhexyl)-3-neopentylurea | 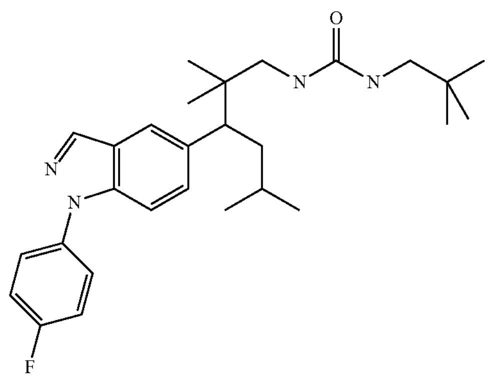 | 467 | tBuCH₂NCO | B |
| 36 | 1-(3-(1-(4-fluorophenyl)-1H-indazol-5-yl)-2,2,5-trimethylhexyl)-3-neopentylurea | 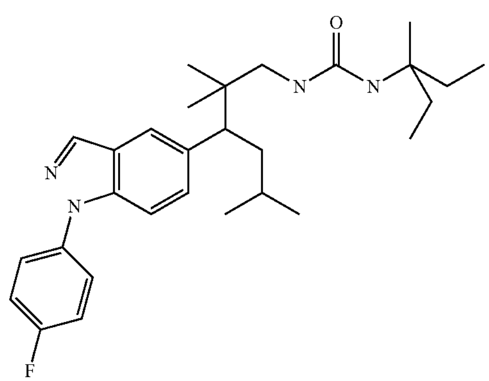 | 481 | | B |

TABLE 2-continued

| Ex. | Name | Structure | (M + H)⁺ | Acylating Reagent | Coupling Method |
|---|---|---|---|---|---|
| 37 | 1-(3-(1-(4-fluorophenyl)-1H-indazol-5-yl)-2,2,5-trimethylhexyl)-3-(tetrahydro-2H-pyran-4-yl)urea | 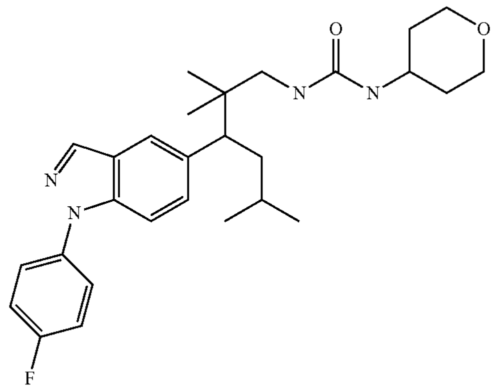 | 481 | 4-tetrahydro-pyranylisocyanate | B |
| 38 | | 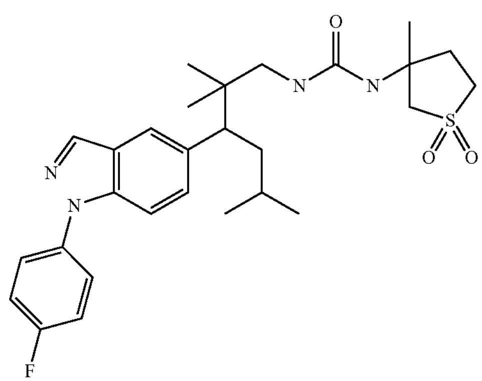 | 529 | | C |

TABLE 2-continued

| Ex. | Name | Structure | (M + H)+ | Acylating Reagent | Coupling Method |
|---|---|---|---|---|---|
| 39 | (2R)-N-(3-(1-(4-fluorophenyl)-1H-indazol-5-yl)-2,2,5-trimethylhexyl)-2-(hydroxymethyl)pyrrolidine-1-carboxamide | 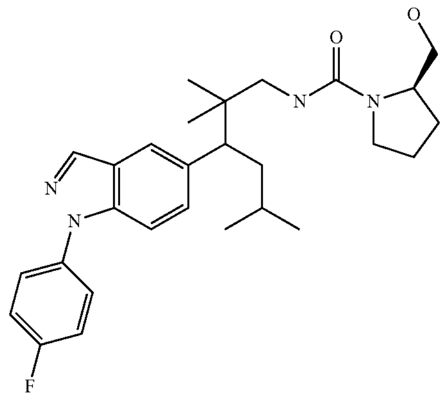 | 481 | | C |
| 40 | 3-amino-N-(3-(1-(4-fluorophenyl)-1H-indazol-5-yl)-2,2,5-trimethylhexyl)azetidine-1-carboxamide | 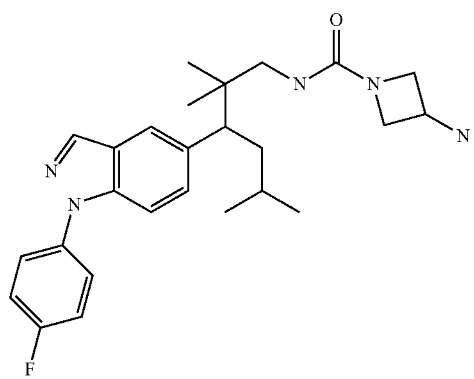 | 452 | | C |

TABLE 2-continued

| Ex. | Name | Structure | (M + H)⁺ | Acylating Reagent | Coupling Method |
|---|---|---|---|---|---|
| 41 | 1-(1-amino-2-methylpropan-2-yl)-3-(3-(1-(4-fluorophenyl)-1H-indazol-5-yl)-2,2,5-trimethylhexyl)urea | 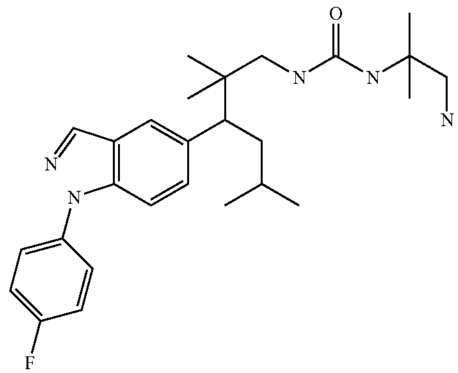 | 468 | | C |
| 42 | 1-(3-(1-(4-fluorophenyl)-1H-indazol-5-yl)-2,2,5-trimethylhexyl)-3-(1-(hydroxymethyl)cyclopentyl)urea | 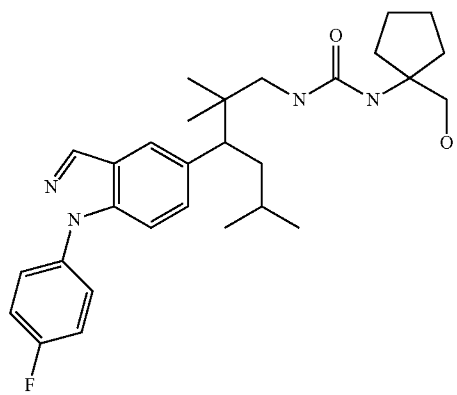 | 495 | | C |

TABLE 2-continued

| Ex. | Name | Structure | (M + H)+ | Acylating Reagent | Coupling Method |
|---|---|---|---|---|---|
| 43 | 1-sec-butyl-3-(3-(1-(4-fluorophenyl)-1H-indazol-5-yl)-2,2,5-trimethylhexyl)urea | 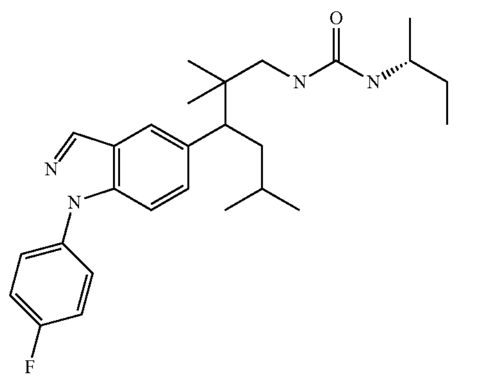 | 453 | | B |
| 44 | 1-((R)-3,3-dimethylbutan-2-yl)-3-(3-(1-(4-fluorophenyl)-1H-indazol-5-yl)-2,2,5-trimethylhexyl)urea | 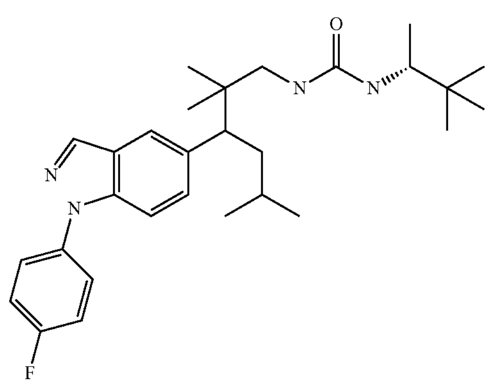 | 481 | | B |

TABLE 2-continued

| Ex. | Name | Structure | (M + H)+ | Acylating Reagent | Coupling Method |
|---|---|---|---|---|---|
| 45 | 1-(3-(1-(4-fluorophenyl)-1H-indazol-5-yl)-2,2,5-trimethylhexyl)-3-((R)-1-hydroxypropan-2-yl)urea | 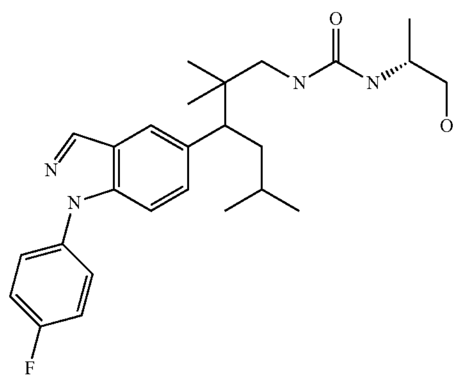 | 455 | | C |
| 46 | 1-(1,3-dihydroxypropan-2-yl)-3-(3-(1-(4-fluorophenyl)-1H-indazol-5-yl)-2,2,5-trimethylhexyl)urea | 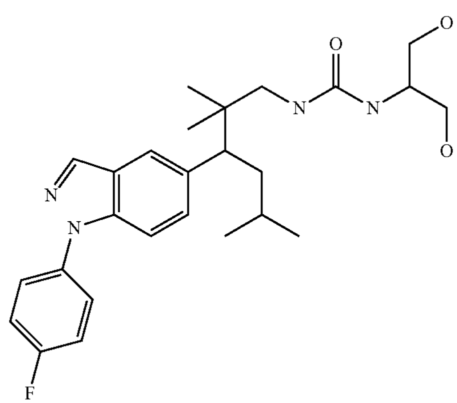 | 471 | | C |

TABLE 2-continued

| Ex. | Name | Structure | (M + H)+ | Acylating Reagent | Coupling Method |
|---|---|---|---|---|---|
| 47 | 1-(3-(1-(4-fluorophenyl)-1H-indazol-5-yl)-2,2,5-trimethylhexyl)-3-((S)-1-hydroxypropan-2-yl)urea | 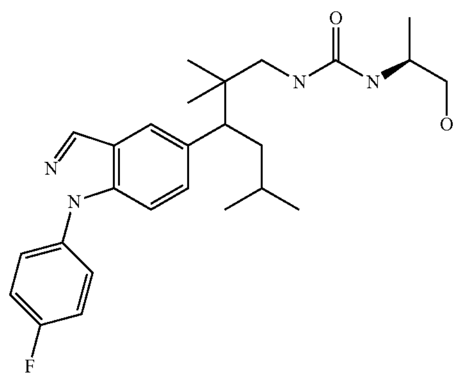 | 455 | | C |
| 48 | 1-(3-(1-(4-fluorophenyl)-1H-indazol-5-yl)-2,2,5-trimethylhexyl)-3-(2-phenylpropan-2-yl)urea | 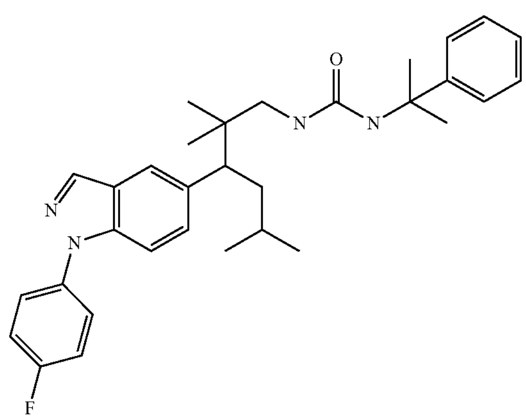 | 515 | | B |

TABLE 2-continued

| Ex. | Name | Structure | (M + H)+ | Acylating Reagent | Coupling Method |
|---|---|---|---|---|---|
| 49 | 1-sec-butyl-3-(3-(1-(4-fluorophenyl)-1H-indazol-5-yl)-2,2,5-trimethylhexyl)urea | 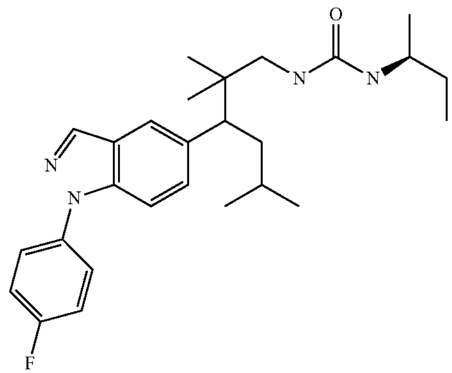 | 453 | | B |
| 50 | 1-(3-(1-(4-fluorophenyl)-1H-indazol-5-yl)-2,2,5-trimethylhexyl)-3-phenylurea | 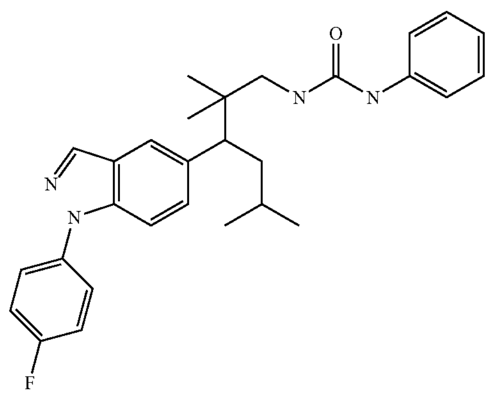 | 473 | PhNCO | B |

TABLE 2-continued

| Ex. | Name | Structure | (M + H)⁺ | Acylating Reagent | Coupling Method |
|---|---|---|---|---|---|
| 51 | 3-(3-(1-(4-fluorophenyl)-1H-indazol-5-yl)-2,2,5-trimethylhexyl)ureido)-3-methylbutanoic acid | 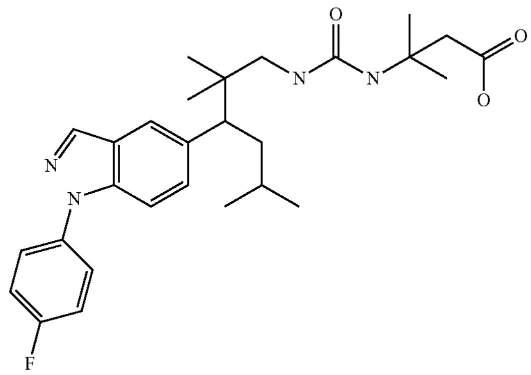 | 497 | | C* |
| 52 | 1-(2-(2,6-dimethylpyridin-3-yl)propan-2-yl)-3-(3-(1-(4-fluorophenyl)-1H-indazol-5-yl)-2,2,5-trimethylhexyl)urea | 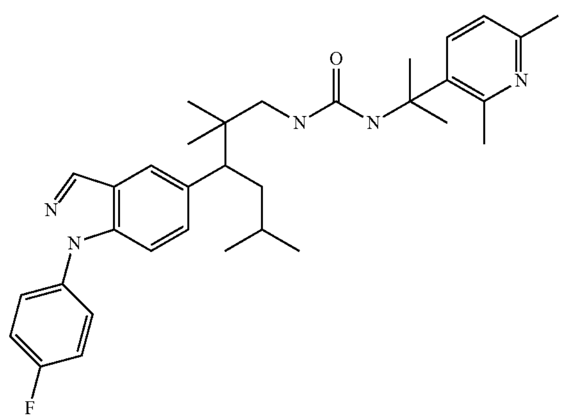 | 544 | | C |

TABLE 2-continued

| Ex. | Name | Structure | (M + H)+ | Acylating Reagent | Coupling Method |
|---|---|---|---|---|---|
| 53 | 1-(3-((1-(4-fluorophenyl)-1H-indazol-5-yl)-2,2,5-trimethylhexyl)-3-(2-(2-methyl)pyridin-4-yl)propan-2-yl)urea | 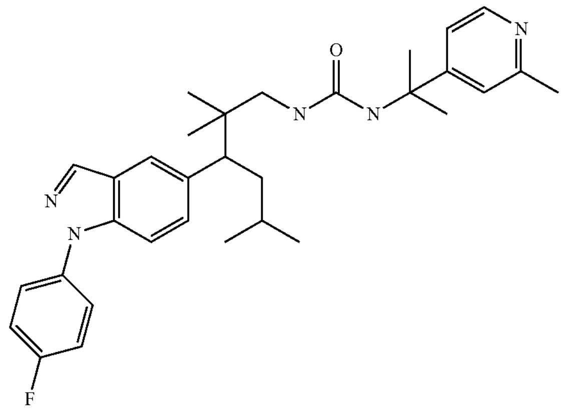 | 530 | | C |
| 54 | 1-(3-((1-(4-fluorophenyl)-1H-indazol-5-yl)-2,2,5-trimethylhexyl)-3-(1-(4-fluorophenyl)-2-methyl)propan-2-yl)urea | 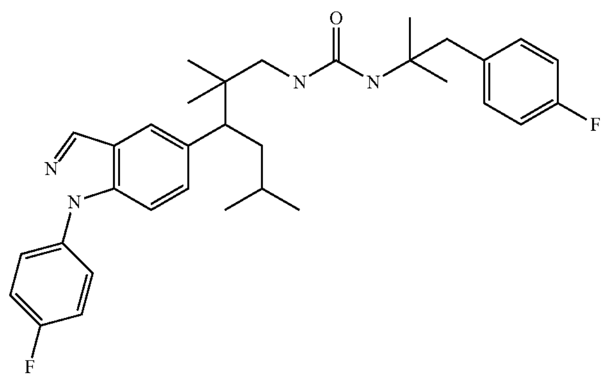 | 547 | | C |

TABLE 2-continued

| Ex. | Name | Structure | (M + H)+ | Acylating Reagent | Coupling Method |
|---|---|---|---|---|---|
| 55 | 3-(3-(1-(4-fluorophenyl)-1H-indazol-5-yl)-2,2,5-trimethylhexyl)-1,1-dimethylurea | 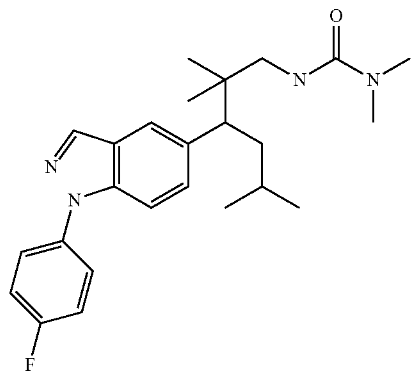 | 425 | | C |
| 56 | 2-(3-(3-(1-(4-fluorophenyl)-1H-indazol-5-yl)-2,2,5-trimethylhexyl)ureido)-2-methyl-N-phenylpropanamide | 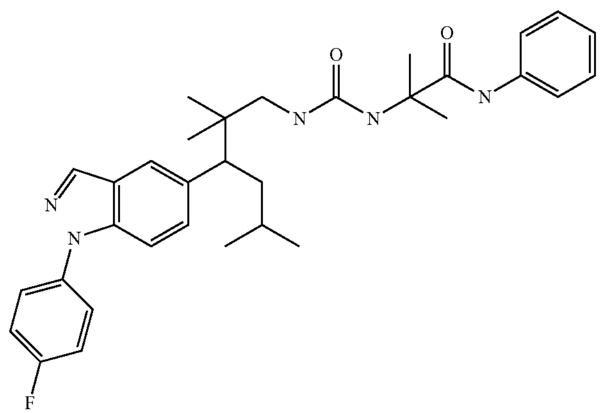 | 558 | | C |

TABLE 2-continued

| Ex. | Name | Structure | (M + H)⁺ | Acylating Reagent | Coupling Method |
|---|---|---|---|---|---|
| 57A enantA | 2,2,2-trifluoro-N-(3-(1-(4-fluorophenyl)-1H-indazol-5-yl)-2,2,5-trimethylhexyl)-ethanesulfonamide | 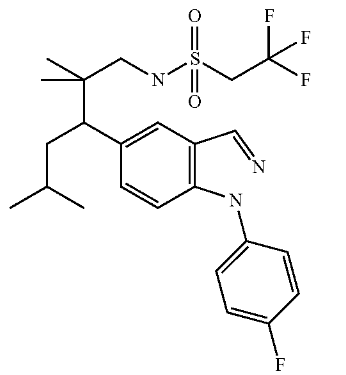 | 500 | CF₃CH₂SO₂Cl | B |
| 57B enantB | same | | 500 | CF₃CH₂SO₂Cl | B |
| 58A enantA | 1-(3-(1-(4-fluorophenyl)-1H-indazol-5-yl)-2,2,5-trimethylhexyl)-3-(2,2,2-trifluoroethyl)urea | 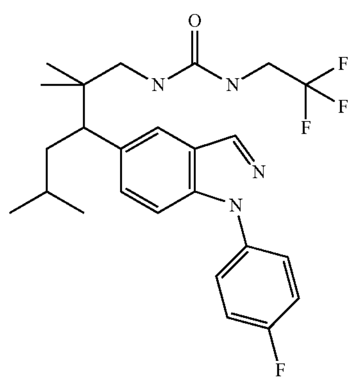 | 479 | CF₃CH₂NCO | B |

TABLE 2-continued

| Ex. | Name | Structure | (M + H)+ | Acylating Reagent | Coupling Method |
|---|---|---|---|---|---|
| 58B enantB | same | | 479 | CF3CH2NCO | B |
| 59A enantA | 3,3,3-trifluoro-N-(3-(1-(4-fluorophenyl)-1H-indazol-5-yl)-2,2,5-trimethylhexyl)propanamide | 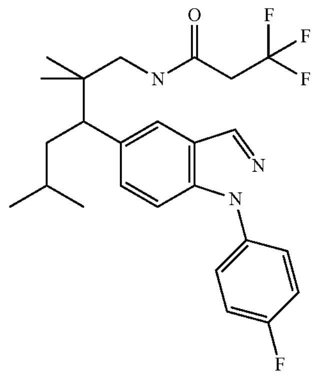 | 464 | CF3CH2CO2H | A |
| 59B enantB | same | | 464 | CF3CH2CO2H | A |
| 60 | 2,2,2-trifluoroethyl 3-(1-(4-fluorophenyl)-1H-indazol-5-yl)-2,2,5-trimethylhexylcarbamate | 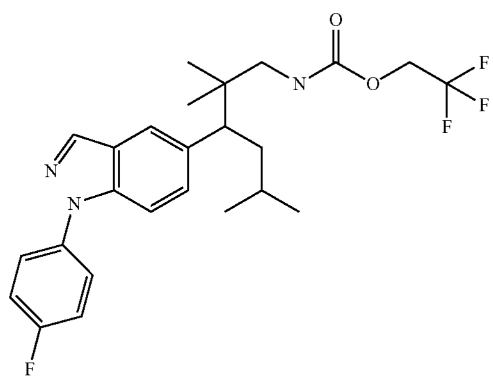 | 480 | CF3CH2OCCl | B |

TABLE 2-continued

| Ex. | Name | Structure | (M + H)+ | Acylating Reagent | Coupling Method |
|---|---|---|---|---|---|
| 61 | 1-(3-(1-(4-fluorophenyl)-1H-indazol-5-yl)-2,2,5-trimethylhexyl)urea | 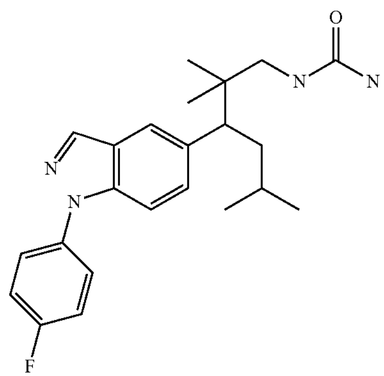 | 397 | KNCO | B |
| 62 | neopentyl 3-(1-(4-fluorophenyl)-1H-indazol-5-yl)-2,2,5-trimethylhexylcarbamate | 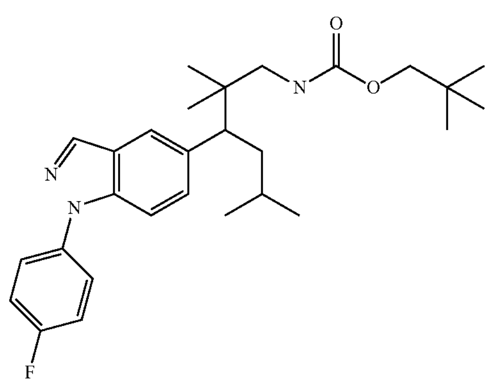 | 468 | tBu-CH$_2$OCOCl | B |

TABLE 2-continued

| Ex. | Name | Structure | (M + H)+ | Acylating Reagent | Coupling Method |
|---|---|---|---|---|---|
| 63 | | 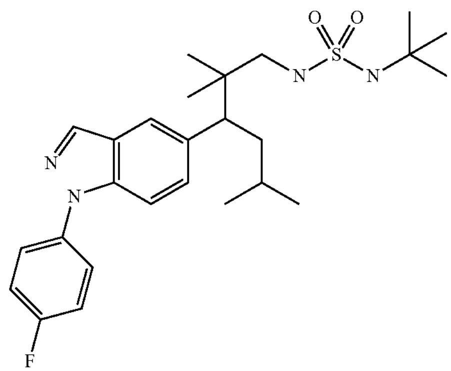 | 489 | tBuSO2Cl | B |
| 64 | 1-(2-(2-tert-butylpyridin-4-yl)propan-2-yl)-3-(3-(1-(4-fluorophenyl)-1H-indazol-5-yl)-2,2,5-trimethylhexyl)urea | 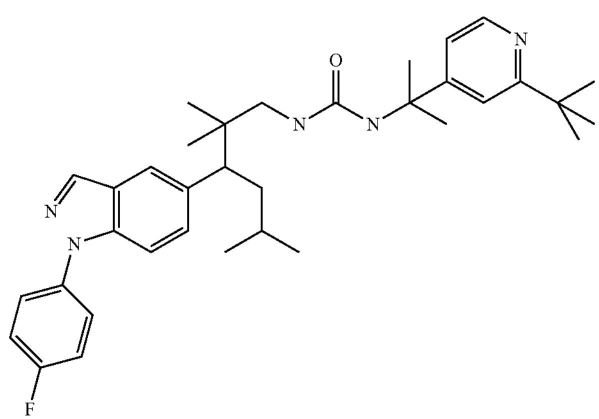 | 572 | | C |

TABLE 2-continued

| Ex. | Name | Structure | (M + H)+ | Acylating Reagent | Coupling Method |
|---|---|---|---|---|---|
| 65 | 3-(3-(1-(4-fluorophenyl)-1H-indazol-5-yl)-2,2,5-trimethylhexyl)-1,1-dimethylurea | 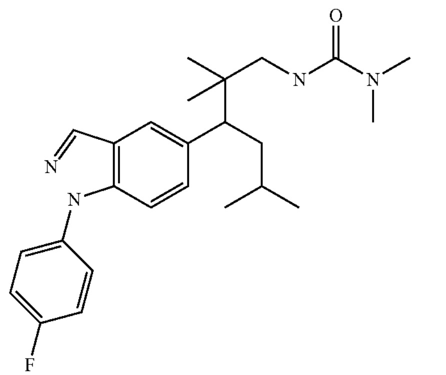 | 425 | (dimethylcarbamoyl imidazole) | C |
| 66 | N-(3-(1-(4-fluorophenyl)-1H-indazol-5-yl)-2,2,5-trimethylhexyl)-3,3-dimethylbutanamide | 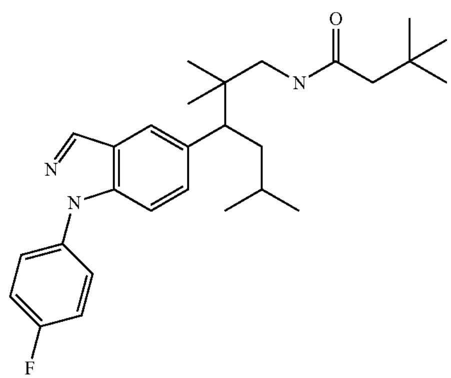 | 452 | tBuCH$_2$CO$_2$H | A |

TABLE 2-continued

| Ex. | Name | Structure | (M + H)+ | Acylating Reagent | Coupling Method |
|---|---|---|---|---|---|
| 67 | N-(3-(1-(4-fluorophenyl)-1H-indazol-5-yl)-2,2,5-trimethylhexyl)-3,3-dimethyl-2-oxobutanamide | 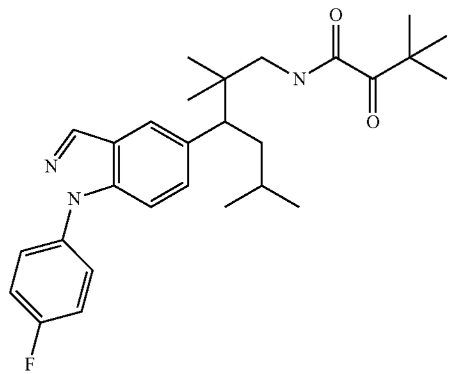 | 466 | tBuCOCOCl | B |
| 68 | 3-(4-chlorophenyl)-N-(3-(1-(4-fluorophenyl)-1H-indazol-5-yl)-2,2,5-trimethylhexyl)-3-methylbutanamide | 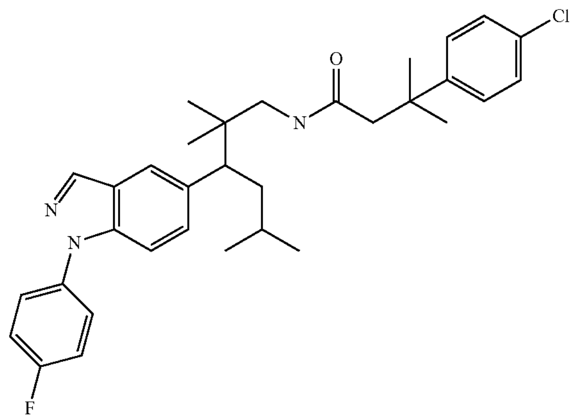 | 548 | | A |

TABLE 2-continued

| Ex. | Name | Structure | (M + H)+ | Acylating Reagent | Coupling Method |
|---|---|---|---|---|---|
| 69-diastA | N-(3-(1-(4-fluorophenyl)-1H-indazol-5-yl)-2,2,5-trimethylhexyl)-2-hydroxy-3,3-dimethylbutanamide | 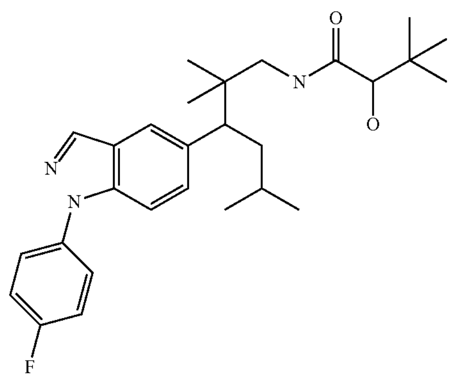 | 468 | | A |
| 69-diastB | N-(3-(1-(4-fluorophenyl)-1H-indazol-5-yl)-2,2,5-trimethylhexyl)-2-hydroxy-3,3-dimethylbutanamide | 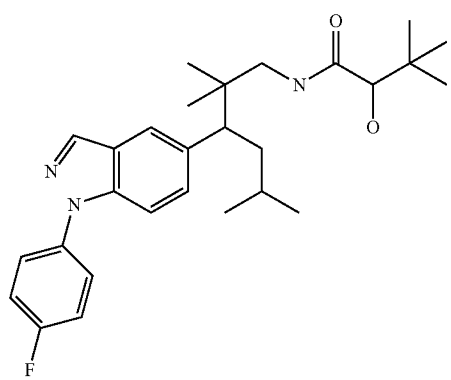 | 468 | | B |
| 70 | 1-(3-(1H-indazol-5-yl)-2,2,5-trimethylhexyl)-3-tert-butylurea | 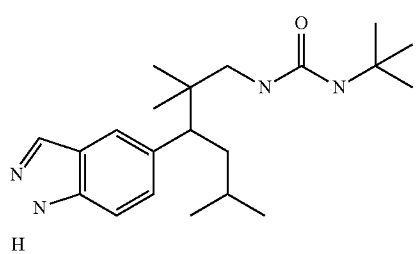 | 360 | tBuNCO | B |

TABLE 2-continued

| Ex. | Name | Structure | (M + H)+ | Acylating Reagent | Coupling Method |
|---|---|---|---|---|---|
| 71A diastA | 1-((S)-2,3-dihydro-1H-inden-1-yl)-3-(3-(1-(4-fluorophenyl)-1H-indazol-5-yl)-2,2,5-trimethylhexyl)urea | 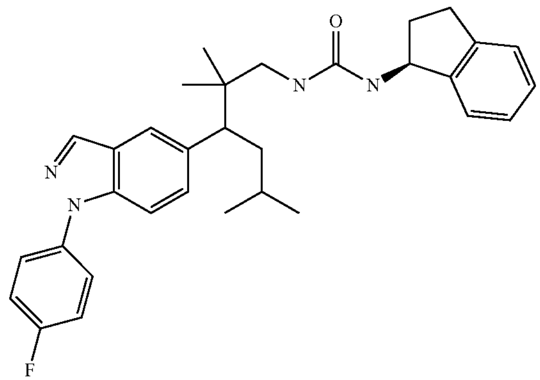 | 513 | | B |
| 71B diastB | 1-((R)-2,3-dihydro-1H-inden-1-yl)-3-(3-(1-(4-fluorophenyl)-1H-indazol-5-yl)-2,2,5-trimethylhexyl)urea | 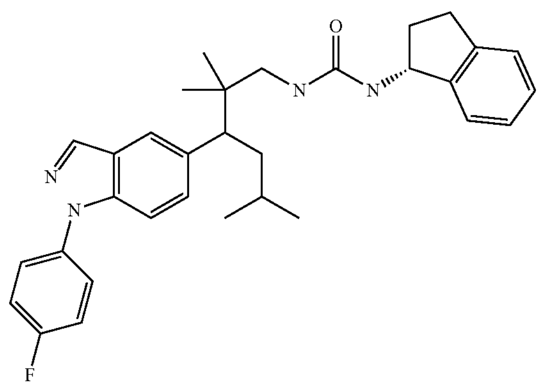 | 513 | | B |

TABLE 2-continued

| Ex. | Name | Structure | (M + H)+ | Acylating Reagent | Coupling Method |
|---|---|---|---|---|---|
| 72 | 1-(3-(1-(4-fluorophenyl)-1H-indazol-5-yl)-2,2,5-trimethylhexyl)-3-(2-methylbut-3-yn-2-yl)urea | 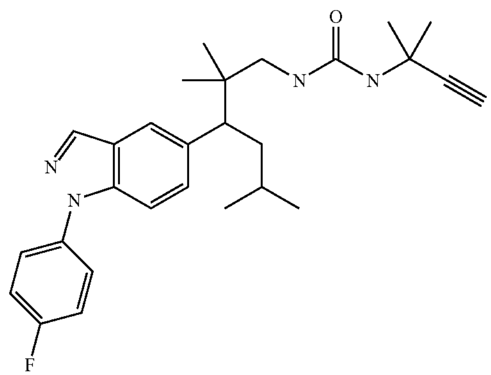 | 463 | | B |
| 73 | 1-benzhydryl-3-(3-(1-(4-fluorophenyl)-1H-indazol-5-yl)-2,2,5-trimethylhexyl)urea | 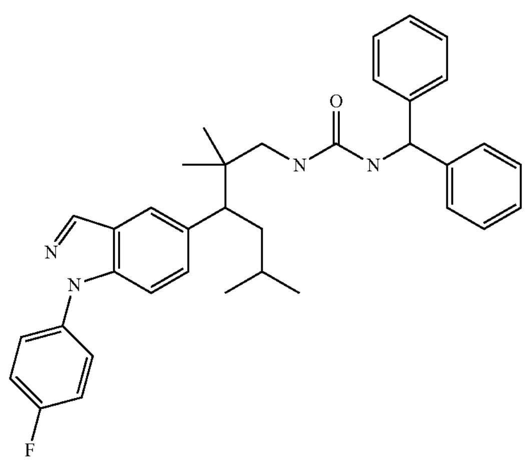 | 563 | | B |

TABLE 2-continued

| Ex. | Name | Structure | (M + H)+ | Acylating Reagent | Coupling Method |
|---|---|---|---|---|---|
| 74 | 1-(4-tert-butylcyclohexyl)-3-(3-(1-(4-fluorophenyl)-1H-indazol-5-yl)-2,2,5-trimethylhexyl)urea | 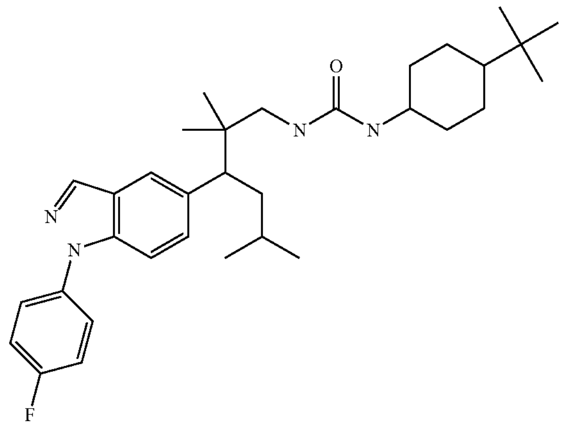 | 535 | | B |
| 75 | 1-(3-(1-(4-fluorophenyl)-1H-indazol-5-yl)-2,2,5-trimethylhexyl)-3-((R)-1-(naphthalene-1-yl)ethyl)urea | 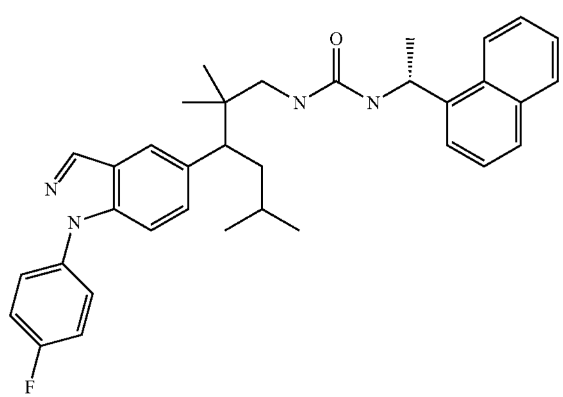 | 551 | | B |

TABLE 2-continued

| Ex. | Name | Structure | (M + H)+ | Acylating Reagent | Coupling Method |
|---|---|---|---|---|---|
| 76 | 1-(3-(1-(4-fluorophenyl)-1H-indazol-5-yl)-2,2,5-trimethylhexyl)-3-((S)-1-(naphthalene-1-yl)ethyl)urea | 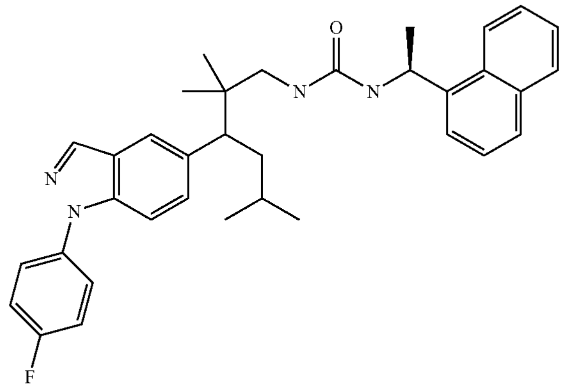 | 551 | | B |
| 77 | 1-((S)-3,3-dimethylbutan-2-yl)-3-(3-(1-(4-fluorophenyl)-1H-indazol-5-yl)-2,2,5-trimethylhexyl)urea | 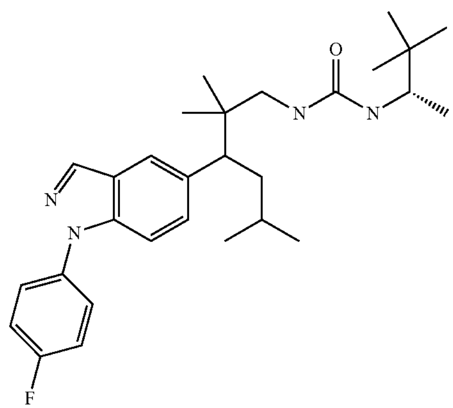 | 481 | | B |

TABLE 2-continued

| Ex. | Name | Structure | (M + H)+ | Acylating Reagent | Coupling Method |
|---|---|---|---|---|---|
| 78 | 1-(3-(1-(4-fluorophenyl)-1H-indazol-5-yl)-2,2,5-trimethylhexyl)-3-((1R,2S)-2-hydroxy-2,3-dihydro-1H-inden-1-yl) urea | 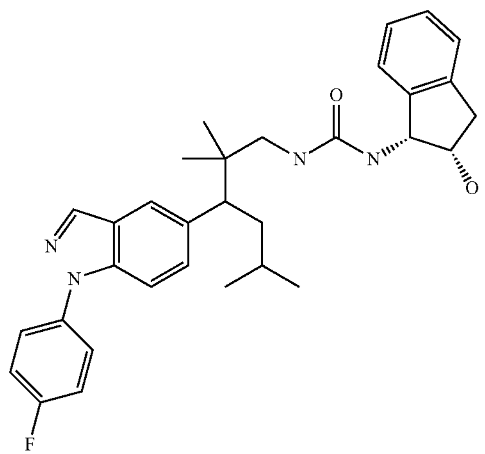 | 529 | | C |
| 79 | 1-(1-benzylpiperidin-4-yl)-3-(3-(1-(4-fluorophenyl)-1H-indazol-5-yl)-2,2,5-trimethylhexyl)urea | 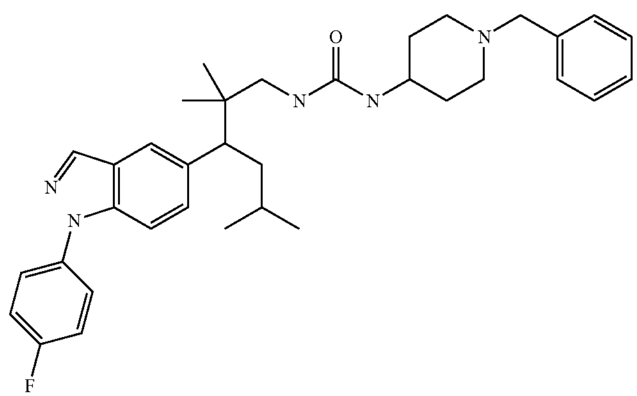 | 570 | | C |

TABLE 2-continued

| Ex. | Name | Structure | (M + H)⁺ | Acylating Reagent | Coupling Method |
|---|---|---|---|---|---|
| 80 | 1-(1-(4-chlorophenyl)-3-hydroxypropan-2-yl)-3-(3-(1-(4-fluorophenyl)-1H-indazol-5-yl)-2,2,5-trimethylhexyl)urea | 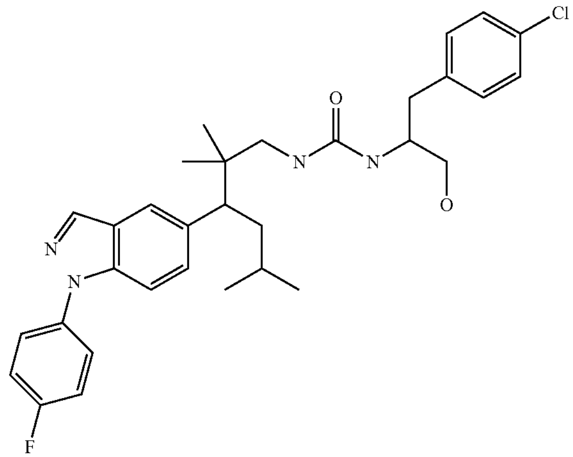 | 565 | | C |
| 81 | N-(3-(1-(4-fluorophenyl)-1H-indazol-5-yl)-2,2,5-trimethylhexyl)-2,4,6-trimethylbenzenesulfonamide | 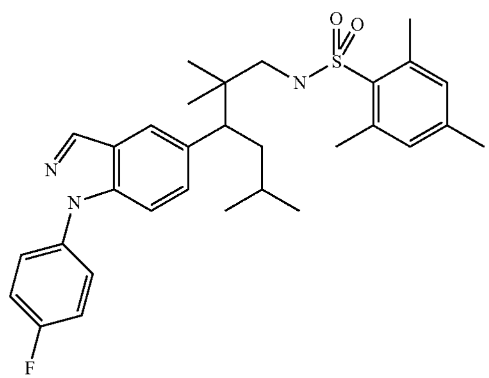 | 536 | 2,4,6-trimethyl-benzene | B |

*The final compound was completed by TFA deprotection of the tBu ester.

Synthetic Intermediate III (S)-3-(1H-Indazol-5-yl)-2,2-dimethyl-3-phenylpropan-1-amine

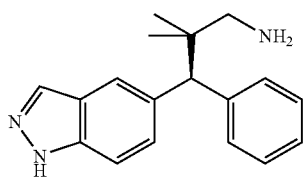

SCHEME D

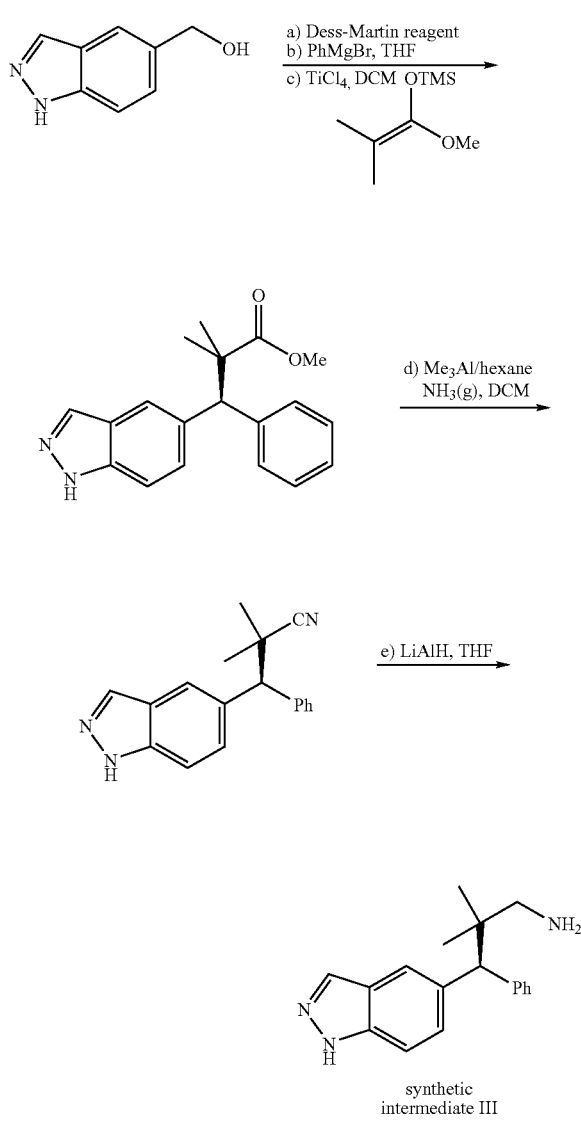

synthetic intermediate III (a) (1H-Indazol-5-yl)methanol (29 g, 200 mmol) was dissolved in 2 L DCM and treated with commercially available Dess-Martin periodinane (100 g, 235 mmol). After 12 h, the reaction mixture was concentrated in vacuo then dissolved in 1 L of EtOAc and washed with 1N NaOH×2. The organic layers were dried over $MgSO_4$, filtered, and concentrated to give 28.6 g (100%) of product 1H-indazole-5-carbaldehyde. MS found: $(M+H)^+=147$.

(b) 1H-Indazole-5-carbaldehyde (28 g, 200 mmol) was dissolved in 1 L of THF and 25 mL of TMEDA and treated with PhMgBr (800 mL of 1.0 M in THF, 800 mmol). After 36 h, the reaction was quenched with MeOH, poured into brine and extracted with EtOAc×3. The organic layers were dried over $MgSO_4$, filtered, and concentrated. Crude residue was crystallized from DCM/ether and solids were collected and dried to give 28.8 g (64%) of product 1H-indazol-5-yl)(phenyl)methanol. MS found: $(M+H)^+=319$.

(c) (1H-Indazol-5-yl)(phenyl)methanol (12.1 g, 54 mmol) was dissolved in 200 mL of dry THF and 200 mL of DCM and cooled to 0 C. Added 1-methoxy-2-methyl-1-(trimethylsiloxy)propene (43.6, 250 mmol) followed by dropwise addition of $TiCl_4$ (60 mL of 1.0 M DCM solution, 60 mmol). After 12 h, the reaction was quenched with MeOH, poured into brine and extracted 2×DCM. The organic layers were dried over $MgSO_4$, filtered, concentrated, and then chromatographed using 1:2 EtOAc/hexane to give 11.1 g (66% yield) of methyl 3-(1H-indazol-5-yl)-2,2-dimethyl-3-phenylpropanoate which was separated by chiral chromatography. MS found: $(M+H)^+=309$.

(d) Ammonia (g) was bubbled through 20 mL of DCM at −78 C for 30 min followed by dropwise addition of $AlMe_3$ (10 mL of 1.0 M hexane solution, 20 mmol). The reaction mixture was allowed to warm to RT then added 20 mL of xylenes followed by (S)-methyl 3-(1H-indazol-5-yl)-2,2-dimethyl-3-phenylpropanoate (1.64 g, 5.3 mmol). The reaction was heated to reflux after boiling off DCM. After 12 h, reaction was checked and partially complete. After 12 h, the reaction was cooled to −78 C and carefully quenched with MeOH, poured into brine and extracted 2× EtOAc. The organic layers were dried over $MgSO_4$, filtered, concentrated in, and then chromatographed on $SiO_2$ using 1:2 to 1:1 EtOAc/hexanes gradient to give 770 mg (53% yield) of (S)-3-(1H-indazol-5-yl)-2,2-dimethyl-3-phenylpropanenitrile. MS found: $(M+H)^+=276$.

(e) To a stirred solution of (S)-3-(1H-indazol-5-yl)-2,2-dimethyl-3-phenylpropanenitrile (248 mg, 0.9 mmol) in anhydrous THF (10 mL) was added 1.0M lithium aluminum hydride in diethyl ether (4.0 mL, 4.0 mmol) portionwise at RT under nitrogen. The reaction mixture was heated at reflux. After stirring at RT for 2 hr, the mixture was cooled then carefully quenched with MeOH, poured into a 1N sodium brine, extracted with ethyl acetate (2×100 mL), dried ($Na_2SO_4$) and concentrated to give 240 mg (95% yield) of (S)-3-(1H-indazol-5-yl)-2,2-dimethyl-3-phenylpropan-1-amine (Synthetic Intermediate III). MS found: $(M+H)^+=280$.

Examples 82 and 83

The compounds in Table 3 were synthesized via the transformation shown in Scheme B using Synthetic Intermediate III and the acylating agent indicated in the table.

TABLE 3

| Ex. | Name | Product Structure | Acylating Agent | (M + H)+ | Coupling Method |
|---|---|---|---|---|---|
| (R)-82 | (R)-N-(3-(1H-indazol-5-yl)-2,2-dimethyl-3-phenylpropyl)-3,3,3-trifluoropropanamide | | | 390 | A |
| (S)-82 | (S)-N-(3-(1H-indazol-5-yl)-2,2-dimethyl-3-phenylpropyl)-3,3,3-trifluoropropanamide | | | 390 | A |
| (R)-83 | (S)-N-(3-(1H-indazol-5-yl)-2,2-dimethyl-3-phenylpropyl)-2,2,2-trifluoroethanesulfonamide | | | 426 | B |
| (S)-83 | (S)-N-(3-(1H-indazol-5-yl)-2,2-dimethyl-3-phenylpropyl)-2,2,2-trifluoroethanesulfonamide | | | 426 | B |

NMR(CDCl$_3$) δ 8.24 (d, 1H); 7.85 (s, 1H); 7.55-7.72 (m, 2H); 7.37-7.39 (d, 2H); 7.25-7.29 (t, 2H); 7.15-7.22 (m, 1H); 3.97 (s, 1H), 3.60-3.64 (q, 2H); 2.97-2.99, (d, 1H); 1.07-1.08 (d, 6H).

SCHEME E

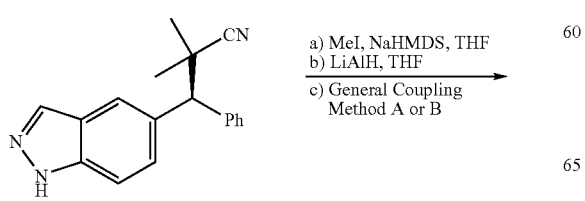

a) MeI, NaHMDS, THF
b) LiAlH, THF
c) General Coupling Method A or B

-continued

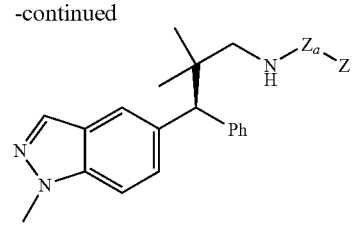

Examples 84 and 85 were synthesized using the procedure outlined in Scheme E.

Example 84

(S)—N-(2,2-Dimethyl-3-(1-methyl-1H-indazol-5-yl)-3-phenylpropyl)-3,3,3-trifluoropropanamide

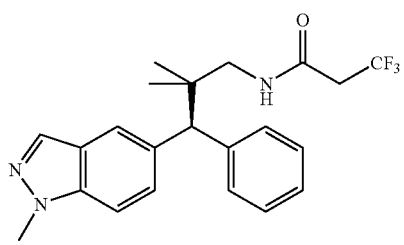

(a) To a stirred solution of (S)-3-(1H-indazol-5-yl)-2,2-dimethyl-3-phenylpropanenitrile (80 mg, 0.29 mmol) in anhydrous THF (5 mL) was added 1.0M NaHMDS in THF (0.30 mL, 0.30 mmol) at RT under nitrogen. After stirring at RT for 10 min, methyl iodide (0.03 mL, 0.48 mmol) was added, and the reaction was stirred overnight. The reaction mixture was poured into water, extracted with ethyl acetate (2×100 mL), dried (MgSO$_4$) and concentrated. The resulting N1 and N2 adducts were separated by HPLC to give 54 mg (62% yield) of the desired N1 adduct (S)-2,2-dimethyl-3-(1-methyl-1H-indazol-5-yl)-3-phenylpropanenitrile. MS found: (M+H)$^+$=290.

(b)(c) To a stirred solution of (S)-2,2-dimethyl-3-(1-methyl-1H-indazol-5-yl)-3-phenylpropanenitrile (54 mg, 0.193 mmol) in anhydrous THF (10 mL) was added 1.0M lithium aluminum hydride in diethyl ether (0.5 mL, 0.5 mmol) portionwise at RT under nitrogen. After stirring at RT for 3 hr, the mixture was carefully quenched with MeOH, poured into brine, extracted with ethyl acetate (2×100 mL), dried (MgSO$_4$) and concentrated. The crude product was coupled with 3,3,3-trifluoropropanoic acid (29 mg, 0.226 mmol) using General Coupling Method A to give 40 mg (51% yield) of (S)—N-(2,2-dimethyl-3-(1-methyl-1H-indazol-5-yl)-3-phenylpropyl)-3,3,3-trifluoropropanamide. MS found: (M+H)$^+$=404.

Example 85

(S)—N-(2,2-Dimethyl-3-(1-methyl-1H-indazol-5-yl)-3-phenylpropyl)-2,2,2-trifluoroethanesulfonamide

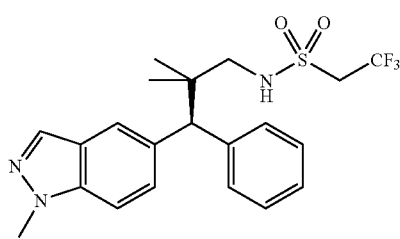

(a)(b) To a stirred solution of (S)-2,2-dimethyl-3-(1-methyl-1H-indazol-5-yl)-3-phenylpropanenitrile (40 mg, 0.138 mmol) in anhydrous THF (10 mL) was added 1.0M lithium aluminum hydride in diethyl ether (0.5 mL, 0.5 mmol) portionwise at RT under nitrogen. After stirring at RT for 3 hr, the mixture was carefully quenched with MeOH, poured into brine, extracted with ethyl acetate (2×100 mL), dried (MgSO$_4$) and concentrated. The crude product was coupled with 2,2,2-trifluoroethanesulfonyl chloride (26 mg, 0.14 mmol) using General Coupling Method B to give (S)—N-(2,2-dimethyl-3-(1-methyl-1H-indazol-5-yl)-3-phenylpropyl)-3,3,3-trifluoropropanamide. MS found: (M+H)$^+$=426.

SCHEME F

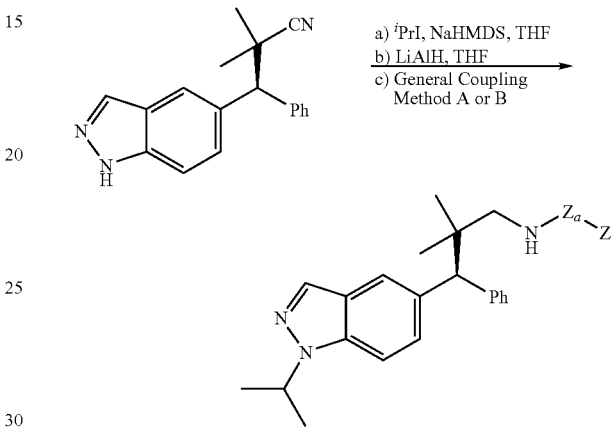

a) $^i$PrI, NaHMDS, THF
b) LiAlH, THF
c) General Coupling Method A or B

Examples 86 and 87 were synthesized using the procedure outlined in Scheme F.

Example 86

(S)—N-(2,2-Dimethyl-3-(1-isopropyl-1H-indazol-5-yl)-3-phenylpropyl)-3,3,3-trifluoropropanamide

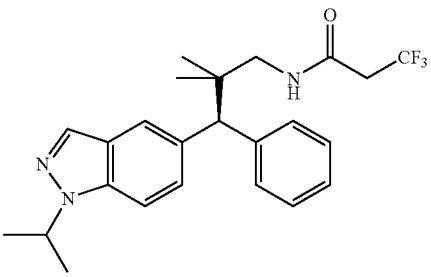

(a) To a stirred solution of (S)-3-(1H-indazol-5-yl)-2,2-dimethyl-3-phenylpropanenitrile (100 mg, 0.36 mmol) in anhydrous THF (5 mL) was added 1.0M NaHMDS in THF (0.36 mL, 0.36 mmol) at RT under nitrogen. After stirring at RT for 10 min, isopropyl iodide (0.035 mL, 0.36 mmol) was added, and the reaction was stirred overnight. The reaction mixture was poured into water, extracted with ethyl acetate (2×100 mL), dried (MgSO$_4$) and concentrated. The resulting N1 and N2 adducts were separated by HPLC to give 47 mg (41% yield) of the desired N1 adduct (S)-2,2-dimethyl-3-(1-sopropmethyl-1H-indazol-5-yl)-3-phenylpropanenitrile. MS found: (M+H)$^+$=318.

(b)(c) To a stirred solution of (S)-2,2-dimethyl-3-(1-isopropyl-1H-indazol-5-yl)-3-phenylpropanenitrile (24 mg, 0.075 mmol) in anhydrous THF (10 mL) was added 1.0M lithium aluminum hydride in diethyl ether (0.5 mL, 0.5 mmol) portionwise at RT under nitrogen. After stirring at RT for 3 hr, the mixture was carefully quenched with MeOH, poured into brine, extracted with ethyl acetate (2×100 mL), dried (MgSO$_4$) and concentrated. The crude product was coupled with 3,3,3-trifluoropropanoic acid (10 mg, 0.0.78 mmol) using General Coupling Method A to give 13 mg (45% yield) of (S)—N-(2,2-dimethyl-3-(1-isopropyl-1H-indazol-5-yl)-3-phenylpropyl)-3,3,3-trifluoropropanamide. MS found: (M+H)$^+$=432.

NMR (CDCl$_3$) δ 8.04 (s, 1H); 7.73 (s, 1H); 7.38-7.45 (m, 2H); 7.32-7.34 (d, 1H); 7.23-7.27 (t, 2H); 7.14-7.18 (m, 2H); 4.74-4.82 (m, 1H), 3.84 (s, 1H); 3.24-3.25 (d, 2H); 2.89-2.97, (q, 2H); 1.52 (s, 3H); 1.50 (s, 3H); 1.02-1.04 (d, 6H).

Example 87

(S)—N-(2,2-Dimethyl-3-(1-isopropyl-1H-indazol-5-yl)-3-phenylpropyl)-2,2,2-trifluoroethanesulfonamide

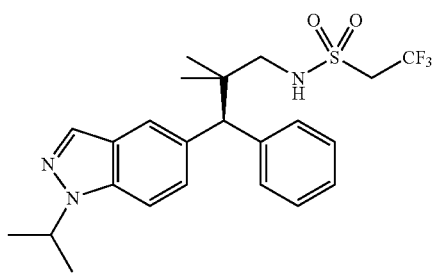

(a)(b) To a stirred solution of (S)-2,2-dimethyl-3-(1-methyl-1H-indazol-5-yl)-3-phenylpropanenitrile (24 mg, 0.078 mmol) in anhydrous THF (10 mL) was added 1.0M lithium aluminum hydride in diethyl ether (0.5 mL, 0.5 mmol) portionwise at RT under nitrogen. After stirring at RT for 3 hr, the mixture was carefully quenched with MeOH, poured into brine, extracted with ethyl acetate (2×100 mL), dried (MgSO$_4$) and concentrated. The crude product was coupled with 2,2,2-trifluoroethanesulfonyl chloride (14 mg, 0.073 mmol) using General Coupling Method B to give (S)—N-(2,2-dimethyl-3-(1-methyl-1H-indazol-5-yl)-3-phenylpropyl)-3,3,3-trifluoropropanamide. MS found: (M+H)$^+$=468.

SCHEME G

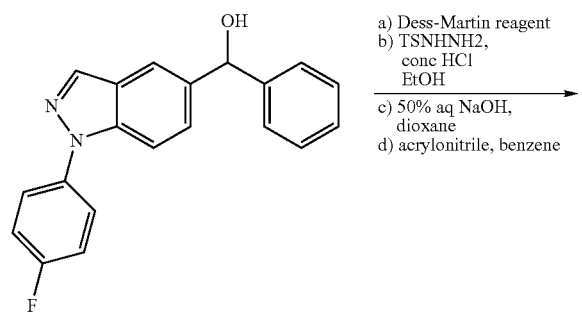

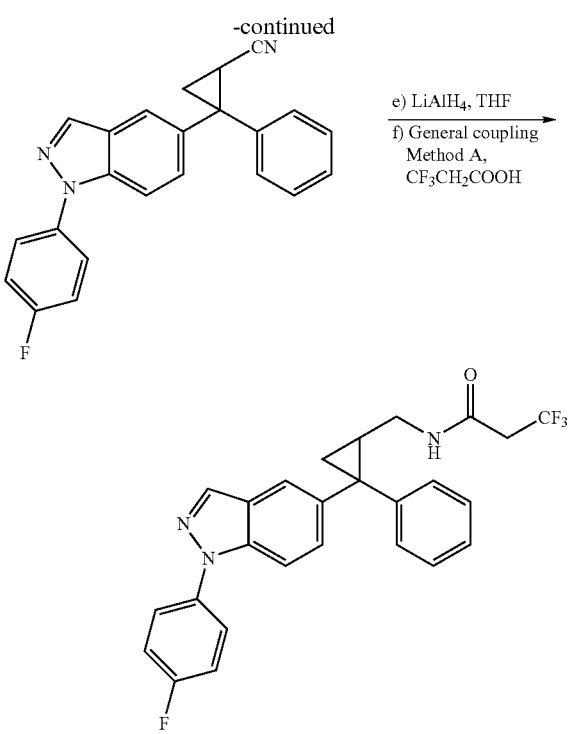

Examples 88 and 89 were synthesized using the procedure outlined in Scheme G.

Example 88

3,3,3-Trifluoro-N-((2-(1-(4-fluorophenyl)-1H-indazol-5-yl)-2-phenylcyclopropyl)methyl)propanamide

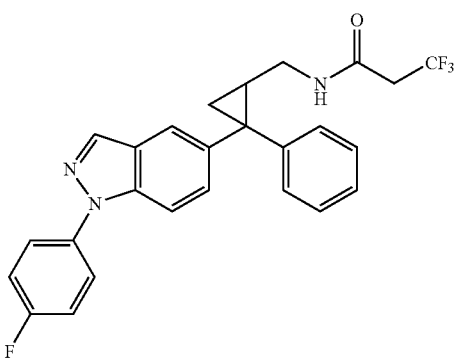

(a) (1-(4-Fluorophenyl)-1H-indazol-5-yl)(phenyl)methanol (1.2 g, 3.77 mmol) was dissolved in 200 mL of DCM and treated with commercially available Dess-Martin periodinane (2.0 g, 4.7 mmol). After 12 h, the reaction mixture was washed with 1N NaOH×2. The organic layers were dried over MgSO$_4$, filtered, and concentrated to give 1.2 g (100%) of product (1-(4-fluorophenyl)-1H-indazol-5-yl)(phenyl)methanone. MS found: (M+H)$^+$=317.

(b) (1-(4-Fluorophenyl)-1H-indazol-5-yl)(phenyl)methanone (1.2 g, 3.77 mmol) was dissolved in 500 mL of EtOH. Added a few drops of conc HCl and heated at reflux. After 12 h, the reaction was concentrated in vacuo to give a quantitative yield of N'-((1-(4-fluorophenyl)-1H-indazol-5-yl)(phenyl)methylene)-4-methylbenzenesulfonohydrazide. MS found: (M+H)$^+$=485.

(c)(d) N'-((1-(4-fluorophenyl)-1H-indazol-5-yl)(phenyl)methylene)-4-methylbenzenesulfonohydrazide (1.82 g, 3.77 mmol) was dissolved in 20 mL of dioxane and 20 mL of a 50% aqueous NaOH solution and heated at 85 C. After 1 h, the reaction mixture was adjusted to pH 4-5 with conc HCl and extracted 2× EtOAc. The organic layers were dried over MgSO$_4$, filtered, concentrated, and the crude product was taken to the next step. Crude residue was dissolved in 20 mL of benzene and acrylonitrile (4 mmol) was added. The reaction mixture was heated to reflux. After 2 h, the reaction was poured into brine and extracted 2× EtOAc. The organic layers were dried over MgSO$_4$, filtered, concentrated, and then purified by HPLC to give 275 mg (21% yield) of 2-(1-(4-fluorophenyl)-1H-indazol-5-yl)-2-phenylcyclopropanecarbonitrile. MS found: (M+H)$^+$=354.

(e) To a stirred solution of 2-(1-(4-fluorophenyl)-1H-indazol-5-yl)-2-phenylcyclopropanecarbonitrile (275 mg, 0.78 mmol) in anhydrous THF (10 mL) was added 1.0M lithium aluminum hydride in diethyl ether (2.0 mL, 2.0 mmol) portionwise at RT under nitrogen. After stirring at RT for 12 hr, the mixture was quenched with MeOH, poured into a 1N sodium brine, extracted with ethyl acetate (2×100 mL), dried (MgSO$_4$), concentrated and purified by HPLC to give 142 mg (39% yield) of (2-(1-(4-fluorophenyl)-1H-indazol-5-yl)-2-phenylcyclopropyl)methanamine as the TFA salt. MS found: (M+H)$^+$=358.

(f) (2-(1-(4-Fluorophenyl)-1H-indazol-5-yl)-2-phenylcyclopropyl)methanamine (71 mg, 0.15 mmol) was coupled with 3,3,3-trifluoropropanoic acid (38 mg, 0.2 mmol) using General Coupling Method A to give 60 mg (86% yield) of 3,3,3-trifluoro-N-((2-(1-(4-fluorophenyl)-1H-indazol-5-yl)-2-phenylcyclopropyl)methyl) propanamide. MS found: (M+H)$^+$=468.

Example 89

2,2,2-Trifluoro-N-42-(1-(4-fluorophenyl)-1H-indazol-5-yl)-2-phenylcyclopropyl)methyl)ethanesulfonamide

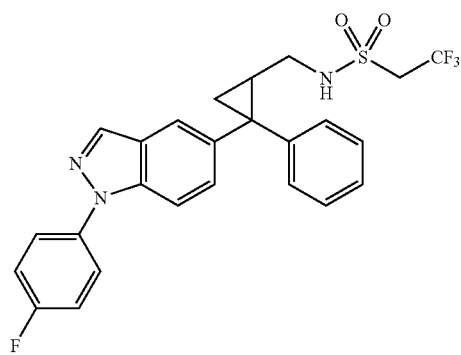

(2-(1-(4-Fluorophenyl)-1H-indazol-5-yl)-2-phenylcyclopropyl)methanamine (71 mg, 0.15 mmol) was coupled with 2,2,2-trifluoroethanesulfonyl chloride (50 mg, 0.5 mmol) using General Coupling Method B to give 60 mg (86% yield) of 2,2,2-trifluoro-N-((2-(1-(4-fluorophenyl)-1H-indazol-5-yl)-2-phenylcyclopropyl)methyl)ethanesulfonamide. MS found: (M+H)$^+$=504.

Synthetic Intermediate IV 3-(1-(4-Fluorophenyl)-1H-indazol-5-yl)-2-methyl-3-phenylpropan-1-amine

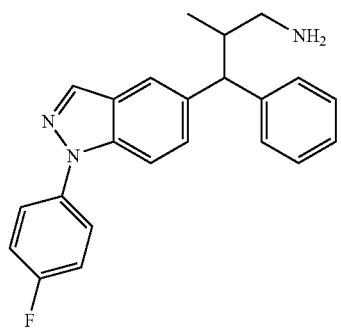

SCHEME H

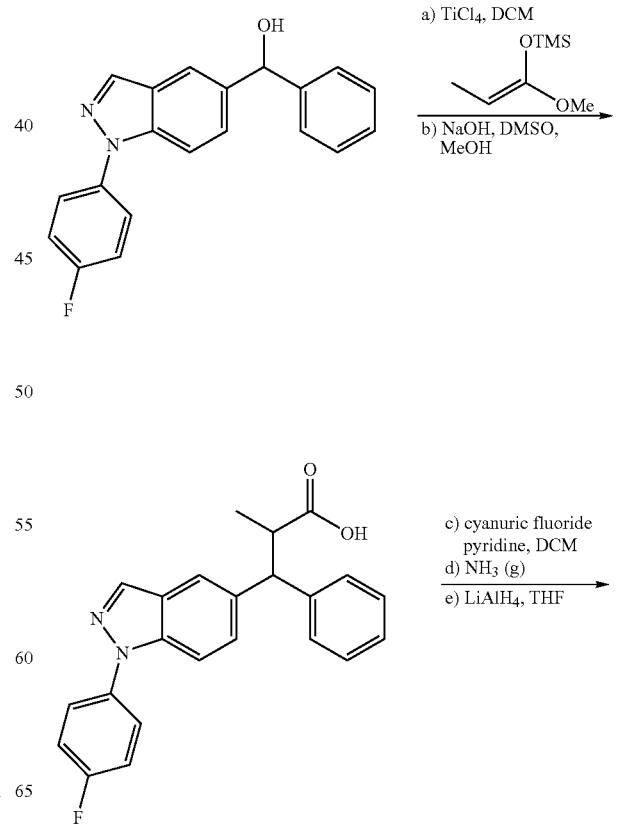

-continued

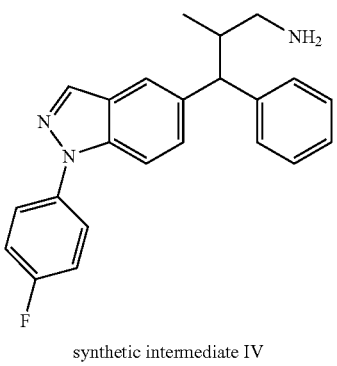

synthetic intermediate IV (a)(b) To a solution of (1-(4-fluorophenyl)-1H-indazol-5-yl)(phenyl)methanol (800 mg, 2.5 mmol) and (1-methoxyprop-1-enyloxy)trimethylsilane (1 mL, 6.25 mmol) in 30 mL of dry DCM was added TiCl$_4$ (2.5 mL of 1.0 M DCM solution, 2.5 mmol) and then stirred 1 h. The reaction was quenched with MeOH, poured into aqueous sodium bicarbonate and extracted 2× EtOAc. The organic layers were dried over MgSO$_4$, filtered, concentrated to give methyl 3-(1-(4-fluorophenyl)-1H-indazol-5-yl)-2-methyl-3-phenylpropanoat. Crude methyl 3-(1-(4-fluorophenyl)-1H-indazol-5-yl)-2-methyl-3-phenylpropanoate was heated to 100 C overnight in a mixture of 2 M NaOH/MeOH/DMSO (1:1:1). The next day, the reaction was cooled, acidified to pH 5 with HCl and extracted 2× EtOAc. The organic layers were washed with water×2, dried over MgSO$_4$, filtered, concentrated in vacuo, and purified by HPLC to give 770 mg (82% yield, 2 steps) of acid 3-(1-(4-fluorophenyl)-1H-indazol-5-yl)-2-methyl-3-phenylpropanoic acid which could be separated into its four isomers by chiral HPLC. MS found: (M+H)$^+$=375.

(c)(d) 3-(1-(4-Fluorophenyl)-1H-indazol-5-yl)-2-methyl-3-phenylpropanoic acid (120, mg, 0.32 mmol) was converted into the acid fluoride using the identical procedure to that for Synthetic Intermediate I above.

(e) A solution of 3-(1-(4-fluorophenyl)-1H-indazol-5-yl)-2-methyl-3-phenylpropanoyl fluoride (0.32 mmol) in anhydrous THF (5 mL) at −78° C. was bubbled NH$_3$ (g) for 10 minutes. The reaction mixture was sealed and stirred at −78° C. for 15 min and at rt for 1 hr. Water (100 mL) was added, the reaction mixture was extracted with ethyl acetate (100 mL), dried (Na$_2$SO$_4$), and concentrated to give 115 mg (100% yield) of 3-(1-(4-fluorophenyl)-1H-indazol-5-yl)-2-methyl-3-phenylpropanamide, the NMR spectrum of which was consistent with the desired structure.

(f) To a stirred solution of 3-(1-(4-fluorophenyl)-1H-indazol-5-yl)-2-methyl-3-phenylpropanamide (115 mg, 0.32 mmol) in anhydrous THF (10 mL) was added 1.0M lithium aluminum hydride in diethyl ether (2.0 mL, 2.0 mmol) portionwise at RT under nitrogen. After stirring at RT for 24 hr, the mixture was carefully quenched with MeOH, poured into brine (100 mL), extracted with ethyl acetate (2×100 mL), dried (Na$_2$SO$_4$) and concentrated to give 115 mg (100% yield) of 3-(1-(4-fluorophenyl)-1H-indazol-5-yl)-2-methyl-3-phenylpropan-1-amine (Synthetic Intermediate IV) as a yellow oil, the NMR spectrum of which was consistent with the desired structure.

Examples 90 to 97

The compounds in Table 4 were synthesized via the transformation shown in Scheme B using Synthetic Intermediate IV and the acylating agent indicated in the table.

TABLE 4

| Ex. | Name | Product Structure | Acylating Agent | (M + H)$^+$ | Coupling Method |
|---|---|---|---|---|---|
| 90 | 3,3,3-trifluoro-N-(3-(1-(4-fluorophenyl)-1H-indazol-5-yl)-2-methyl-3-phenylpropyl)propanamide | [structure] | [structure] | 470 | A |

Diastereomer A: NMR(CDCL$_3$) δ 8.17 (s, 1H); 7.77 (s, 1H) 7.57-7.63 (m, 3H); 7.42-7.44 (dd, 1H); 7.27-7.33 (m, 4H); 7.16-7.23 (m, 3H); 3.69-3.71 (d, 1H); 3.41-3.46 (m, 1H); 3.02-3.08 (m, 1H); 2.99-3.05 (q, 2H); 2.70-2.78 (m, 1H); 0.94-0.95 (d, 3H).

Diastereomer B: NMR(CDCL$_3$) δ 8.15 (s, 1H); 7.71 (s, 1H) 7.61-7.64 (m, 2H); 7.56-7.57 (d, 1H); 7.35-7.39 (m, 3H); 7.30-7.31 (t, 2H); 7.18-7.24 (m, 3H); 3.69-3.71 (d, 1H); 3.34-3.39 (m, 1H); 3.15-3.20 (m, 1H); 2.91-2.97 (q, 2H); 2.70-2.76 (m, 1H); 0.93-0.95 (d, 3H).

TABLE 4-continued

| Ex. | Name | Product Structure | Acylating Agent | (M + H)⁺ | Coupling Method |
|---|---|---|---|---|---|
| 91 | 2,2,2-trifluoro-N-(3-(1-(4-fluorophenyl)-1H-indazol-5-yl)-2-methyl-3-phenylpropyl)ethanesulfonamide | | | 506 | B |
| 92 | N-(3-(1-(4-fluorophenyl)-1H-indazol-5-yl)-2-methyl-3-phenylpropyl)methanesulfonamide | | | 438 | B |
| 93 | N-(3-(1-(4-fluorophenyl)-1H-indazol-5-yl)-2-methyl-3-phenylpropyl)ethanesulfonamide | | | 452 | B |

Diastereomer A: NMR(CDCL$_3$) δ 8.15 (s, 1H); 7.74 (s, 1H) 7.59-7.64 (m, 3H); 7.38-7.40 (dd, 1H); 7.27-7.33 (m, 4H); 7.20-7.23 (m, 3H); 3.73-3.75 (d, 1H); 3.62-3.67 (q, 2H); 3.23-3.27 (m, 1H); 2.91-2.97 (m, 1H); 2.74-2.78 (m, 1H); 1.01-1.02 (d, 3H).

Diastereomer B: NMR(CDCL$_3$) δ 8.15 (s, 1H); 7.70 (s, 1H) 7.60-7.64 (m, 2H); 7.56-7.58 (d, 1H); 7.29-7.37 (m, 5H); 7.19-7.24 (m, 3H); 3.72-3.74 (d, 1H); 3.63-3.69 (q, 2H); 3.22-3.27 (m, 1H); 2.94-3.00 (m, 1H); 2.71-2.77 (m, 1H); 1.00-1.01 (d, 3H).

TABLE 4-continued

| Ex. | Name | Product Structure | Acylating Agent | (M + H)+ | Coupling Method |
|---|---|---|---|---|---|
| 94 | N-(3-(1-(4-fluorophenyl)-1H-indazol-5-yl)-2-methyl-3-phenylpropyl)propane-2-sulfonamide | 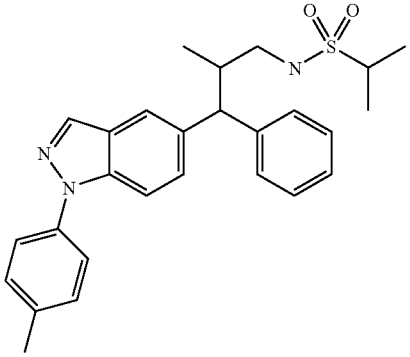 | 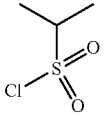 | 466 | B |
| 95 | N-(3-(1-(4-fluorophenyl)-1H-indazol-5-yl)-2-methyl-3-phenylpropyl)propane-1-sulfonamide | 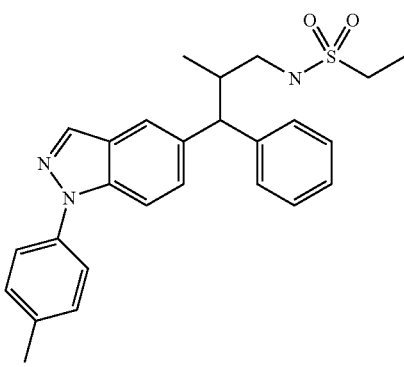 | 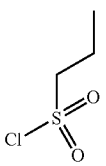 | 466 | B |
| 96 | 3,3,3-trifluoro-N-(3-(1-(4-fluorophenyl)-1H-indazol-5-yl)-2-methyl-3-phenylpropyl)propane-1-sulfonamide | 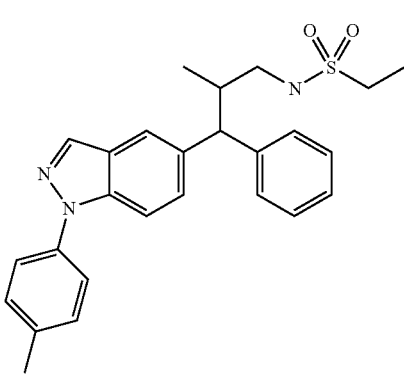 | 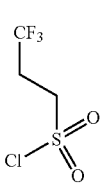 | 520 | B |
| 97 | 1-tert-butyl-3-(3-(1-(4-fluorophenyl)-1H-indazol-5-yl)-2-methyl-3-phenylpropyl)urea | 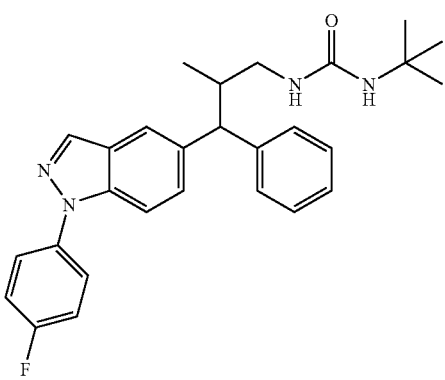 | tBu-NCO | 459 | B |

General Silyl Ketene Acetal Method A

To a solution of LDA (1 eq) in THF (10-20 mL) at −78° C. was added ester (12-36 mmol). After stirring for 1 h, TMS-Cl (2 eq.) was added and the reaction is allowed to gradually warm to 25° C. The reaction mixture was filtered through a sintered glass funnel and filtrate was concentrated in vacuo. The residue was triturated in hexanes and solid were again filtered away. Filtrate was concentrated in vacuo and used in the next step.

SCHEME I

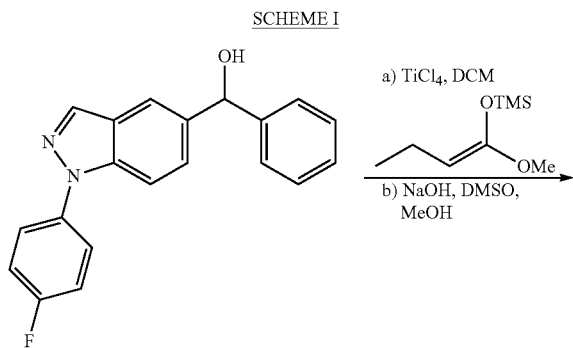

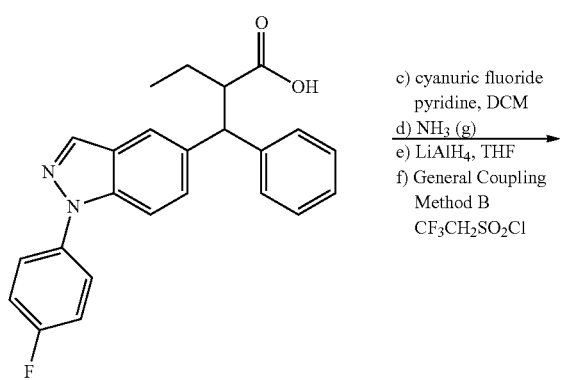

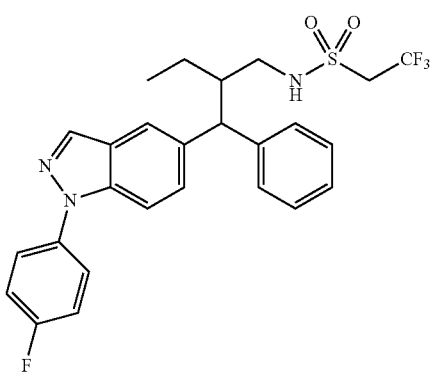

Example 98 was synthesized using the procedure outlined in Scheme I.

Example 98

2,2,2-Trifluoro-N-(2-((1-(4-fluorophenyl)-1H-indazol-5-yl)(phenyl)methyl)butyl)ethanesulfonamide

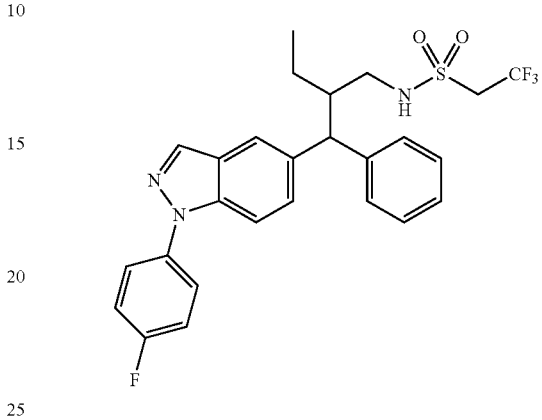

(a) To a solution of (1-(4-fluorophenyl)-1H-indazol-5-yl)(phenyl)methanol (250 mg, 0.79 mmol) and (1-methoxybut-1-enyloxy)trimethylsilane (32 mmol) which was prepared using General Silyl Ketene Acetal Method A in 10 mL of dry DCM was added TiCl$_4$ (0.8 mL of 1.0 M DCM solution, 0.8 mmol) and then stirred 1 h. The reaction was quenched with MeOH, poured into aqueous sodium bicarbonate and extracted 2× EtOAc. The organic layers were dried over MgSO$_4$, filtered, concentrated and purified on SiO$_2$ by MPLC using a EtOAc/hexane gradient to give 200 mg (63% yield) of methyl 2-((1-(4-fluorophenyl)-1H-indazol-5-yl)(phenyl)methyl)butanoate. MS found: (M+H)$^+$=403.

(b) Methyl 2-((1-(4-fluorophenyl)-1H-indazol-5-yl)(phenyl)methyl)butanoate was heated to 100 C overnight in a mixture of 2 M NaOH/MeOH/DMSO (1:1:1). The next day, the reaction was cooled, acidified to pH 5 with HCl and extracted 2× EtOAc. The organic layers were washed with water×2, dried over MgSO$_4$, filtered, concentrated in vacuo, and purified by HPLC to give 180 mg (93% yield) of acid 241-(4-fluorophenyl)-1H-indazol-5-yl)(phenyl)methyl)butanoic acid. MS found: (M+H)$^+$=389.

(c)(d) 2-((1-(4-Fluorophenyl)-1H-indazol-5-yl)(phenyl)methyl)butanoic acid (60, mg, 0.154 mmol) was converted into the acid fluoride using the identical procedure to that for Synthetic Intermediate I above. A solution of 3-(1-(4-fluorophenyl)-1H-indazol-5-yl)-2-ethyl-3-phenylpropanoyl fluoride (0.32 mmol) in anhydrous THF (5 mL) at −78° C. was bubbled NH$_3$ (g) for 10 minutes. The reaction mixture was sealed and stirred at −78° C. for 15 min and at rt for 1 hr. Water (100 mL) was added, the reaction mixture was extracted with ethyl acetate (100 mL), dried (Na$_2$SO$_4$), and concentrated to give 3-(1-(4-fluorophenyl)-1H-indazol-5-yl)-2-ethyl-3-phenylpropanamide.

(e) To a stirred solution of the crude 3-(1-(4-fluorophenyl)-1H-indazol-5-yl)-2-ethyl-3-phenylpropanamide in anhydrous THF (10 mL) was added 1.0M lithium aluminum hydride in diethyl ether (2.0 mL, 2.0 mmol) portionwise at RT under nitrogen. After stirring at RT for 24 hr, the mixture was carefully quenched with MeOH, poured into brine (100 mL), extracted with ethyl acetate (2×100 mL), dried (Na$_2$SO$_4$) and concentrated to give 50 mg (88% yield, 3 steps) of 2-((1-(4-fluorophenyl)-1H-indazol-5-yl)(phenyl)methyl)butan-1-amine.

(f) 2-((1-(4-fluorophenyl)-1H-indazol-5-yl)(phenyl)methyl)butan-1-amine (28 mg, 0.075 mmol) was coupled with 3,3,3-trifluoropropanoic acid (18 mg, 0.1 mmol) using General Coupling Method B to give 11 mg (28% yield) of 2,2,2-trifluoro-N-(2-((1-(4-fluorophenyl)-1H-indazol-5-yl)(phenyl)methyl)butyl)ethanesulfonamide. MS found: (M+H)$^+$=520.

SCHEME J

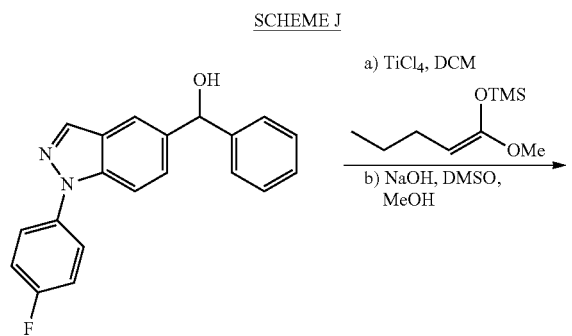

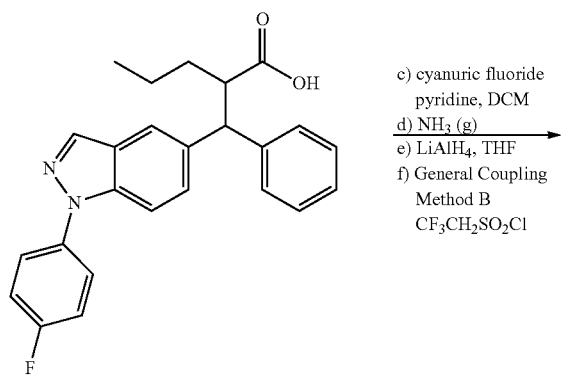

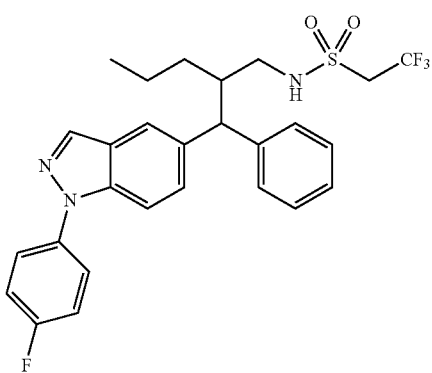

Example 99 was synthesized using the procedure outlined in Scheme J.

Example 99

2,2,2-Trifluoro-N-(2-((1-(4-fluorophenyl)-1H-indazol-5-yl)(phenyl)methyl)pentyl)ethanesulfonamide

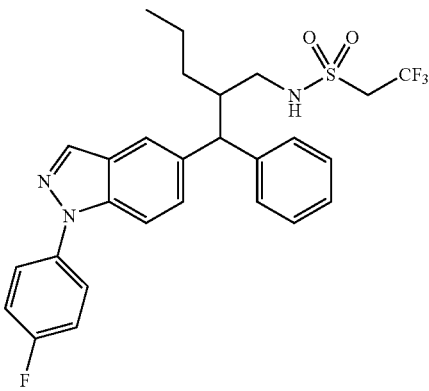

(a) To a solution of (1-(4-fluorophenyl)-1H-indazol-5-yl)(phenyl)methanol (158 mg, 0.5 mmol) and (1-methoxypent-1-enyloxy)trimethylsilane (16 mmol) which was prepared using General Silyl Ketene Acetal Method A in 10 mL of dry DCM was added TiCl$_4$ (0.5 mL of 1.0 M DCM solution, 0.5 mmol) and then stirred 1 h. The reaction was quenched with MeOH, poured into aqueous sodium bicarbonate and extracted 2× EtOAc. The organic layers were dried over MgSO$_4$, filtered, concentrated and purified on SiO$_2$ by MPLC using a EtOAc/hexane gradient to give 160 mg (77% yield) of methyl 2-((1-(4-fluorophenyl)-1H-indazol-5-yl)(phenyl)methyl)pentanoate. MS found: (M+H)$^+$=417.

(b) Methyl 2-((1-(4-fluorophenyl)-1H-indazol-5-yl)(phenyl)methyl)pentanoate was heated to 100° C. overnight in a mixture of 2 M NaOH/MeOH/DMSO (1:1:1). The next day, the reaction was cooled, acidified to pH 5 with HCl and extracted 2× EtOAc. The organic layers were washed with water×2, dried over MgSO$_4$, filtered, concentrated in vacuo, and purified by HPLC to give 140 mg (91% yield) of acid 2-((1-(4-fluorophenyl)-1H-indazol-5-yl)(phenyl)methyl)pentanoic acid. MS found: (M+H)$^+$=403.

(c)(d) 2-((1-(4-fluorophenyl)-1H-indazol-5-yl)(phenyl)methyl)pentanoic acid (50, mg, 0.124 mmol) was converted into the acid fluoride using the identical procedure to that for Synthetic Intermediate I above. A solution of 3-(1-(4-fluorophenyl)-1H-indazol-5-yl)-2-propyl-3-phenylpropanoyl fluoride (0.32 mmol) in anhydrous THF (5 mL) at −78° C. was bubbled NH$_3$ (g) for 10 minutes. The reaction mixture was sealed and stirred at −78° C. for 15 min and at rt for 1 hr. Water (100 mL) was added, the reaction mixture was extracted with ethyl acetate (100 mL), dried (Na$_2$SO$_4$), and concentrated to give 3-(1-(4-fluorophenyl)-1H-indazol-5-yl)-2-propyl-3-phenylpropanamide.

(e) To a stirred solution of the crude 3-(1-(4-fluorophenyl)-1H-indazol-5-yl)-2-propyl-3-phenylpropanamide in anhydrous THF (10 mL) was added 1.0M lithium aluminum hydride in diethyl ether (2.0 mL, 2.0 mmol) portionwise at RT under nitrogen. After stirring at RT for 24 hr, the mixture was carefully quenched with MeOH, poured into brine (100 mL), extracted with ethyl acetate (2×100 mL), dried (Na$_2$SO$_4$) and concentrated to give 45 mg (94% yield, 3 steps) of 2((1-(4-fluorophenyl)-1H-indazol-5-yl)(phenyl)methyl)pentan-1-amine.

(f) 2-((1-(4-fluorophenyl)-1H-indazol-5-yl)(phenyl)methyl)pentan-1-amine (28 mg, 0.075 mmol) was coupled with 3,3,3-trifluoropropanoic acid (18 mg, 0.1 mmol) using General Coupling Method B to give 11 mg (28% yield) of 2,2,2-trifluoro-N-(2-((1-(4-fluorophenyl)-1H-indazol-5-yl)(phenyl)methyl)butyl)ethanesulfonamide. MS found: (M+H)$^+$=520.

Example 100 was synthesized using the procedure outlined in Scheme K.

Example 100

2,2,2-Trifluoro-N-(3-(1-(4-fluorophenyl)-1H-indazol-5-yl)-2,3-diphenylpropyl)ethanesulfonamide

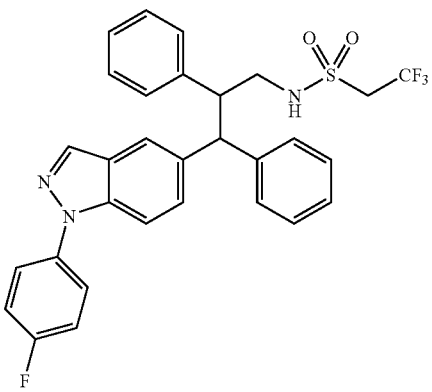

SCHEME K

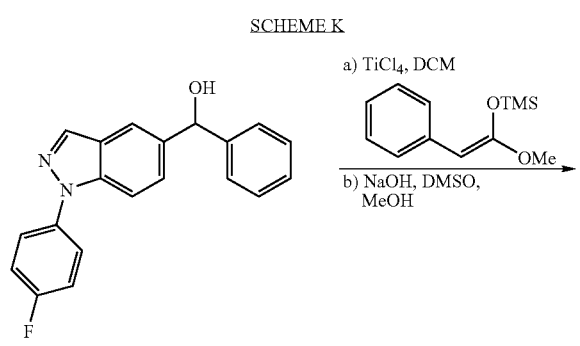

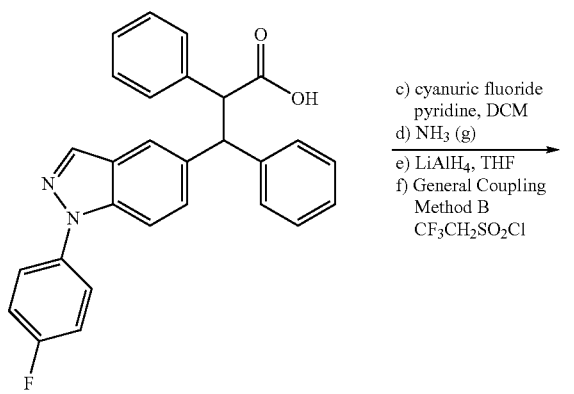

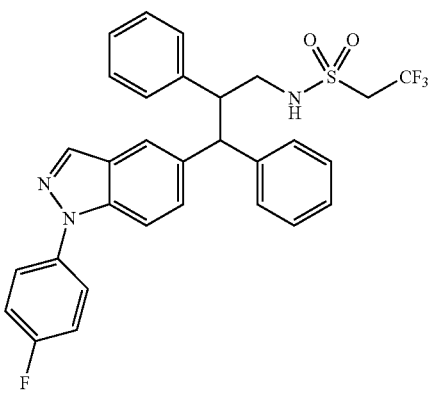

(a) To a solution of (1-(4-fluorophenyl)-1H-indazol-5-yl)(phenyl)methanol (318 mg, 1.0 mmol) and (1-methoxy-2-phenylvinyloxy)trimethylsilane (3 mmol) which was prepared using General Silyl Ketene Acetal Method A in 10 mL of dry DCM was added TiCl$_4$ (1.0 mL of 1.0 M DCM solution, 1.0 mmol) and then stirred 1 h. The reaction was quenched with MeOH, poured into aqueous sodium bicarbonate and extracted 2× EtOAc. The organic layers were dried over MgSO$_4$, filtered, concentrated and purified on SiO$_2$ by MPLC using a EtOAc/hexane gradient to give 376 mg (84% yield) of methyl 3-(1-(4-fluorophenyl)-1H-indazol-5-yl)-2,3-diphenylpropanoate. MS found: (M+H)$^+$=451.

(b) Methyl 3-(1-(4-fluorophenyl)-1H-indazol-5-yl)-2,3-diphenylpropanoate (346 mg, 0.77 mmol) was heated to 100 C overnight in a mixture of 2 M NaOH/MeOH/DMSO (1:1:1). The next day, the reaction was cooled, acidified to pH 5 with HCl and extracted 2× EtOAc. The organic layers were washed with water×2, dried over MgSO$_4$, filtered, concentrated in vacuo, and purified by HPLC to give 245 mg (73% yield) of acid 3-(1-(4-fluorophenyl)-1H-indazol-5-yl)-2,3-diphenylpropanoic acid. MS found: (M+H)$^+$=389.

(c)(d) 3-(1-(4-Fluorophenyl)-1H-indazol-5-yl)-2,3-diphenylpropanoic acid (80, mg, 0.154 mmol) was converted into the acid fluoride using the identical procedure to that for Synthetic Intermediate I above. A solution of 3-(1-(4-fluorophenyl)-1H-indazol-5-yl)-2,3-diphenylpropanoyl fluoride in anhydrous THF (5 mL) at −78° C. was bubbled NH$_3$ (g) for 10 minutes. The reaction mixture was sealed and stirred at −78° C. for 15 min and at rt for 1 hr. Water (100 mL) was added, the reaction mixture was extracted with ethyl acetate (100 mL), dried (Na$_2$SO$_4$), and concentrated to give 3-(1-(4-fluorophenyl)-1H-indazol-5-yl)-2,3-diphenylpropan-amide.

(e) To a stirred solution of the crude 3-(1-(4-fluorophenyl)-1H-indazol-5-yl)-2,3-diphenylpropanamide in anhydrous THF (10 mL) was added 1.0M lithium aluminum hydride in diethyl ether (2.0 mL, 2.0 mmol) portionwise at RT under nitrogen. After stirring at RT for 24 hr, the mixture was carefully quenched with MeOH, poured into brine (100 mL), extracted with ethyl acetate (2×100 mL), dried (Na₂SO₄) and concentrated to give 50 mg (65% yield, 3 steps) of 3-(1-(4-fluorophenyl)-1H-indazol-5-yl)-2,3-diphenylpropan-1-amine (f) 3-(1-(4-Fluorophenyl)-1H-indazol-5-yl)-2,3-diphenylpropan-1-amine (20 mg, 0.047 mmol) was coupled with 3,3,3-trifluoropropanoic acid (18 mg, 0.1 mmol) using General Coupling Method B to give 4 mg (28% yield) of 2,2,2-trifluoro-N-(2-((1-(4-fluorophenyl)-1H-indazol-5-yl)(phenyl)methyl)butyl)ethanesulfonamide. MS found: $(M+H)^+=568$.

Examples 101 to 106

Examples 101 to 106 in Table 5 below were prepared using the same method outlined in Scheme C and using the M-M$_a$-MgBr reagent shown in the table or in the given experimental. The ureas were made using General Coupling Method B.

TABLE 5

| Ex. | Name | Product Structure | M-M$_a$-MgBr | (M + H)+ |
|---|---|---|---|---|
| 101 | 1-tert-butyl-3-(3-(1-(4-fluorophenyl)-1H-indazol-5-yl)-2,2-dimethylpentyl)urea | | ethyl | 425 |
| 102 | 1-tert-butyl-3-(3-cyclopropyl-3-(1-(4-fluorophenyl)-1H-indazol-5-yl)-2,2-dimethylpropyl)urea | | cyclopropyl | 437 |
| 103 | 1-tert-butyl-3-(3-(1-(4-fluorophenyl)-1H-indazol-5-yl)-2,2,4-trimethylpentyl)urea | | isopropyl | 439 |

TABLE 5-continued
| Ex. | Name | Product Structure | M-M$_a$-MgBr | (M + H)+ |
|---|---|---|---|---|
| 104 | 1-tert-butyl-3-(3-(1-(4-fluorophenyl)-1H-indazol-5-yl)-2,2-dimethylhexyl)urea | 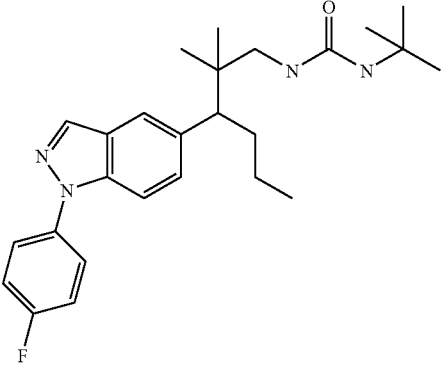 | propyl | 439 |
| 105 | 1-tert-butyl-3-(3-(1-(4-fluorophenyl)-1H-indazol-5-yl)-2,2-dimethylhex-5-enyl)urea | 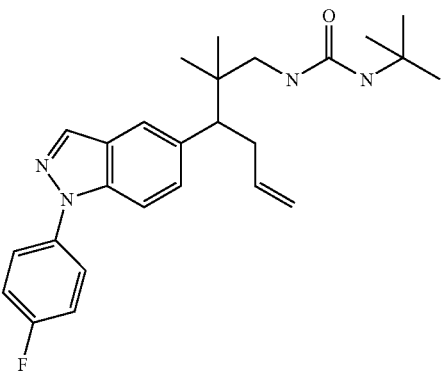 | allyl | 437 |
| 106 | 1-tert-butyl-3-(3-cyclopentyl-3-(1-(4-fluorophenyl)-1H-indazol-5-yl)-2,2-dimethylpropyl)urea | 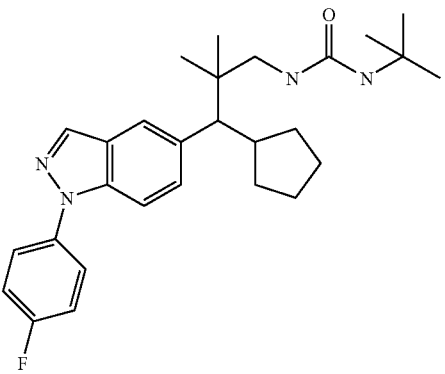 | cyclopentyl | 465 |

Example 107

1-tert-Butyl-3-(3-(1-(4-fluorophenyl)-1H-indazol-5-yl)-6-hydroxy-2,2-dimethylhexyl)urea

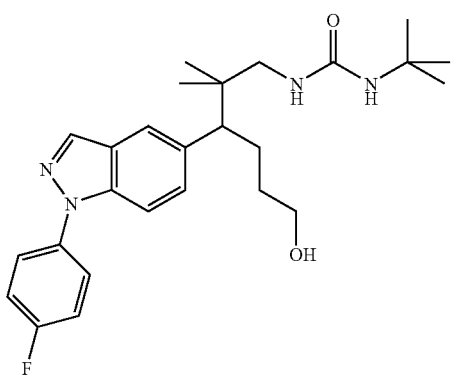

To a solution of 1-tert-butyl-3-(3-(1-(4-fluorophenyl)-1H-indazol-5-yl)-2,2-dimethylhex-5-enyl)urea (5.0 mg, 0.01 mmol) in anhydrous THF (2 mL) at 0 C was added 9-BBN (50 μL, 0.02 mmol) under nitrogen. Allowed reaction mixture to warm to RT and stirred overnight then added 10% NaOH solution (0.2 mL) and 30% H2O2 (1 mL). and stirred for 10 min. The reaction mixture was poured into a water (4 mL), extracted with ethyl acetate (2×10 mL), dried (Na₂SO₄) and purified by chromatography to give 3.2 mg (50% yield) of 1-tert-butyl-3-(3-(1-(4-fluorophenyl)-1H-indazol-5-yl)-6-hydroxy-2,2-dimethylhexyl)urea. MS found: (M+H)⁺=455.

Example 108

1-tert-Butyl-3-(4-cyclopropyl-3-(1-(4-fluorophenyl)-1H-indazol-5-yl)-2,2-dimethylbutyl)urea

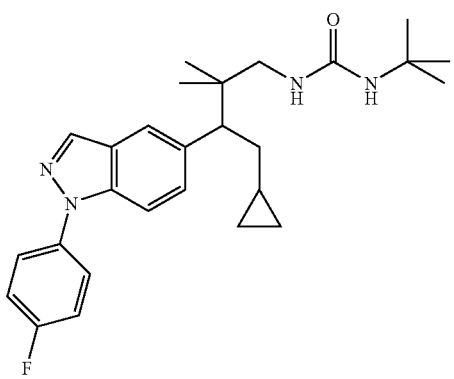

To a solution of 1-tert-butyl-3-(3-(1-(4-fluorophenyl)-1H-indazol-5-yl)-2,2-dimethylhex-5-enyl)urea (20 mg, 0.046 mmol) in anhydrous DCE (2 mL) at −10 C was added diethylzinc solution (0.46 mL, 0.46 mmol) and methyldiiodide (245 mg, 0.92 mmol) under nitrogen. Allowed reaction mixture to warm to RT and stirred overnight. The mixture was poured into sat NH4Cl, extracted with DCM (2×10 mL), dried (Na₂SO₄) and purified by HPLC to give 11 mg (50% yield) of 1-tert-butyl-3-(4-cyclopropyl-3-(1-(4-fluorophenyl)-1H-indazol-5-yl)-2,2-dimethylbutyl)urea. MS found: (M+H)⁺=451.

SCHEME L

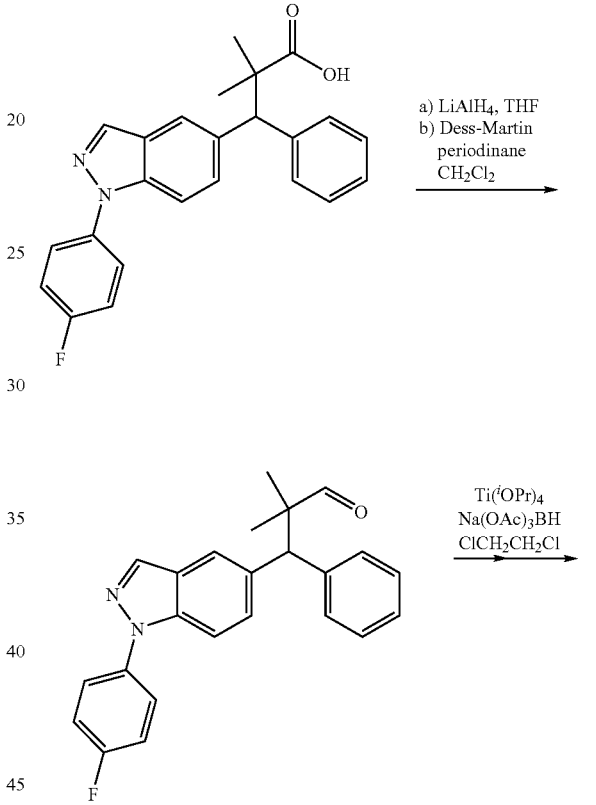

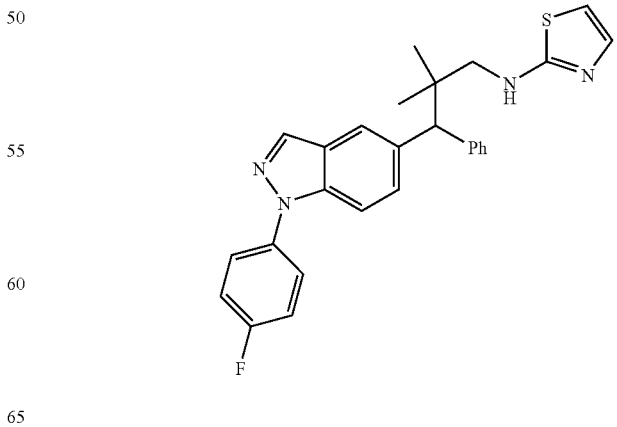

Example 109 was synthesized using the procedure outlined in Scheme L.

Example 109

N-(3-(1-(4-Fluorophenyl)-1H-indazol-5-yl)-2,2-dimethyl-3-phenylpropyl)-1,3,4-thiadiazol-2-amine

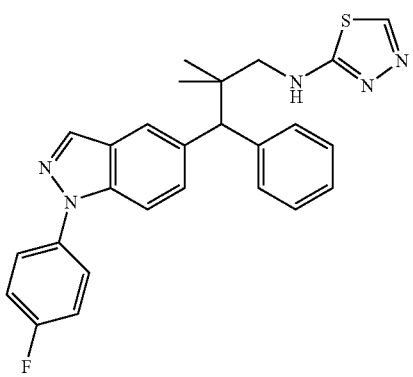

(a) To a solution of 3-(1-(4-fluorophenyl)-1H-indazol-5-yl)-2,2-dimethyl-3-phenylpropanoic acid (2.0 mg, 5.15 mmol) in anhydrous THF (20 mL) was added 1.0M lithium aluminum hydride in diethyl ether (10.0 mL, 10.0 mmol) portionwise at RT under nitrogen. After stirring at RT for 24 hr, the mixture was carefully quenched with MeOH, poured into a 1N sodium hydroxide solution (100 mL), extracted with ethyl acetate (2×100 mL), dried ($Na_2SO_4$) and concentrated to give 1.3 g (67% yield) of 3-(1-(4-fluorophenyl)-1H-indazol-5-yl)-2,2-dimethyl-3-phenylpropan-1-ol, the NMR spectrum of which was consistent with the desired structure.

(b) To a stirred solution of 3-(1-(4-fluorophenyl)-1H-indazol-5-yl)-2,2-dimethyl-3-phenylpropan-1-ol (1.3 g, 3.5 mmol) in $CH_2Cl_2$ (150 mL) was added Dess-Martin periodinane (2.12 g, 5.0 mmol) portionwise at RT under nitrogen. After stirring at RT for 24 hr, the mixture was poured into a 1N sodium hydroxide solution (100 mL), extracted with $CH_2Cl_2$ (100 mL), dried ($Na_2SO_4$) and concentrated. The crude residue was purified over silica gel eluting with EtOAc/hexanes (1:3) to give 1.03 g (79% yield) of 3-(1-(4-fluorophenyl)-1H-indazol-5-yl)-2,2-dimethyl-3-phenylpropanal, the NMR spectrum of which was consistent with the desired structure.

(c) To a stirred solution of 3-(1-(4-fluorophenyl)-1H-indazol-5-yl)-2,2-dimethyl-3-phenylpropanal (419 mg, 1.12 mmol) in $ClCH_2CH_2Cl$ (20 mL) was added 1,3,4-thiadiazol-2-amine (137 mg, 1.35 mmol) and titanium tetraisopropoxide (0.35 mL, 1.2 mmol) at RT under nitrogen. The reaction mixture was heated at 85° C. for 1 hr then sodium triacetoxyborohydride (318 mg, 1.5 mmol) was added and the reaction was heated at 85° C. for 4 hr. The reaction mixture was poured into a sat. sodium bicarbonate solution (100 mL), extracted with $CH_2Cl_2$ (100 mL), dried ($Na_2SO_4$) and concentrated. The final product was purified using HPLC to give 95 mg (19% yield) of N-(3-(1-(4-fluorophenyl)-1H-indazol-5-yl)-2,2-dimethyl-3-phenylpropyl)-1,3,4-thiadiazol-2-amine which showed consistent $^1$H-NMR spectra. MS found: $(M+H)^+$=458. NMR ($CDCl_3$) δ 11.3 (bs, 1H); 8.12 (s, 1H); 8.03 (s, 1H); 7.82 (s, 1H); 7.52-7.55 (m, 2H); 7.48 (s, 1H); 7.39-7.41 (d, 2H); 7.11-7.23 (m, 5H); 4.16 (s, 1H); 3.09-3.18 (q, 2H); 1.18 (s, 6H).

SCHEME M

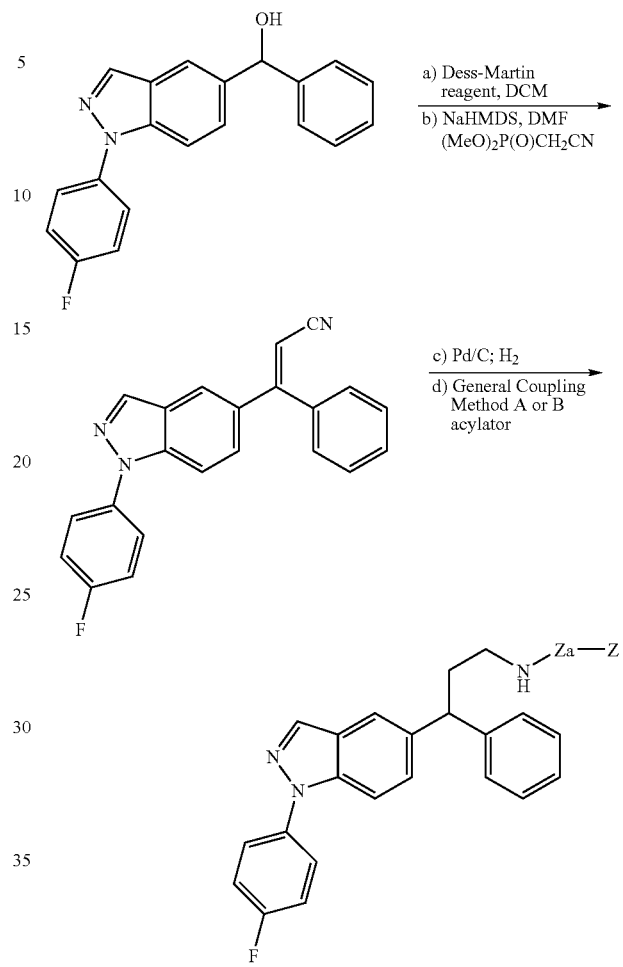

Examples 110, 111, and 112 were synthesized using the procedure outlined in Scheme M.

Example 110

2,2,2-Trifluoro-N-(3-(1-(4-fluorophenyl)-1H-indazol-5-yl)-3-phenylpropyl)ethanesulfonamide

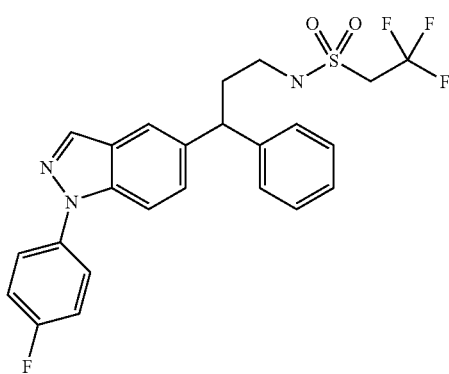

(a) (1-(4-Fluorophenyl)-1H-indazol-5-yl)(phenyl)methanol (Example 1(f)) (2.4 g, 7.54 mmol) was dissolved in 50 mL of DCM and treated with Dess Martin periodinane (3.2 g, 7.54 mmol) and stirred overnight. The next day, the reaction was extracted from 2 M NaOH with DCM (vigorous shaking)×3, dried over MgSO$_4$, filtered, and concentrated in vacuo. The crude material was filtered through a silica gel pad using EtOAc and concentrated to give (1-(4-fluorophenyl)-1H-indazol-5-yl)(phenyl)methanone (2.4 g, 100%). MS found: (M+H)$^+$=340.

(b) Diethyl(cyanomethyl)phosphonate (420 mg, 2.37 mmol) was dissolved in 10 mL anhydrous DMF and treated with sodium hexadimethylsilazane (2.4 mmol, 1 M in THF). (1-(4-fluorophenyl)-1H-indazol-5-yl)(phenyl)methanone (500 mg, 1.58 mmol) was added and the reaction was stirred for 16 hours. The following day, the cooled reaction was extracted from brine using ether×3 and the combined organic layers were dried over MgSO$_4$, filtered, and concentrated in vacuo. The residue was chromatographed on silica gel using 25% EtOAc in hexanes to give 3-(1-(4-fluorophenyl)-1H-indazol-5-yl)-3-phenylacrylonitrile (500 mg; 92%) of a 1.3:1 mixture of geometrical isomers as a clear oil. MS found: (M+H)$^+$=373.

(c)(d) 3-(1-(4-Fluorophenyl)-1H-indazol-5-yl)-3-phenylacrylonitrile (500 mg; 1.47 mmol) was dissolved in 20 mL MeOH and 4 mL 1 M HCl. 10% Pd on carbon (170 mg) was added and the reaction was hydrogenated in a Parr bottle over an atmosphere of 50 psi hydrogen for 16 h. The catalyst was filtered off and the solvent removed in vacuo to give pure 3-(1-(4-fluorophenyl)-1H-indazol-5-yl)-3-phenylpropan-1-amine (492 mg, 100%) as a yellow oil. MS found: (M+H)$^+$=376. 28 mg of this product (free base) was coupled to 2,2,2-trifluoroethanesulfonyl chloride using General Coupling Method B to give 20 mg (50%) of 2,2,2-trifluoro-N-(3-(1-(4-fluorophenyl)-1H-indazol-5-yl)-3-phenylpropyl)ethanesulfonamide. MS found: (M+H)$^+$=492.

Example 111

3,3,3-Trifluoro-N-(3-(1-(4-fluorophenyl)-1H-indazol-5-yl)-3-phenylpropyl)propanaide

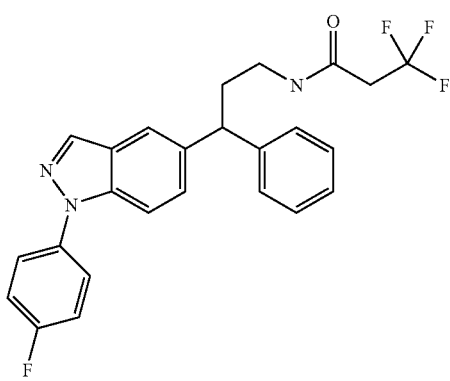

Prepared from 3-(1-(4-fluorophenyl)-1H-indazol-5-yl)-3-phenylpropan-1-amine (25 mg, 0.05 mmol) and 3,3,3-trifluoropropionic acid using General Coupling Method A to give 24 mg (97%) of 3,3,3-trifluoro-N-(3-(1-(4-fluorophenyl)-1H-indazol-5-yl)-3-phenylpropyl)propanamide. MS found: (M+H)$^+$=456.

Example 112

2,2,2-Trifluoro-N-(3-(1-(4-fluorophenyl)-1H-indazol-5-yl)-3-phenylpropyl)acetamide

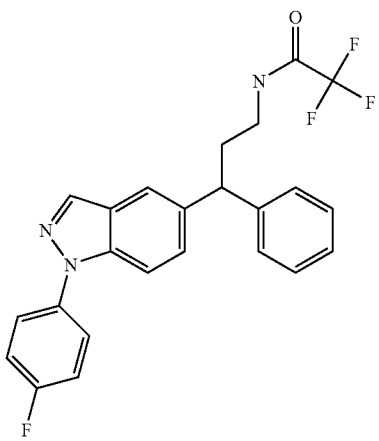

Prepared from 3-(1-(4-fluorophenyl)-1H-indazol-5-yl)-3-phenylpropan-1-amine TFA salt (25 mg, 0.05 mmol) by adding 2,2,2-trifluoroethanesulfonyl chloride under the General Coupling Method B conditions. Obtained 22 mg (82%) of 2,2,2-trifluoro-N-(3-(1-(4-fluorophenyl)-1H-indazol-5-yl)-3-phenylpropyl)acetamide. MS found: (M+H)$^+$=442.

SCHEME N

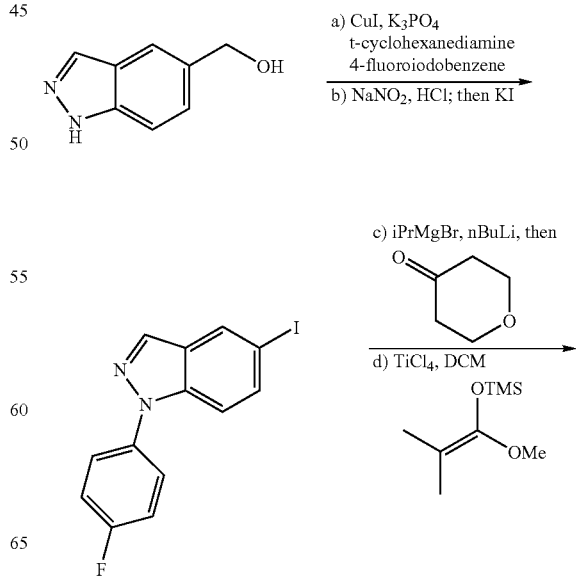

183
-continued

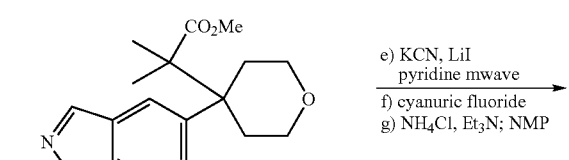

e) KCN, LiI pyridine mwave
f) cyanuric fluoride
g) NH₄Cl, Et₃N; NMP

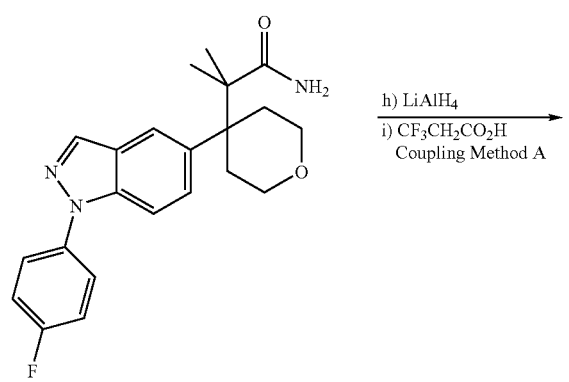

h) LiAlH₄
i) CF₃CH₂CO₂H
Coupling Method A

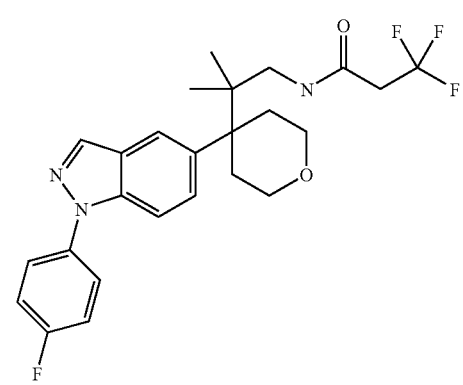

Example 113 was synthesized using the procedure outlined in Scheme N.

Example 113

3,3,3-Trifluoro-N-(2-(4-(1-(4-fluorophenyl)-1H-indazol-5-yl)tetrahydro-2H-pyran-4-yl)-2-methyl-propyl)propanamide

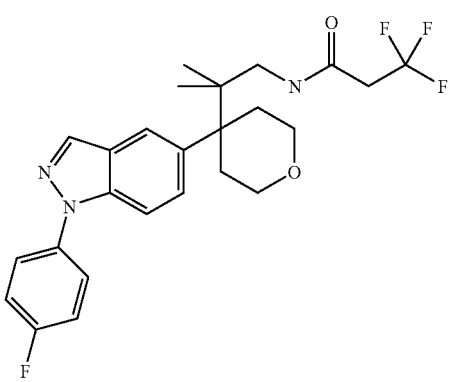

(a) Commercially available 5-aminoindazole (15 g, 113 mmol) was dissolved in 100 mL dry dioxane in a stainless steel pressure bottle followed by the addition of trans-1,2-diaminocyclohexane (6.4 g, 56 mmol), CuI (2.1 g, 11.3 mmol), K₃PO₄ (43 g, 203 mmol), and 1-fluoro-4-iodobenzene (27.5 g, 11.3 mmol). The reactor was sealed and heated at 120 C for 72 h under a blanket of N2. The reaction was filtered through a large SiO2 plug on a fitted funnel using EtOAc until the eluent ran clear (~1 L). The solution was concentrated in vacuo and the dark brown solid was taken up in hot EtOAc (~150 mL) and hexane was added to induce precipitation. The dark black solid was filtered and dried under vacuum to give 28 g (73%) of pure N1-(4-fluorophenyl)-5-aminoindazole. MS found: (M+H)⁺=228.

(b) To N1-(4-fluorophenyl)-5-aminoindazole (25.6 g, 113 mmol) suspended in 500 mL 6 M HCl and cooled to 0° C. was added a solution of sodium nitrite (8.2 g, 119 mmol) dissolved in 75 mL water, portionwise. After 3 h, potassium iodide (22.5 g, 136 mmol) dissolved in 80 mL water was added and the reaction was stirred overnight. The next day, the reaction was transferred to a beaker and carefully quenched by adding solid sodium carbonate. After neutralization and addition of water, the aqueous phase was extracted 4× EtOAc. The combined organic extracts were dried over MgSO₄, filtered, concentrated, and filtered from hot EtOAc. The filtrate was concentrated and purified on a 330 g SiO₂ MPLC column using DCM. Obtained 13.2 g of 1-(4-fluorophenyl)-5-iodo-1H-indazole (39%). MS found: (M+H)⁺=339.

(c) 1-(4-Fluorophenyl)-5-iodo-1H-indazole (350 mg, 1.0 mmol) was dissolved in 10 mL dry THF and treated with isopropylmagnesium bromide (1.6 mL of 1 M THF solution) and then BuLi (1.6 M in hexanes, 0.72 mmol, 1.1 mmol) at room temp. After 30 min, tetrahydro-4H-pyran-4-one (270 mg, 2.7 mmol) was added. After 2 h, the reaction was quenched with water, then 1 M HCl, and extracted 2× EtOAc. The organic layers were dried over MgSO₄, filtered, concentrated, and the residue was purified using 1:1 EtOAc/hexanes to give 125 mg (39%) of 4-(1-(4-fluorophenyl)-1H-indazol-5-yl)tetrahydro-2H-pyran-4-ol as a clear oil that solidified upon standing. (M+H)$^+$=313.

(d) To 4-(1-(4-fluorophenyl)-1H-indazol-5-yl)tetrahydro-2H-pyran-4-ol (125 mg, 0.40 mmol) in 5 mL of DCE was added TiCl4 (0.44 mmol; 0.44 mL of 1 M solution in DCM). A precipitate immediately formed. The reaction was concentrated in vacuo to approx 1 mL volume and treated with 1-methoxy-2-methyl-1-(trimethylsiloxy)propene (0.23 mL, 1.2 mmol) and the reaction became homogeneous and was complete. The reaction was quenched with NaHCO3, extracted 4× EtOAc, and combined organic layers were dried over MgSO$_4$, filtered, and concentrated. The residue was purified by SiO2 chromatography using 25% EtOAc in hexanes to give methyl 2-(4-(1-(4-fluorophenyl)-1H-indazol-5-yl)tetrahydro-2H-pyran-4-yl)-2-methylpropanoate (155 mg, 99%). MS found: (M+H)$^+$=397.

(e) Methyl 2-(4-(1-(4-fluorophenyl)-1H-indazol-5-yl)tetrahydro-2H-pyran-4-yl)-2-methylpropanoate (155 mg, 0.40 mmol) was dissolved in 2.5 mL pyridine in a microwave reactor and KCN (104 mg, 1.6 mmol) and LiI (214 mg, 1.6 mmol) were added. The reactor was sealed and heated to 170° C. for 60 minutes. The reaction was purified directly by HPLC to give 2-(4-(1-(4-fluorophenyl)-1H-indazol-5-yl)tetrahydro-2H-pyran-4-yl)-2-methylpropanoic acid (100 mg, 67%). (M+H)$^+$=383.

(f)(g) 2-(4-(1-(4-Fluorophenyl)-1H-indazol-5-yl)tetrahydro-2H-pyran-4-yl)-2-methylpropanoic acid (50 mg, 0.13 mmol) was dissolved in 5 mL DCM, 32 uL pyridine, and treated with 27 uL cyanuric fluoride. After 1 h, the reaction was extracted from NaHCO$_3$ with EtOAc×3. The combined organic layers were dried over MgSO$_4$, filtered, concentrated and taken up in 2 mL NMP and treated with triethylamine (100 uL) and NH4Cl (50 mg). The reaction was purified by HPLC to give 23 mg of 2-(4-(1-(4-fluorophenyl)-1H-indazol-5-yl)tetrahydro-2H-pyran-4-yl)-2-methylpropanamide. (M+H)$^+$=382.

(h)(i) 2-(4-(1-(4-Fluorophenyl)-1H-indazol-5-yl)tetrahydro-2H-pyran-4-yl)-2-methylpropanamide (23 mg, 0.06 mmol) in 3 mL THF was treated with LiAlH$_4$ (0.2 mL of 1.0 M solution in THF) and stirred for 18 h. The reaction was quenched with EtOAc, TFA was added, and the reaction was purified by HPLC to give 2-(4-(1-(4-fluorophenyl)-1H-indazol-5-yl)tetrahydro-2H-pyran-4-yl)-2-methylpropan-1-amine. (M+H)$^+$=368. This material was coupled to 3,3,3-trifluoropropionic acid using General Coupling Method A. After 16 h, the reaction was purified by HPLC to give 6 mg of 3,3,3-trifluoro-N-(2-(4-(1-(4-fluorophenyl)-1H-indazol-5-yl)tetrahydro-2H-pyran-4-yl)-2-methylpropyl)propanamide. (M+H)$^+$=478.

SCHEME O

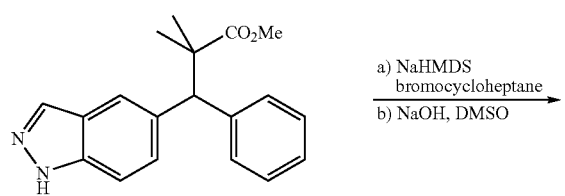

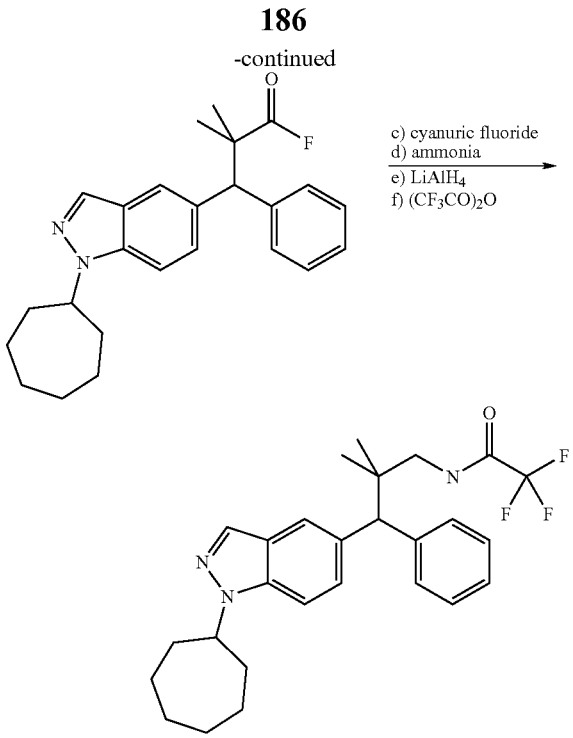

Example 114 was synthesized using the procedure outlined in Scheme O.

Example 114

N-(3-(1-Cycloheptyl-1H-indazol-5-yl)-2,2-dimethyl-3-phenylpropyl)-2,2,2-trifluoroacetamide

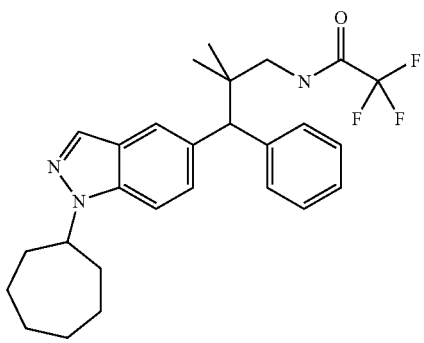

(a) Methyl 3-(1H-indazol-5-yl)-2,2-dimethyl-3-phenylpropanoate (500 mg, 1.62 mmol, prepared in Synthetic Intermediate III(c)) was dissolved in 5 mL DMSO and NaHMDS (2.4 mL, 2.4 mmol, 1.0 M in THF) was added followed by bromocycloheptane (446 uL, 3.25 mmol). The reaction was heated overnight at 85° C. The reaction was quenched with TFA and purified by HPLC to give methyl 3-(1-cycloheptyl-1H-indazol-5-yl)-2,2-dimethyl-3-phenylpropanoate (393 mg, 60%). (M+H)$^+$=405.

(b) Methyl 3-(1-cycloheptyl-1H-indazol-5-yl)-2,2-dimethyl-3-phenylpropanoate (393 mg, 0.97 mmol) was hydrolyzed by heating with 10 equiv NaOH in 3:1 DMSO/MeOH (10 mL). Purified by HPLC to give 393 mg of 3-(1-cycloheptyl-1H-indazol-5-yl)-2,2-dimethyl-3-phenylpropanoic acid. (M+H)$^+$=391.

(c)(d)(e)(f) 3-(1-Cycloheptyl-1H-indazol-5-yl)-2,2-dimethyl-3-phenylpropanoic acid (393 mg, 1 mmol) was dissolved in 20 mL DCM and treated with 130 mL pyridine and 127 uL of cyanuric fluoride and stirred overnight. The reaction was extracted from 1 M HCl with EtOAc×3. The combined organic layers were dried over $MgSO_4$, filtered, concentrated, and then taken up in THF (20 mL), cooled to −78° C. and ammonia gas was bubbled in for 1 min. The reaction was allowed to warm to rt. Quantitative conversion to 3-(1-cycloheptyl-1H-indazol-5-yl)-2,2-dimethyl-3-phenylpropanamide. $(M+H)^+$=390. This compound was dissolved in 15 mL THF and treated with LiAlH4 (4 mL, 4 mmol, 1 M in THF) and stirred for 3 h. The reaction was quenched with EtOAc and then 5 mL 1 M NaOH. After stirring 30 min, the reaction was extracted from brine 4× EtOAc. The combined organic layers were dried over $MgSO_4$, filtered, and concentrated to give 3-(1-cycloheptyl-1H-indazol-5-yl)-2,2-dimethyl-3-phenylpropan-1-amine. $(M+H)^+$=376. This material was dissolved in 3 mL DCM and treated with 0.2 mL trifluoroacetic anhydride. After 3 h, the reaction was rotovapped down and purified by HPLC to give N-(3-(1-cycloheptyl-1H-indazol-5-yl)-2,2-dimethyl-3-phenylpropyl)-2,2,2-trifluoroacetamide (182 mg, 38% for four steps). $(M+H)^+$=472.

SCHEME P
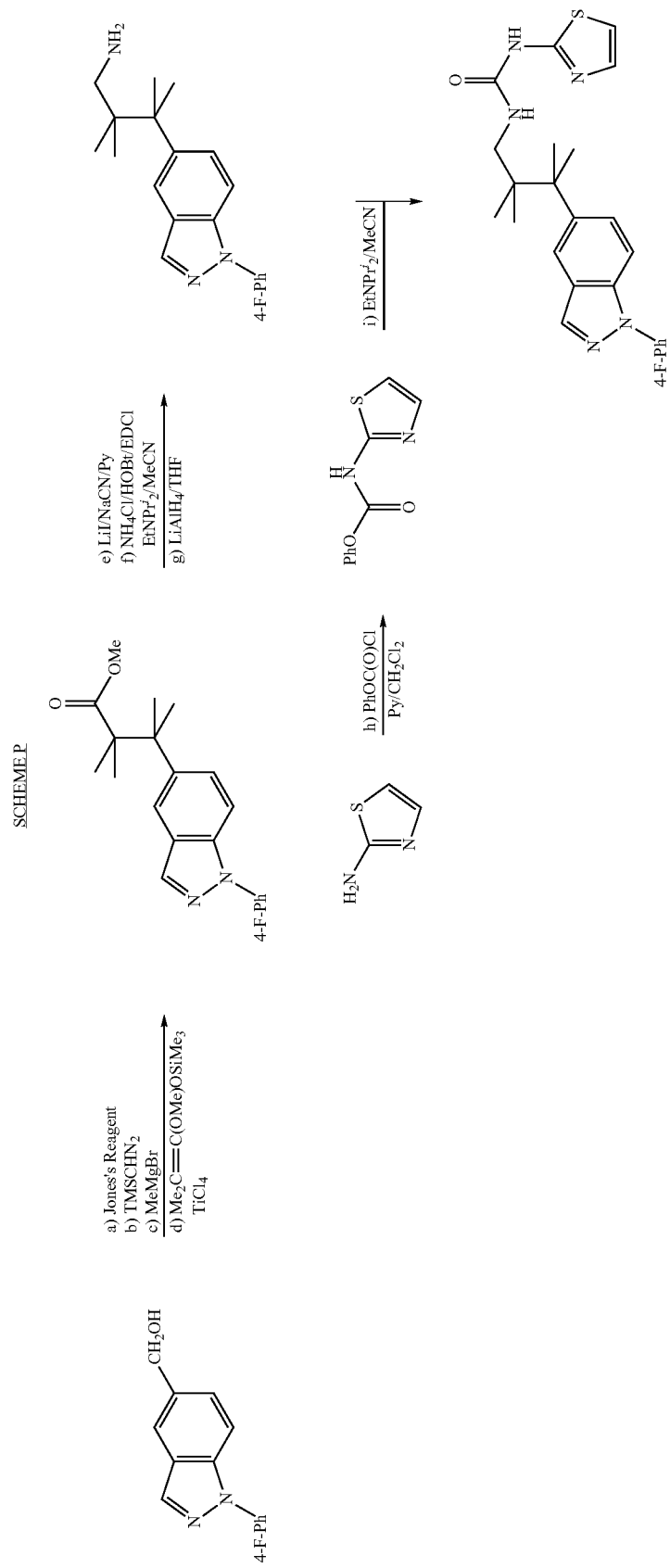

Examples 115 to 118 in Table 6 were synthesized using the procedure outlined in Scheme P.

Example 115

1-(3-(1-(4-Fluorophenyl)-1H-indazol-5-yl)-2,2,3-trimethylbutyl)-3-(thiazol-2-yl)urea

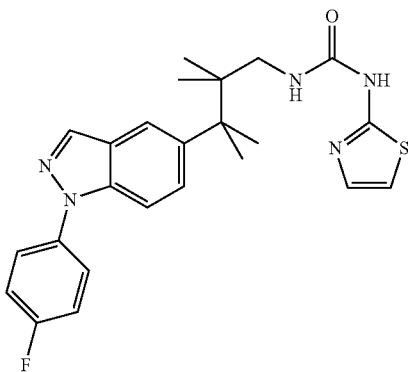

(a) To a stirred solution of (1-(4-fluorophenyl)-1H-indazol-5-yl)methanol (0.45 g, 1.9 mmol) in acetone (10 mL) was added Jones' reagent (3 mL) dropwise at 0° C. The reaction mixture was stirred at rt for 1 hr and concentrated under reduced pressure. Water was added to the residue and the solid that separates out was filtered, washed with water and dried to give 1-(4-fluorophenyl)-1H-indazole-5-carboxylic acid (0.43 g, 1.7 mmol, 89% yield) as a yellow solid.

(b) To a stirred suspension of the 1-(4-fluorophenyl)-1H-indazole-5-carboxylic acid (0.22 g, 0.81 mmol) in methanol (5 mL), THF (5 mL), and dichloromethane (5 mL) was added (trimethylsilyl)diazomethane solution (2M in diethyl ether, 1 mL, 2 mmol) dropwise at rt. The reaction mixture was stirred at rt for 1 hr and carefully quenched by the slow addition of acetic acid. Concentration under reduced pressure and titration with methanol gave methyl 1-(4-fluorophenyl)-1H-indazole-5-carboxylate (0.16 g, 0.59 mmol, 73% yield) as a white solid.

(c) To a suspension of methyl 1-(4-fluorophenyl)-1H-indazole-5-carboxylate (84 mg, 0.31 mmol) in anhydrous THF (5 mL) was added methylmagnesium bromide (3M solution in diethyl ether, 1 mL, 3 mmol) dropwise at rt under argon. The reaction mixture was stirred at rt for 1 hr and carefully quenched by the slow addition of saturated aqueous ammonium chloride solution (10 mL). The reaction mixture was extracted with ethyl acetate (10 mL), dried ($Na_2SO_4$), concentrated and purified by silica gel flash chromatography to give 2-(1-(4-fluorophenyl)-1H-indazol-5-yl)propan-2-ol (84 mg, 0.31 mmol, 100% yield) as a syrup.

(d) To a stirred solution of 2-(1-(4-fluorophenyl)-1H-indazol-5-yl)propan-2-ol (82 mg, 0.30 mmol) and (1-methoxy-2-methylprop-1-enyloxy)trimethylsilane (0.5 mL) in anhydrous dichloromethane (3 mL) was added titanium(IV) tetrachloride (1M solution in toluene, 1.2 mL, 1.2 mmol) dropwise at 0° C. under argon. The reaction mixture was stirred at 0° C. for 1 hr and rt for 1 hr before being quenched by the slow addition of saturated aqueous sodium bicarbonate solution. The reaction mixture was filtered through a pad of celite that was then washed with ethyl acetate (10 mL). The ethyl acetate layer was separated and the aqueous layer was reextracted with ethyl acetate (10 mL). The combined ethyl acetate layers were dried ($Na_2SO_4$), concentrated and purified by silica gel flash chromatography to give methyl 3-(1-(4-fluorophenyl)-1H-indazol-5-yl)-2,2,3-trimethylbutanoate (100 mg, 0.28 mmol, 94% yield) as a white solid.

(e) A mixture of methyl 3-(1-(4-fluorophenyl)-1H-indazol-5-yl)-2,2,3-trimethylbutanoate (330 mg, 0.93 mmol), lithium iodide (500 mg, 3.7 mmol), sodium cyanide (180 mg, 3.7 mmol), and pyridine (3 mL) was heated in CEM Explorer microwave reactor under nitrogen at 170° C. for 30 min. The reaction mixture was concentrated in vacuo, mixed with water (10 mL) and ethyl acetate (10 mL), and acidified with 10% aqueous citric acid solution to pH=4. The aqueous layer was separated and extracted with ethyl acetate (2×10 mL). The combined organic solutions were dried ($Na_2SO_4$) and concentrated to give 3-(1-(4-fluorophenyl)-1H-indazol-5-yl)-2,2,3-trimethylbutanoic acid (310 mg, 0.91 mmol, 98% yield) that was used as such for the subsequent step without further purification.

(f) To a stirred mixture of 3-(1-(4-fluorophenyl)-1H-indazol-5-yl)-2,2,3-trimethylbutanoic acid (230 mg; 0.68 mmol), ammonium chloride (180 mg, 3.4 mmol), 1-hydroxy-7-azabenzotriazole (92 mg, 0.68 mmol), anhydrous acetonitrile (5 mL), and N-(3-dimethylaminopropyl)-N'-ethylcarbodiimide hydrochloride (325 mg, 1.7 mml) was added diisopropylethylamine (0.47 mL, 2.7 mmol). The mixture was stirred under nitrogen at rt for 22 hr before concentrated in vacuo. The residue was mixed with saturated aqueous sodium bicarbonate solution (15 mL) and extracted with dichloromethane (2×10 mL). The combined dichloromethane extracts were dried ($Na_2SO_4$). Flash chromatography (SiO2 Column, 10-100% ethyl acetate in hexanes) gave 3-(1-(4-fluorophenyl)-1H-indazol-5-yl)-2,2,3-trimethylbutanamide (169 mg, 0.50 mmol, 74% yield) as a white solid.

(g) To a stirred solution of 3-(1-(4-fluorophenyl)-1H-indazol-5-yl)-2,2,3-trimethylbutanamide (159 mg, 0.47 mmol) in anhydrous THF (5 mL) was added a solution of LAH (1 M in diethylether, 1 mL, 1 mmol) under nitrogen at 0° C. The mixture was stirred at the same temperature for 1 hr and at rt for 22 hr. After an aqueous solution of sodium hydroxide (1 M, 10 mL) was added slowly, the mixture was stirred for 0.5 hr and filtered through a pad of celite that was then rinsed with dichloromethane. The filtrate was extracted with dichloromethane (4×10 mL). The combined extracts were dried ($Na_2SO_4$) and concentrated in vacuo to give 3-(1-(4-fluorophenyl)-1H-indazol-5-yl)-2,2,3-trimethylbutan-1-amine (173 mg; 0.53 mmol, 110% yield) as a yellow foam solid that was used as such without further purification.

(h) To a stirred mixture of 2-aminothiazole (2 g, 20 mmol), pyridine (10 mL), and anhydrous dichloromethane (20 mL) was added phenyl chloroformate (3 mL, 24 mmol) under argon at 0° C. The mixture was stirred at the same temperature for 5 min and at rt overnight before saturated aqueous sodium bicarbonate solution (30 mL) was added slowly. After mixed with heptanes (30 mL), the mixture was stirred for 30 min. The solid was filtered, washed with water (3×3 mL) and then diethylether (3×3 mL), and dried to give phenyl thiazol-2-ylcarbamate (3.4 g, 15 mmol, 75% yield) as an off-white solid.

(i) A mixture of 3-(1-(4-fluorophenyl)-1H-indazol-5-yl)-2,2,3-trimethylbutan-1-amine (10 mg, 0.031 mmol), phenyl thiazol-2-ylcarbamate (15 mg, 0.068 mmol), diisopropylethylamine (0.1 mL), and anhydrous acetonitrile (0.1 mL) was stirred under nitrogen at 80° C. till the reaction completed (ca 30 min) The mixture was dissolved in methanol and TFA. Purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave the title compound (4 mg, 0.009 mmol, 29% yield) as a white solid. MS found: (M+H)+=452. $^1$H-NMR (400 MHz, CHLOROFORM-d) δ ppm 8.16 (s, 1 H) 7.79 (s, 1 H) 7.69 (dd, J=8.90, 4.83 Hz, 2 H) 7.60 (d, J=9.10 Hz, 1 H) 7.52 (dd, J=9.10, 1.70 Hz, 1 H) 7.21-7.31 (m, 3 H) 6.91 (d, J=4.07 Hz, 1 H) 5.56 (t, J=6.00 Hz, 1 H) 3.28 (d, J=6.10 Hz, 2 H) 1.52 (s, 6 H) 0.96 (s, 6 H).

Examples 116 to 118

The compounds in Table 6 were prepared using the same procedure as outlined in Scheme P using the acylating agent in the table.

TABLE 6

| Ex. | Name | Product Structure | Acylating Agent | Coupling Method | [M + H]+ |
|---|---|---|---|---|---|
| 116 | 1-(3-(1-(4-fluorophenyl)-1H-indazol-5-yl)-2,2,3-trimethylbutyl)-3-(pyridin-2-yl)urea | | pyridyl-2-isocyanate | C | 446 |
| 117 | 1-ethyl-3-(3-(1-(4-fluorophenyl)-1H-indazol-5-yl)-2,2,3-trimethylbutyl)urea | | ethylisocyanate | B | 397 |
| 118 | 1-(3-(1-(4-fluorophenyl)-1H-indazol-5-yl)-2,2,3-trimethylbutyl)-3-isopropylurea | | isopropylisocyanate | B | 411 |

Examples 119 to 120 were synthesized using the procedures outlined in Scheme Q.

Example 119

4-(1-(4-Fluorophenyl)-1H-indazol-5-yl)-3,3-dimethyl-4-phenylbutan-2-ol

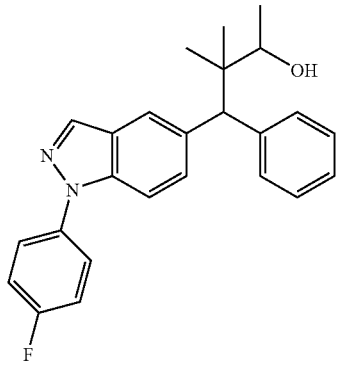

(a) To a solution of 3-(1-(4-fluorophenyl)-1H-indazol-5-yl)-2,2-dimethyl-3-phenylpropanal (from Ex 116(b), 25 mg, 0.067 mmol) in THF (1 ml) at 0° C. was added a solution of 1.4 M methylmagnesium bromide in 1 ml of THF (1.4 M) dropwise. After 1 hr, the reaction was quenched with sat. NH$_4$Cl and was extracted with ethyl acetate. The organic phase was washed, dried over MgSO$_4$, filtered, and concentrated to give 4-(1-(4-fluorophenyl)-1H-indazol-5-yl)-3,3-dimethyl-4-phenylbutan-2-ol as a white solid (24 mg, 92% yield). It is a mixture of diastereomers in a 1:1 ratio. $^1$H NMR (400 MHz, MeOD) δ ppm 8.20 (1 H, d, J=5.09 Hz) 7.96 (1 H, d, J=9.16 Hz) 7.68-7.75 (2 H, m) 7.59-7.67 (2 H, m) 7.53 (2 H, dd, J=7.63, 2.54 Hz) 7.23-7.35 (4 H, m) 7.14-7.20 (1 H, m) 4.40 (1 H, s) 3.50-3.60 (1 H, m) 1.10 (3 H, 2 singlets,) 1.05 (3 H, s) 0.99 (3 H, 2 singlets). LC/MS (m/z) 389.3 [(M+1)$^+$]; HPLC Rt: 3.96 min.

Example 120

4-(1-(4-Fluorophenyl)-1H-indazol-5-yl)-3,3-dimethyl-4-phenylbutan-2-one

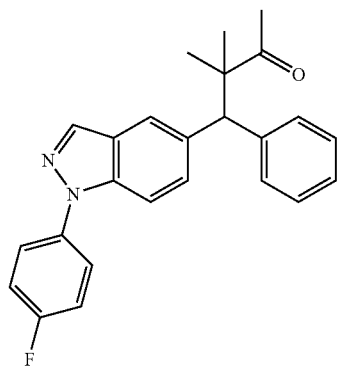

(b) 4-(1-(4-fluorophenyl)-1H-indazol-5-yl)-3,3-dimethyl-4-phenylbutan-2-ol (15 mg, 0.038 mmol) in DCM (1 ml) was treated with commercially available Dess-Martin periodinane (25 mg, 0.058 mmol). The reaction was complete in 45 minutes and was filtered through a plug of SiO$_2$ using DCM/hexane (3:1) and concentrated to give the crude product. The crude material was purified via chromatography on silica gel eluting with 14% ethyl acetate in hexane to afford 4-(1-(4-fluorophenyl)-1H-indazol-5-yl)-3,3-dimethyl-4-phenylbutan-2-one as a white foam (15 mg, quantitative yield). $^1$H NMR (400 MHz, MeOD) δ ppm 8.20 (1 H, s) 7.81 (1 H, s) 7.70 (2 H, dd, J=9.16, 4.58 Hz) 7.60 (1 H, d, J=8.65 Hz) 7.38 (1 H, dd, J=8.65, 1.53 Hz) 7.23-7.35 (6 H, m) 7.19 (1 H, t, J=7.12 Hz) 4.67 (1 H, s) 2.05 (3 H, s) 1.26 (6 H, d, J=5.09 Hz). LC/MS (m/z) 387.20 [(M+1)$^+$]; HPLC Rt: 3.758 min.

Examples 121 to 127

In a similar manner to Example 119, Examples 120 to 127 were prepared via the addition of the appropriate organometallic reagent to 3-(1-(4-fluorophenyl)-1H-indazol-5-yl)-2,2-dimethyl-3-phenylpropanal and subsequent oxidation to the ketone. Final compounds are mixture of diastereomers or enantiomers.

TABLE 7

| Ex. | Name | Structure | Rx-MgBr | [M + H]$^+$ |
|---|---|---|---|---|
| 121 | 3-(1-(4-fluorophenyl)-1H-indazol-5-yl)-2,2-dimethyl-1,3-diphenylprop an-1-ol | 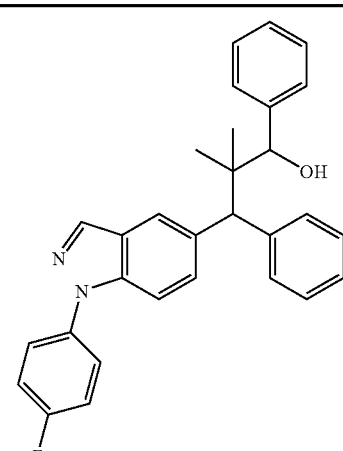 | Ph | 457 |

TABLE 7-continued
| Ex. | Name | Structure | Rx-MgBr | [M + H]+ |
|---|---|---|---|---|
| 122 | 1-cyclopropyl-3-(1-(4-fluorophenyl)-1H-indazol-5-yl)-2,2-dimethyl-3-phenylpropan-1-ol | 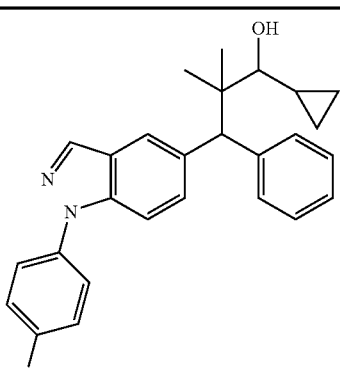 | isopropyl | 415 |
| 123 | 3-(1-(4-fluorophenyl)-1H-indazol-5-yl)-2,2-dimethyl-3-phenyl-1-(thiophen-2-yl)propan-1-ol | 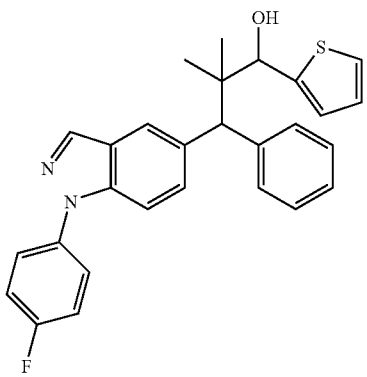 | 2-lithio-thiophene | 457 |
| 124 | 4-(1-(4-fluorophenyl)-1H-indazol-5-yl)-3,3-dimethyl-1,4-diphenylbutan-2-ol | 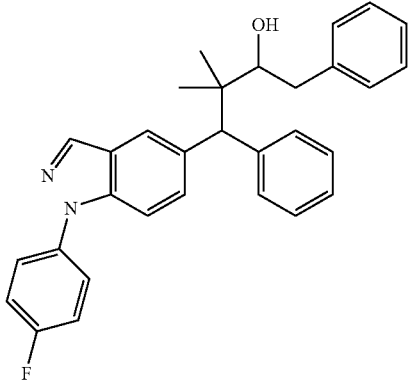 | benzyl | 465 |
| 125 | | 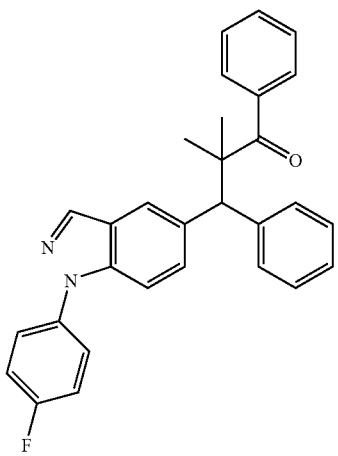 | — | 449 |

TABLE 7-continued

| Ex. | Name | Structure | Rx-MgBr | [M + H]+ |
|---|---|---|---|---|
| 126 | | 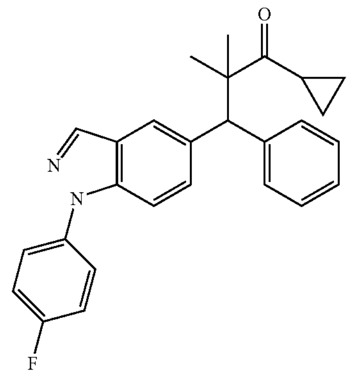 | — | 413 |
| 127 | | 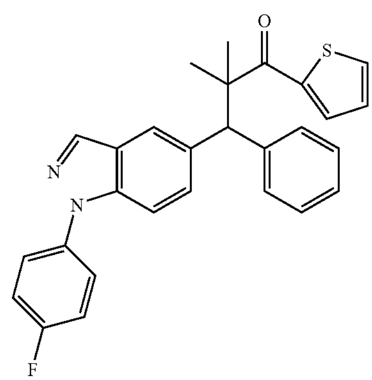 | — | 455 |

Example 128

1,1,1-Trifluoro-4-(1-(4-fluorophenyl)-1H-indazol-5-yl)-2,3,3-trimethyl-4-phenylbutan-2-ol

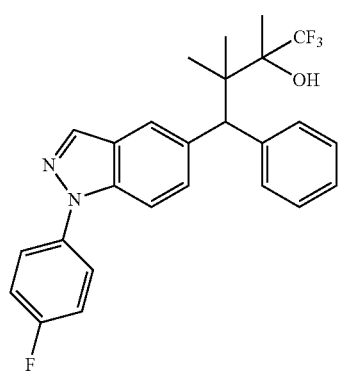

To a solution of the compound of Example 120, 4-(1-(4-fluorophenyl)-1H-indazol-5-yl)-3,3-dimethyl-4-phenylbutan-2-one (12 mg, 0.031 mmol) in THF (1 ml) at 0° C. was added trimethyl(trifluoromethyl)silane (22 mg, 0.155 mmol) and tetrabutylammonium fluoride in THF (0.031 ml, 0.031 mmol, 1M THF solution). The reaction mixture was stirred at 0° C. for 10 minutes, and then at room temperature for 45 minutes. Additional trimethyl(trifluoromethyl)silane (22 mg, 0.155 mmol) was added to the reaction mixture, after which stirring was continued for 2 hours. The reaction was quenched with saturated NH$_4$Cl and extracted with ethyl acetate. The organic phase was washed with brine, dried over MgSO$_4$ and concentrated to give the crude product. The crude material was purified via chromatography on silica gel eluting with 10% ethyl acetate in hexane to afford the compound of Example 135 as a white solid (10 mg, 71% yield). It is a mixture of diastereomers in 1:1 ratio. $^1$H NMR (400 MHz, MeOD) δ ppm 8.17 (1 H, s) 7.98 (1 H, d, J=16.79 Hz) 7.68 (3 H, dd, J=8.90, 4.83 Hz) 7.58 (2 H, d, J=8.14 Hz) 7.54 (1 H, d, J=7.63 Hz) 7.20-7.33 (4 H, m) 7.12 (1 H, t, J=7.12 Hz) 4.55 (1 H, d, J=5.09 Hz) 1.31 (3 H, 2 singlets) 1.22 (3 H, 2 singlets) 1.13 (3 H, 2 singlets). LC/MS (m/z) 387.20 [(M+H)+]; HPLC Rt: 3.758 min.

Example 129

1,1,1-Trifluoro-4-(1-(4-fluorophenyl)-1H-indazol-5-yl)-3,3-dimethyl-2,4-diphenylbutan-2-ol

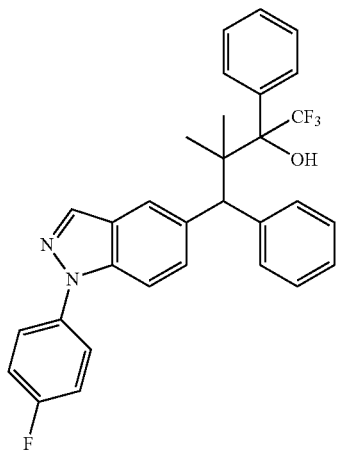

This compound was prepared from Example 125 using the same procedure as used for Example 135. (M+H)⁺=472.

Example 130

1,1,1-Trifluoro-4-(1-(4-fluorophenyl)-1H-indazol-5-yl)-3,3-dimethyl-4-phenyl-2-(thiophen-2-yl)butan-2-ol

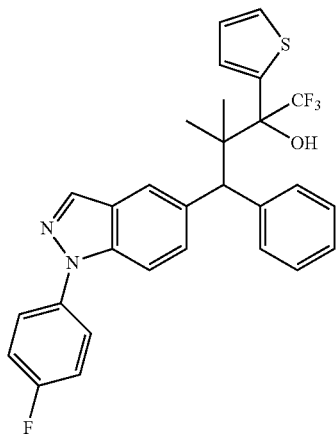

This compound was prepared from Example 127 using the same procedure as used for Example 135. (M+H)⁺=472.

Example 131

1,1,1-Trifluoro-4-(1-(4-fluorophenyl)-1H-indazol-5-yl)-3,3-dimethyl-4-phenylbutan-2-one

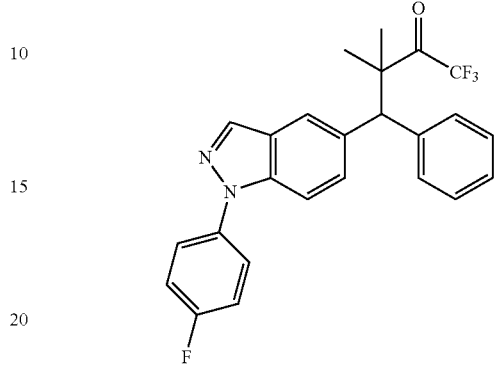

A solution of 3-(1-(4-fluorophenyl)-1H-indazol-5-yl)-2,2-dimethyl-3-phenylpropanal (from Ex 109(b), (140 mg, 0.376 mmol) in THF (3 ml) at 0° C. was added trimethyl(trifluoromethyl)silane (267 mg, 1.88 mmol) and tetrabutyl-ammonium fluoride in THF (0.376 ml, 0.376 mmol, 1M THF solution). The reaction mixture was stirred at 0° C. for 30 minutes, and then at room temperature overnight. After quenching with 4N HCl, the reaction was stirred for 30 minutes and was extracted with ethyl acetate. The organic phase was washed with brine, dried over MgSO₄ and concentrated to give the crude 1,1,1-trifluoro-4-(1-(4-fluorophenyl)-1H-indazol-5-yl)-3,3-dimethyl-4-phenylbutan-2-ol. The crude alcohol in DCM (1 ml) was treated with commercially available Dess-Martin periodinane (187 mg, 0.440 mmol). The reaction was complete in 45 minutes and was filtered through a plug of SiO₂ using DCM and concentrated to give the crude product. The crude material was purified via chromatography on silica gel eluting with 10% ethyl acetate in hexane to afford the compound of Example 6 as a colorless viscous oil (90 mg, 70% yield). ¹H NMR (400 MHz, MeOD) δ ppm 8.21 (1 H, s) 7.85 (1 H, s) 7.70 (2 H, dd, J=9.16, 4.58 Hz) 7.63 (1 H, d, J=8.65 Hz) 7.43 (1 H, dd, J=8.90, 1.78 Hz) 7.37 (2 H, d, J=7.12 Hz) 7.27-7.33 (4 H, m) 7.22 (1 H, t, J=7.12 Hz) 4.80 (1 H, s) 1.43 (6 H, d, J=5.09 Hz). LC/MS (m/z) 441.24 [(M+H)⁺]; HPLC Rt: 4.066 min.

Example 132

3-(1-(4-Fluorophenyl)-1H-indazol-5-yl)-2,2-dimethyl-3-phenylpropyl 2,2,2-trifluoroethylcarbamate

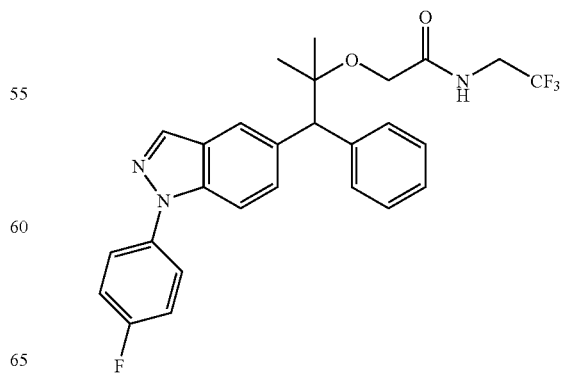

3-(1-(4-Fluorophenyl)-1H-indazol-5-yl)-2,2-dimethyl-3-phenylpropan-1-ol (prepared from LiAlH4 reduction of methyl 3-(1-(4-fluorophenyl)-1H-indazol-5-yl)-2,2-dimethyl-3-phenylpropanoate in Example 1(g)) (37 mg) in THF (1 ml) was treated with carbonyl diimidazole (29 mg, 0.176 mmol) at room temperature overnight. To the reaction solution was added 2,2,2-trifluoroethanamine (26 mg, 0.264 mmol). The reaction was heated at 50° C. for 14 hours. Additional 2,2,2-trifluoroethanamine 26 mg, 0.264 mmol) was added followed by addition of N,N-dimethylpyridin-4-amine (10 mg, 0.080 mmol), after which stirring was continued for 14 hours. The reaction was concentrated. The crude material was purified via chromatography on silica gel eluting with 10% ethyl acetate in hexane to afford the compound of Example 14 (4 mg, 10% yield). $^1$H NMR (400 MHz, MeOD) δ ppm 8.20 (1 H, s) 7.97 (1 H, s) 7.71 (2 H, dd, J=9.16, 4.58 Hz) 7.63 (2 H, s) 7.54 (2 H, d, J=7.12 Hz) 7.26-7.34 (4 H, m) 7.19 (1 H, t, J=7.38 Hz) 4.26 (1 H, s) 3.73-3.82 (4 H, m) 1.11 (6 H, d, J=3.05 Hz). LC/MS (m/z) 500.29 [(M+H)$^+$]; HPLC Rt: 3.871 min.

Biological Activity Data

The AP-1 activity of Examples 1 to 132 is given where the AP-1 EC$_{50}$ is less than 1 uM. Where the AP-1 EC50 is greater than 1 uM, the glucocorticoid receptor (GR) binding affinity (Ki) is given. The data presented below were obtained using the assays referred to in the table and described herein in the ASSAY section supra.

TABLE 8

| Ex. | GR (Ki, nM) (GR Binding Assay (I)) | GR (Ki, nM) (GR Binding Assay (II)) | AP-1 (EC50, nM) (Cellular Transrepression Assay) |
|---|---|---|---|
| 1 | | 8.3 | 1279 |
| 2 | | | 508 |
| 3 | | | 2520 |
| 4 | | | 1283 |
| 5 | | | 1060 |
| 6 | | 4.9 | 47 |
| 7 | | 6.1 | 139 |
| 8 | 17 | 9.0 | 48 |
| 9 | 8.3 | 5.6 | 29 |
| 10 | | 19 | 143 |
| 11 | | 16 | 29 |
| 12 | | | 211 |
| 13 | | 19 | 181 |
| 14 | | | 1858 |
| 15 | | | 2778 |
| (S)-16 | | | 2270 |
| (R)-16 | | 7.4 | 61 |
| (S)-17 | 0.63 | | 13 |
| (R)-17 | | 12 | 99 |
| 18 | 1.1 | | 25 |
| 19 | | 11 | >10000 |
| 20 | | | 573 |
| 21 | | 39 | 266 |
| 22 | | 17 | 679 |
| 23 | | 62 | 5961 |
| 24 | | 351 | >10000 |
| 25 | | 8.2 | >10000 |
| 26 | 3.1 | 8.6 | 965 |
| 27 | 4.6 | 6.4 | 219 |
| 28 | 4.2 | 4.9 | 21 |
| 29 | 2.5 | 8.0 | 86 |
| 30 | 8.5 | 27 | >10000 |
| 31 | 28 | 19 | 394 |
| 32 | 73 | 452 | >10000 |
| 33 | | 74 | >10000 |
| 34 | 1.1 | 7.1 | 129 |
| 35 | 2.3 | | 159 |
| 36 | 2.9 | | 135 |
| 37 | 5.8 | | >10000 |
| 38 | 6.3 | | >10000 |
| 39 | 3.2 | | >10000 |
| 40 | 11 | | >10000 |
| 41 | 8.1 | | >10000 |
| 42 | 2.4 | | 682 |
| 43 | 1.8 | | 171 |
| 44 | 2.7 | | 54 |
| 45 | 2.1 | | 1538 |
| 46 | 1.5 | | 6046 |
| 47 | 1.3 | | 204 |
| 48 | 3.1 | | 42 |
| 49 | 2.7 | | 78 |
| 50 | 7.5 | | 223 |
| 51 | 3.0 | | 624 |
| 52 | 2.3 | | 772 |
| 53 | 1.8 | | 306 |
| 54 | 22 | | 285 |
| 55 | 1.4 | | 698 |
| 56 | 6.1 | | 80 |
| 57A | | 59 | >10000 |
| 57B | | 15 | >10000 |
| 58A | | 14 | >10000 |
| 58B | | 8.8 | 106 |
| 59A | | 6.9 | 57 |
| 59B | | 9.3 | >10000 |
| 60 | 41 | 24 | 234 |
| 61 | | 9.6 | 371 |
| 62 | 11 | | >10000 |
| 63 | 4.3 | | >10000 |
| 64 | 17 | | >10000 |
| 65 | | 1.4 | 698 |
| 66 | 3.0 | | 177 |
| 67 | 5.6 | | 164 |
| 68 | 8.1 | | 271 |
| 69 diastA | 3.7 | | >10000 |
| 69 diastB | 3.4 | | >10000 |
| 70 | 44 | | >10000 |
| 71A | 5.8 | | 194 |
| 71B | 6.5 | | 511 |
| 72 | 55 | | |
| 73 | 13 | | 107 |
| 74 | 26 | | >10000 |
| 75 | 8.9 | | 628 |
| 76 | 8.7 | | >10000 |
| 77 | 7.4 | | 143 |
| 78 | 2.2 | | 813 |
| 79 | 11 | | 5000 |
| 80 | 3.0 | | 234 |
| 81 | 8.7 | | >5000 |
| (R)-82 | | 628 | >10000 |
| (S)-82 | | 39 | >10000 |
| (R)-83 | | 547 | >10000 |
| (S)-83 | | 34 | >10000 |
| 84 | | 115 | >10000 |
| 85 | | 2886 | >10000 |
| 86 | | 13 | >10000 |
| 87 | | 33 | >10000 |
| 88 | | 86 | >10000 |
| 89 | | 43 | >10000 |
| 90A | 2.3 | | 52 |
| 90B | 21 | | 176 |
| 90C | 2.4 | | 7.4 |
| 91A stereoisomerA | 2.1 | | 5.7 |
| 91B stereoisomerB | 15 | | 201 |
| 91C stereoisomerC | 2.8 | | 83 |
| 91D stereoisomerD | 74 | | 2500 |
| 92 | 0.94 | | 12 |

TABLE 8-continued

| Ex. | GR (Ki, nM) (GR Binding Assay (I)) | GR (Ki, nM) (GR Binding Assay (II)) | AP-1 (EC50, nM) (Cellular Transrepression Assay) |
|---|---|---|---|
| 93 | 0.92 | | 5.6 |
| 94 | 0.73 | | 12 |
| 95 | 1.2 | | 27 |
| 96 | 1.6 | | 58 |
| 97A stereoisomerA | 4.0 | | 71 |
| 97B stereoisomerB | 43 | | 136 |
| 97C stereoisomerC | 3.5 | | 158 |
| 98 | 3.7 | | 17 |
| 99 | 6.1 | | 40 |
| 100 | 18.3 | | 5000 |
| 101 | 2.1 | | 132 |
| 102 | 8.4 | | 691 |
| 103 | 5.9 | | 349 |
| 104 | 2.1 | | 23 |
| 105 | 1.7 | | 77 |
| 106 | 3.3 | | 304 |
| 107 | 3.1 | | 2017 |
| 108 | 1.7 | | 8.1 |
| 109 | | 9.2 | 43 |
| 110 | | 21 | >10000 |
| 111 | | 12 | 240 |
| 112 | | 11 | 95 |
| 113 | 22 | | |
| 114 | | 33 | >10000 |
| 115 | 16 | | >10000 |
| 116 | 177 | | >10000 |
| 117 | 20 | | >10000 |
| 118 | 29 | | 2798 |
| 119 | 53 | 26 | >10000 |
| 120 | | 21 | >10000 |
| 121 | | 69 | 3850 |
| 122 | 37 | 34 | >10000 |
| 123 | | 71 | >10000 |
| 124 | | 75 | >10000 |
| 125 | | 14 | >10000 |
| 126 | | 12 | >10000 |
| 127 | | 7.8 | 5872 |
| 128 | | 16 | >10000 |
| 129 | | 26 | 202 |
| 130 | | 252 | >10000 |
| 131 | | 20 | >10000 |
| 132 | | 28 | >10000 |

What is claimed is:

1. A compound according to formula I,

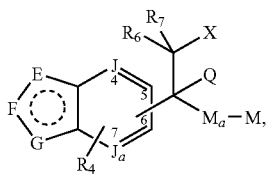

its enantiomers, diastereomers, tautomers, or a pharmaceutically-acceptable salt thereof, wherein the side chain group

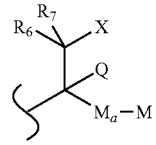

is attached to the bicyclic ring

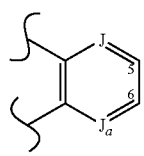

at the 5- or 6-position;

X is

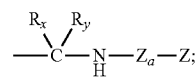

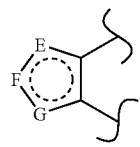

is heterocyclo or heteroaryl;
E is —$CR_2$—;
F is —N—;
G is —$NR_{1b}$—;
J is C;
$J_a$ is C;
M-$M_a$ is alkyl, haloalkyl, aryl, cycloalkyl, alkenyl, arylalkyl, heteroaryl, heterocyclo, alkylarylalkyl, alkylaryl, or haloaryl;
Q is selected from
 (i) hydrogen or $C_1$-$C_4$ alkyl;
 (ii) Q and $R_6$ are combined with the carbons to which they are attached to form a 3- to 6-membered cycloalkyl; or
 (iii) Q and -$M_a$-M are combined with the carbons to which they are attached to form a 3- to 7-membered ring containing 0, 1 or 2 heteroatoms which are the same or different and are independently selected from the group consisting of O, S, $SO_2$, and

which ring may be optionally substituted with 0-2 $R_3$ groups or carbonyl;
Z is selected from H, alkyl, cycloalkyl, heterocyclo, aryl, heteroaryl, —C(=O)C(=O)$R_{22}$, —C(=O)$NR_8R_9$, —C(=O)$R_8$, —C(NCN)$NR_8R_9$, —C(=O)$OR_8$, —$SO_2R_8$,

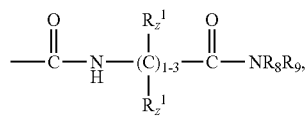

and —SO$_2$NR$_8$R$_9$;

Z$_a$ is a linker between N and Z and is selected from a bond; C$_1$-C$_5$ alkylene; C$_1$-C$_5$ alkylene which includes at any position in the chain a nitrogen which is substituted with alkyl, or an SO$_2$ group; —C(R$_z$$^1$)(R$_z$$^2$)C(=O)N(R$_z$$^3$)—; and —C(R$_z$$^1$)(R$_z$$^2$)S(=O)$_2$N(R$_z$$^3$)- (where R$_z$$^1$ and R$_z$$^2$ at each occurrence are independently selected from H, C$_1$-C$_4$ alkyl and halogen, and R$_z$$^3$ is H or C$_1$-C$_4$ alkyl);

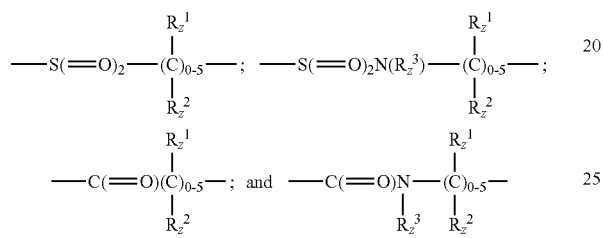

(wherein for each C in the chain

R$_z$$^1$ and R$_z$$^2$ are independently H, C$_1$-C$_4$ alkyl or halogen, and the right side of each Z$_a$ group is linked to Z);

R$_x$ and R$_y$ are the same or different and at each occurrence are independently selected from hydrogen, alkyl, alkenyl, alkynyl, cycloalkyl, cycloalkenyl, aryl, heteroaryl, and heterocyclo;

R$_{1b}$ is aryl;

R$_2$ is selected from hydrogen, halogen, alkyl, alkenyl, alkynyl, nitro, cyano, —OR$_{10}$, —NR$_{10}$R$_{11}$, —C(=O)R$_{10}$, —CO$_2$R$_{10}$, —C(=O)NR$_{10}$R$_{11}$, —O—C(=O)R$_{10}$, —NR$_{10}$C(=O)R$_{11}$, —NR$_{10}$C(=O)OR$_{11}$, —NR$_{10}$C(S)OR$_{11}$, —S(=O)$_p$R$_{12}$, —NR$_{10}$SO$_2$R$_{12}$, —SO$_2$NR$_{10}$R$_{11}$, cycloalkyl, cycloalkenyl, cycloalkynyl, heterocyclo, aryl, and heteroaryl;

R$_3$ at each occurrence is independently selected from hydrogen, halogen, alkyl, alkenyl, alkynyl, nitro, cyano, —OR$_{13}$, —NR$_{13}$R$_{14}$, —C(=O)R$_{13}$, —CO$_2$R$_{13}$, —C(=O)NR$_{13}$R$_{14}$, —O—C(=O)R$_{13}$, —NR$_{13}$C(=O)R$_{14}$, —NR$_{13}$C(=O)OR$_{14}$, —NR$_{13}$C(S)OR$_{14}$, —S(=O)$_p$R$_{15}$, —NR$_{13}$SO$_2$R$_{15}$, —SO$_2$NR$_{13}$R$_{14}$, cycloalkyl, cycloalkenyl, cycloalkynyl, heterocyclo, aryl, and heteroaryl;

R$_4$ is selected from hydrogen, alkyl, halogen, and C$_1$-C$_4$ alkoxy;

R$_6$ is selected from hydrogen or alkyl;

R$_7$ is selected from hydrogen, alkyl, alkenyl, cycloalkyl, aryl;

or R$_6$ and R$_7$ are taken together with the carbon to which they are attached to form a cycloalkyl group;

R$_5$, R$_8$, R$_9$, R$_{10}$, R$_{11}$, R$_{13}$, R$_{14}$, R$_{16}$, R$_{17}$, R$_{19}$ and R$_{20}$ are the same or different and at each occurrence are independently selected from
  (i) hydrogen, alkyl, alkenyl, alkynyl, cycloalkyl, cycloalkenyl, aryl, heteroaryl, carboxy, alkoxycarbonyl, and heterocyclo; or
  (ii) with respect to Z, R$_8$ is taken together with R$_9$; and/or with respect to R$_3$, R$_{13}$ is taken together with R$_{14}$; and/or with respect to R$_6$, R$_{16}$ is taken together with R$_{17}$; and/or with respect to R$_7$, R$_{19}$ is taken together with R$_{20}$, each of which forms a 4- to 6-membered heteroaryl, and heterocyclo ring;

R$_{12}$, R$_{15}$, R$_{18}$, and R$_{21}$ are the same or different and are independently selected from alkyl, alkenyl, alkynyl, cycloalkyl, cycloalkenyl, aryl, heteroaryl, and heterocyclo; and R$_{22}$ is selected from alkyl and alkoxy;

p is 0, 1 or 2;

provided that
1) R$_2$ cannot be NH$_2$; or
2) —Z$_a$—Z is other than H; or
3) when Q and R$_6$ are combined with the carbons to which they are attached to form a 3- to 6-membered cycloalkyl, —Z$_a$—Z cannot be alkyl; or
4) Z$_a$—Z cannot be a substituted or unsubstituted 4-piperidinyl group; or
5) R$_2$ is other than —C(=O)CH$_2$NO$_2$; or
6) when Q and M-M$_a$ (and the carbon to which they are attached) combine to form a 5- or 6-membered ring, then —Z$_a$—Z cannot be H or C$_1$-C$_5$ alkyl or —C(=O)C(=O)NH$_2$; or
7) when Q and R$_6$ (and the carbons to which they are attached) combine to form a substituted or unsubstituted 3- to 6-membered carbocyclic ring, neither Z$_a$ nor Z can be H or alkyl; or
8) where —Z$_a$—Z is alkyl, then
  a) at least one of Q, R$_6$, R$_7$, R$_x$ and R$_y$ is other than H or alkyl, or M$_a$-M is other than alkyl, or
  b) Q is other than H, or
  c) R$_6$ and R$_7$ are each other than H, or
  d) R$_x$ and R$_y$ are each other than H; or
9) where R$^2$ is H, then:
a) when -M$_a$-M is alkyl and —Z$_a$—Z is

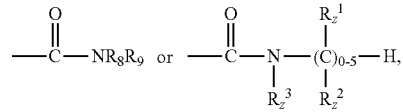

then —NR$_8$R$_9$ or

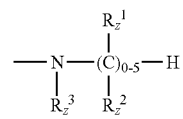

is other than

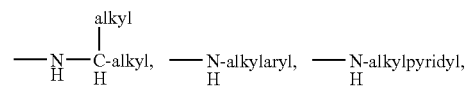

-continued

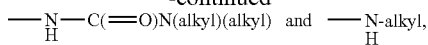

wherein the term "alkyl" by itself or as part of another group refers to unsubstituted straight chain or branched chain alkyl; or
b) when $-Z_a-Z$ is $-SO_2R_8$ or $-SO_2C(R_{z^1})(R_{z^2})H$, then $-M_a-M$ is other than $C_1-C_4$ alkyl or $-C(R_{m^1})(R_{m^2})C(=O)N(R_{m^3})H$; or
c) where Q is H or $C_1-C_5$ alkyl or $C_1-C_5$ haloalkyl and/or $M_a-M$ is $C_1-C_5$ alkyl or $C_1-C_5$ haloalkyl, and $R_6$ and $R_7$ are independently H, $C_1-C_5$ alkyl or $C_1-C_5$ haloalkyl, and $R_x$ and $R_y$ are independently H, $C_1-C_5$ alkyl or $C_1-C_5$ haloalkyl, and $Z_a-Z$ is $SO_2R_8$, then $R_8$ is other than aryl or heteroaryl; or
d) when $-M_a-M$ is alkyl, aryl, heteroaryl, arylalkyl or heteroarylalkyl, then $-Z_a-Z$ cannot be unsubstituted straight chain alkyl or unsubstituted branched chain alkyl, $-SO_2-$ alkyl where alkyl is unsubstituted straight chain alkyl or unsubstituted branched chain alkyl, $-SO_2H$, $-SO_2N(alkyl)(alkyl)$ where both alkyls are independently unsubstituted straight chain alkyl or unsubstituted branched chain alkyl, $-SO_2NH-$ alkyl where alkyl is unsubstituted straight chain alkyl or unsubstituted branched chain alkyl, $-C(=O)$ alkyl where alkyl is unsubstituted straight chain alkyl or unsubstituted branched chain alkyl, $-SO_2NH_2$, $-C(=O)N(alkyl)(alkyl)$ where both alkyls are independently unsubstituted straight chain alkyl or unsubstituted branched chain alkyl, $-C(=O)NH$ alkyl where alkyl is unsubstituted straight chain alkyl or unsubstituted branched chain alkyl or $-C(=O)NH_2$; or
e) when $-M_a-M$ is aryl or alkyl, then where $-Z_a-Z$ is $-SO_2$-alkyl or $-C(=O)$ alkyl, then the alkyl portion of the $-Z_a-Z$ group is substituted straight chain alkyl or substituted branched chain alkyl where the substituent is other than alkyl.

2. The compound as defined in claim 1 wherein the ring system

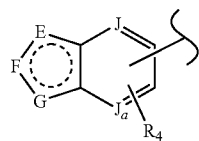

is

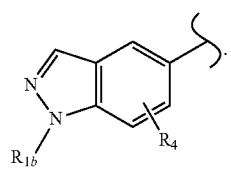

3. The compound as defined in claim 1 wherein
$R_x$ is H, unsubstituted alkyl or haloalkyl;
$R_y$ is H, unsubstituted alkyl or haloalkyl;
$M-M_a-$ is unsubstituted alkyl, haloalkyl, aryl, cycloalkyl, alkenyl, arylalkyl, or heteroaryl;
Q is H or $C_1-C_4$ alkyl; or Q and $M-M_a$ and the carbons to which they are attached can combine to form a -3- to 7-membered ring containing 1 or 2 heteroatoms, or a $C_3-C_7$ cycloalkyl, or
Q and R6 and the carbons to which they are attached can combine to form a $C_3-C_6$ cycloalkyl ring;
$Z_a$ is a bond or $C_1-C_4$ alkyl; and
Z is H, amino, alkyl, unsubstituted alkylcarbonyl, haloalkylcarbonyl, heteroarylcarbonyl, aminocarbonyl, alkoxycarbonylcarbonyl, carboxycarbonyl, heteroaryl, substituted heteroaryl, cycloalkyl, hydroxycycloalkyl, aminocycloalkyl, alkylcarbonylaminocycloalkyl, haloalkylsulfonyl, alkylaminocarbonyl, cyanoalkylcarbonyl, arylcarbonyl, alkylsulfonyl, alkoxyalkylcarbonyl, dialkylaminoalkylcarbonyl, alkylsulfonylalkylcarbonyl, arylalkylcarbonyl, heteroarylalkylcarbonyl, heteroarylcarbonyl, heterocyclocarbonyl, cycloalkylcarbonyl, heterocycloalkylcarbonyl (or cycloheteroalkylalkylcarbonyl), alkylcarbonylaminoalkylcarbonyl, alkoxyarylalkylcarbonyl, alkylsulfonyl, arylsulfonyl, arylalkylsulfonyl, arylaminocarbonyl, alkoxycarbonyl, carboxyalkylcarbonyl, alkylcarbonylalkylcarbonyl, aminosulfonylalkylcarbonyl, hydroxyalkylcarbonyl, haloalkylcycloalkylcarbonyl, haloalkylalkylcarbonyl, cycloalkylsulfonyl, alkylsulfonylalkylsulfonyl, haloalkylarylsulfonyl, dialkylaminosulfonyl, heterocycloaminocarbonyl, alkynylaminocarbonyl, diarylalkylaminocarbonyl, alkylthioalkyl(alkoxycarbonyl)aminocarbonyl, alkylcycloalkylaminocarbonyl, arylalkylaminocarbonyl, (hydroxylaryl)(alkoxyalkyl)aminocarbonyl, alkyl(hydroxyalkyl)(aminocarbonyl)aminocarbonyl, hydroxyheterocycloaminocarbonyl, arylalkylheterocycloaminocarbonyl, (haloarylalkyl)(hydroxyalkyl)aminocarbonyl, haloalkylalkylaminocarbonyl, cycloalkylaminocarbonyl, haloalkylalkoxycarbonyl, hydroxyalkylaminocarbonyl, alkyl(alkyl)aminocarbonyl (where alkyls are the same or different), heterocycloalkylaminocarbonyl,

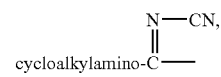

hydroxyalkylheterocyclocarbonyl, aminoheterocyclocarbonyl, aminoalkylamino, alkoxycarbonylalkylaminocarbonyl, hydroxyalkylcycloalkylaminocarbonyl, alkylaminosulfonyl, alkylheterocyclo, dihydroxyalkyl(alkyl)aminocarbonyl, (hydroxyl)alkyl, carboxyalkylaminocarbonyl, cyanoheterocycloaminocarbonyl, heterocyclocarbonylalkylaminocarbonyl, haloarylalkylaminocarbonyl, dialkylaminocarbonyl, alkylcarbonylcarbonyl, arylaminocarbonylalkylaminocarbonyl, haloarylalkylcarbonyl, alkyl(hydroxyl)alkylcarbonyl, alkenylheterocycloaminocarbonyl, or hydroxyalkyl(alkyl)aminoalkylaminocarbonyl.

4. The compound as defined in claim 1 wherein
$R_{1b}$ is substituted aryl which is haloalkylaryl, haloaryl, haloalkylalkyl(halo)aryl, alkoxyaryl, hydroxyaryl, alkoxycarbonylaryl, carboxyaryl, or alkoxycarbonylaryl;
Z is selected from unsubstituted heteroaryl, alkoxycarbonylheteroaryl, alkylheteroaryl, cycloalkyl, aminoheteroaryl, cyanoheteroaryl, cycloalkylheteroaryl, hydroxyheteroaryl, alkylthioheteroaryl, dialkylheteroaryl, haloalkylheteroaryl, haloheteroaryl, hydroxycycloalkyl, aminocycloalkyl, alkylcarbonylaminocycloalkyl, alkylsulfonyl, haloalkylsulfonyl, alkyl, and haloalkylcarbonyl; or Z is substituted heteroaryl which is substituted with one, two or three groups which are the same or different and are independently selected from hydrogen, halogen, alkyl, substituted alkyl, alkenyl, substituted alkenyl, alkynyl, substituted alkynyl, nitro, cyano, $OR_1^c$, $NR_1^a R_1^b$, $C(=O)R_1^c$, $CO_2R_1^c$, $C(=O)NR_1^a R_1^b$, $-O-C(=O)R_1^c$, $NR_1^a C(=O)R_1^b$, $NR_1^a C(=O)OR_1^b$, $NR_1^a C(=S)OR_1^b$, $S(O)_{p_1}R_1^c$, $NR_1^a SO_2 R_1^b$, $SO_2 NR_1^a R_1^b$, cycloalkyl, cycloalkenyl, heterocyclo, aryl, and heteroaryl;

$R_1^a$, $R_1^b$, and $R_1^c$, are the same or different and are independently selected from (i) hydrogen, alkyl, substituted alkyl, alkenyl, substituted alkenyl, alkynyl, substituted alkynyl, cycloalkyl, cycloalkenyl, aryl, heteroaryl, and heterocyclo; or (ii) where possible $R_1^a$ is taken together with $R_1^b$ to form a heteroaryl or heterocyclo ring;

$p_1$ is 0, 1 or 2;

$Z_a$ is a bond, $C_1$-$O_5$ alkylene;

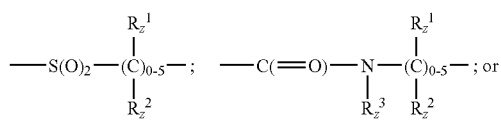

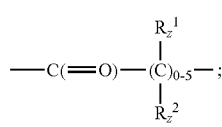

M-$M_a$ is alkyl, aryl, cycloalkyl, heteroaryl, arylalkyl, heterocyclo, alkylarylalkyl, alkylaryl, or haloaryl;

Q is H or $C_1$-$C_4$ alkyl, or

Q and R6 and the carbons to which they are attached can be combined to form

Q and M-$M_a$ and the carbons to which they are attached can be combined to form

5. A compound as defined in claim 1, wherein

E is CH, $R_{1b}$ is

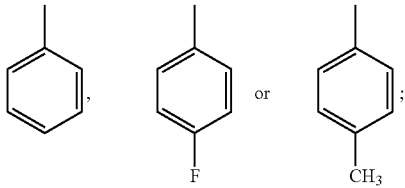

$R_6$ is H or $CH_3$;

$R_7$ is H, $CH_3$, $C_2H_5$, $C_3H_7$, $C_6H_5$, Δ, i-$C_3H_7$, or $-CH_2-CH=CH_2$;

or $R_6$ and $R_7$ together form

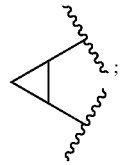

$R_4$ is H;

$R_x$ is H, $CH_3$ or $CF_3$;

$R_y$ is H, $CH_3$ or $CF_3$;

M-$M_a$ is

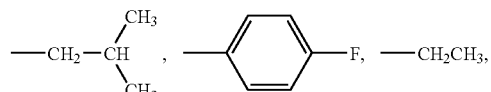

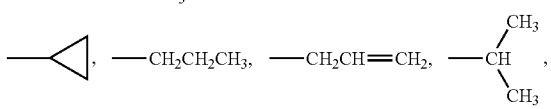

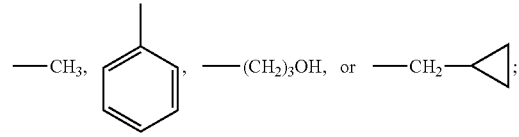

and Q is H or $CH_3$;

or Q and M-$M_a$ and the carbons to which they are attached are taken together to form

-$Z_a$-Z is 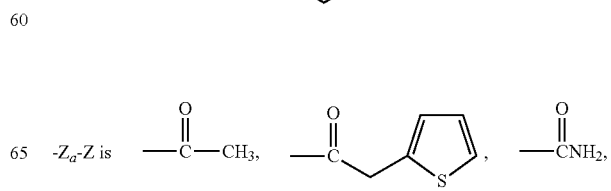

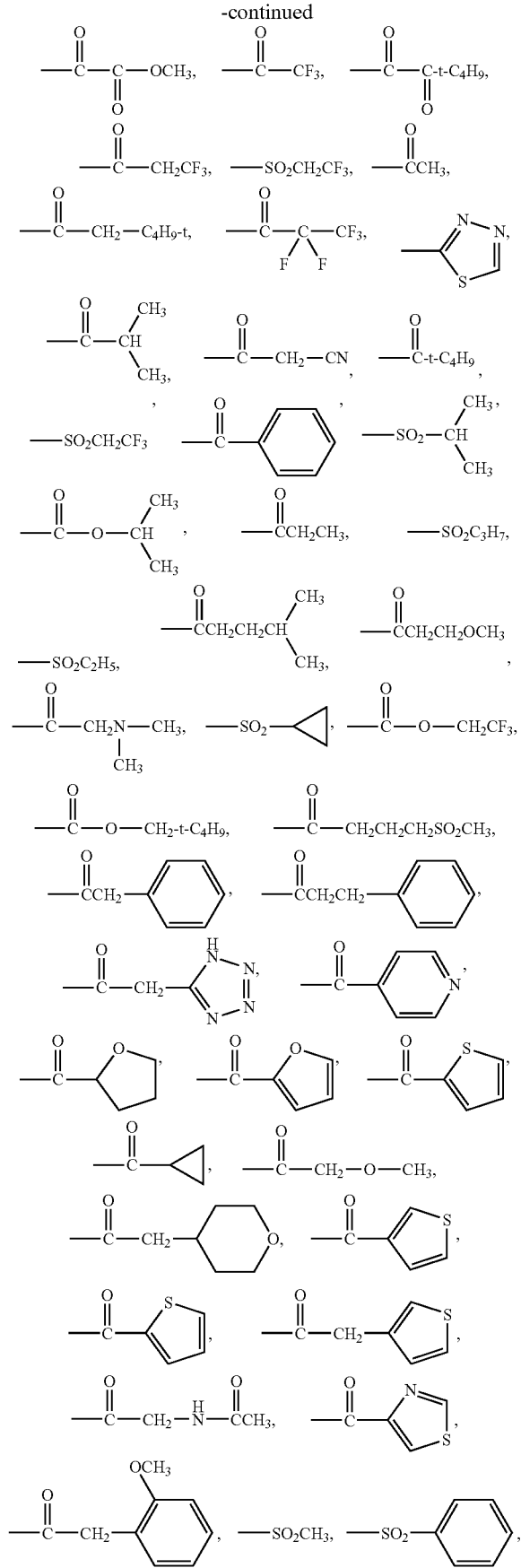
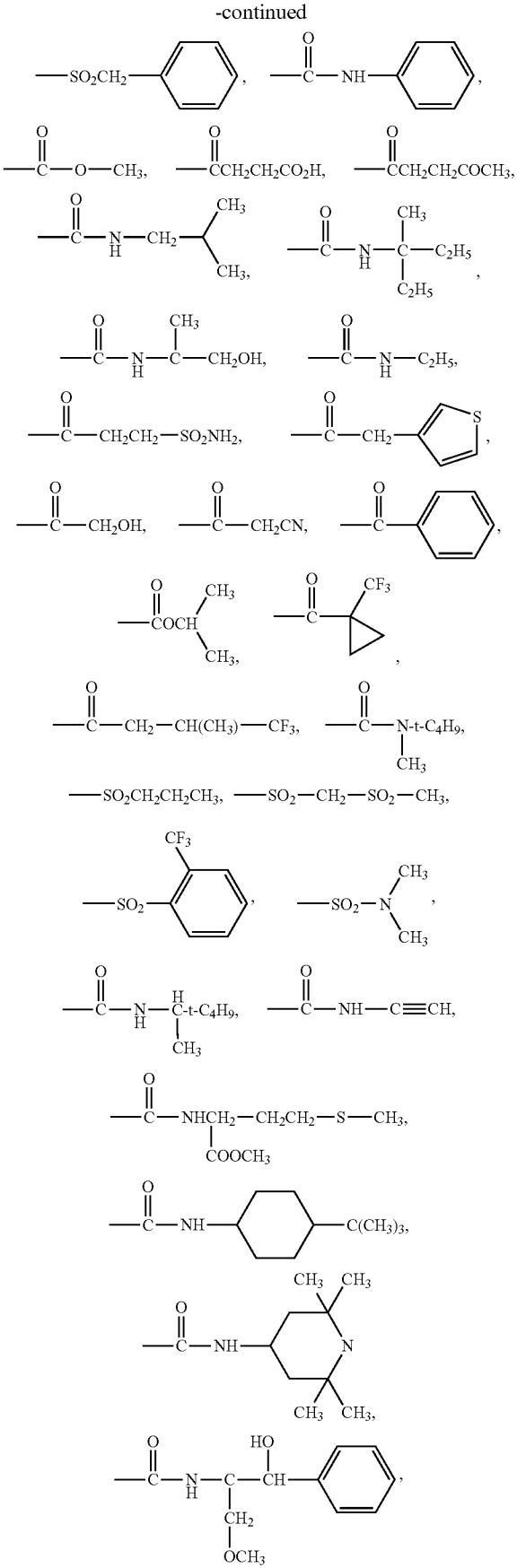

-continued
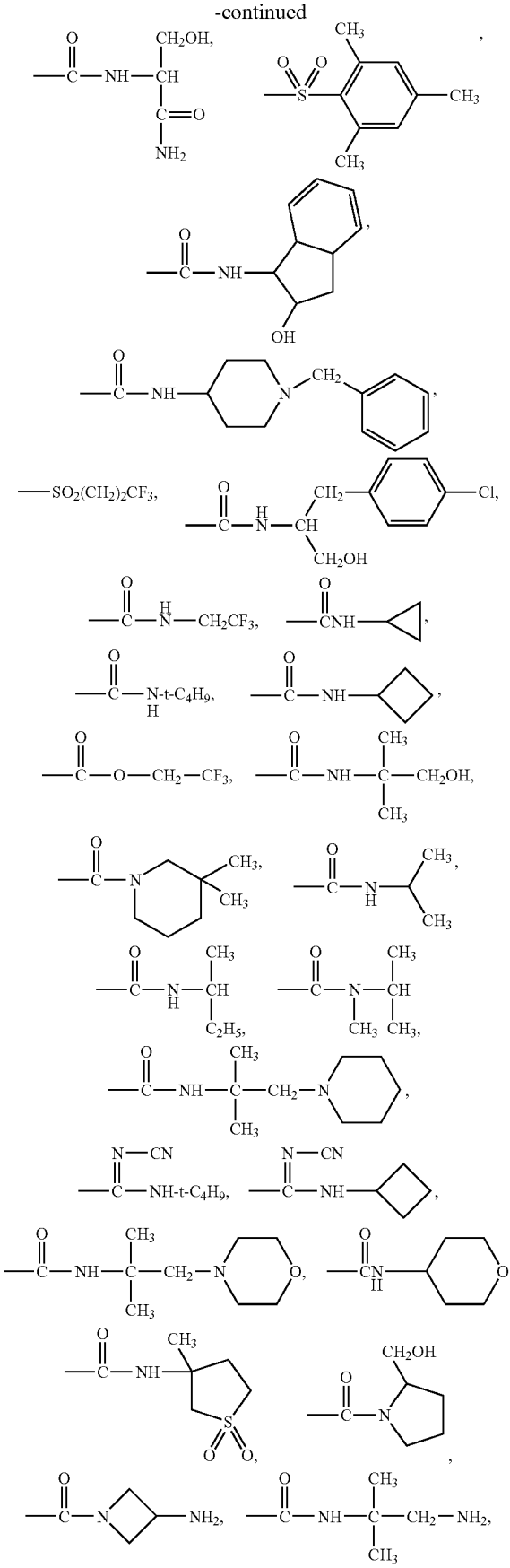
-continued
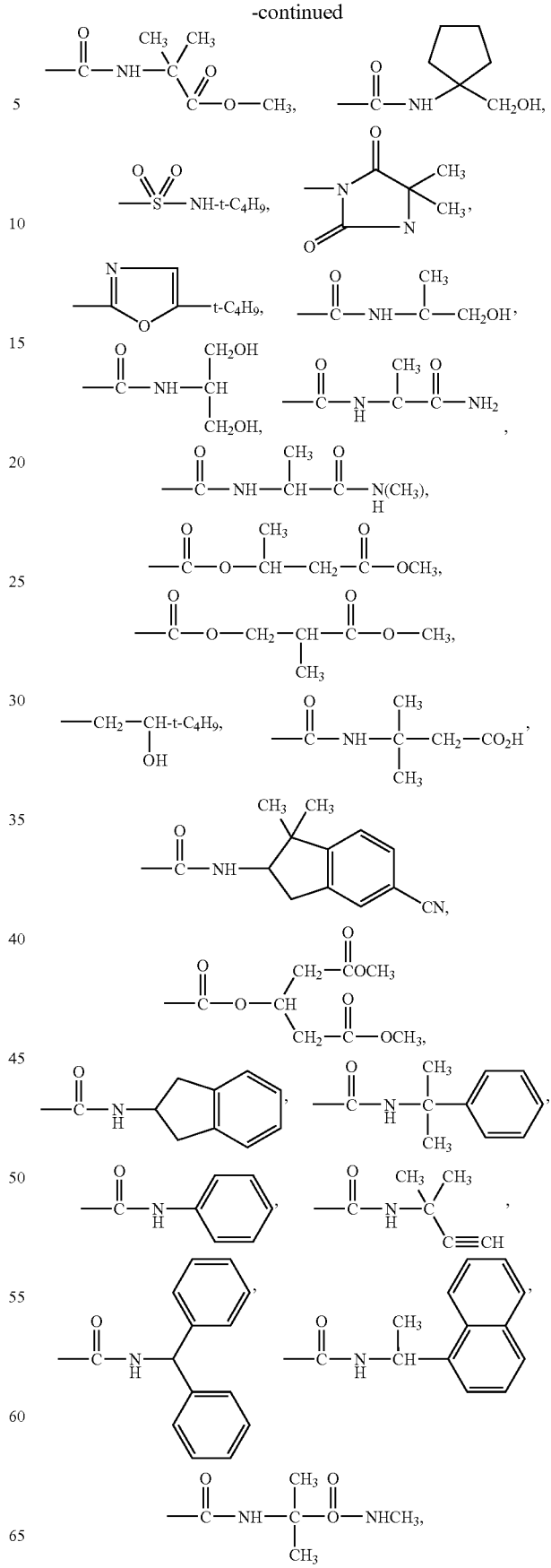

217
-continued
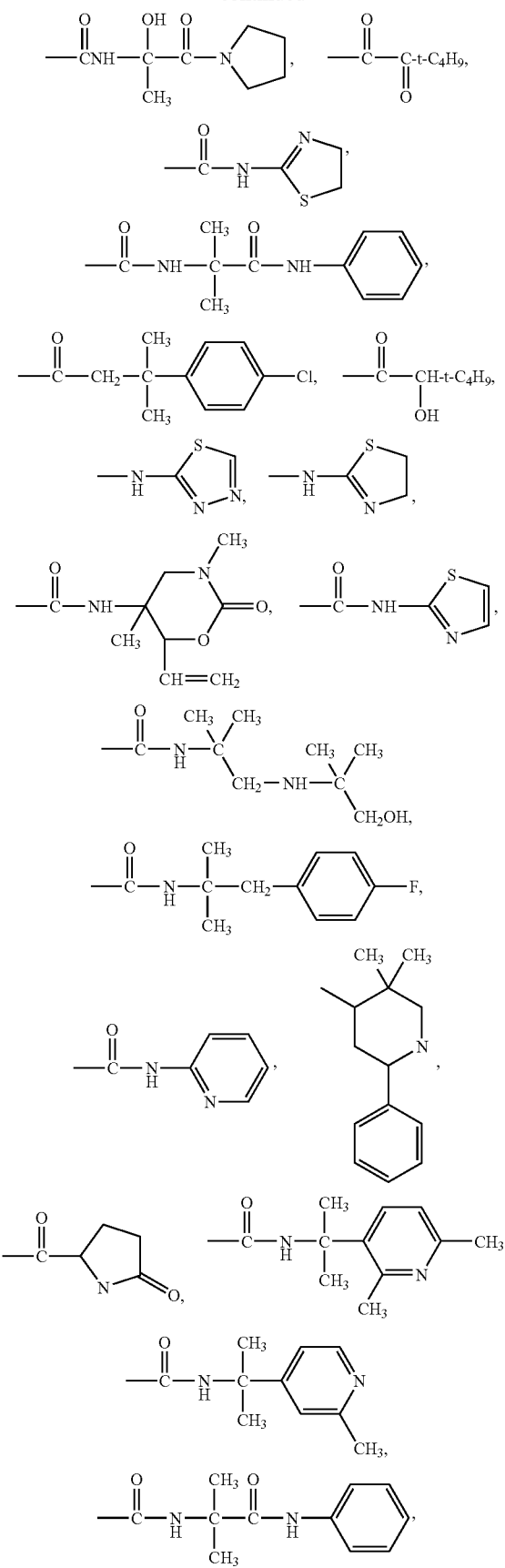
218
-continued
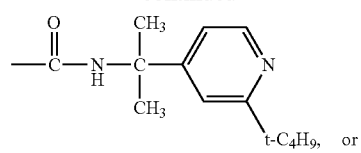
or a pharmaceutically acceptable salt thereof.
6. The compound as defined in claim 1 having the structure
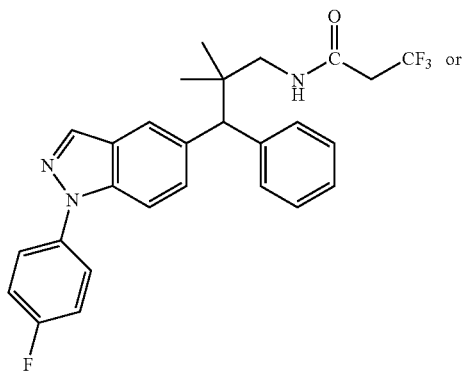
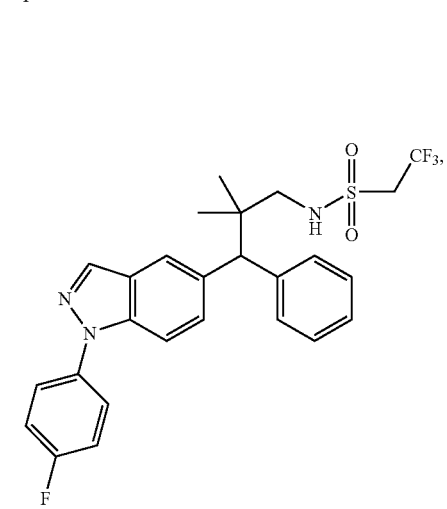
or a pharmaceutically acceptable salt thereof.
7. A compound having the structure
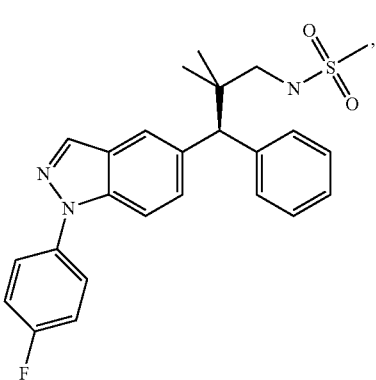

219
-continued
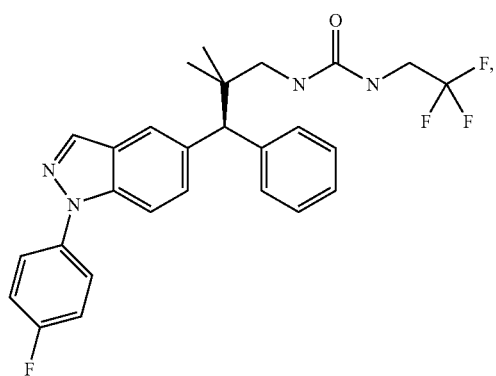
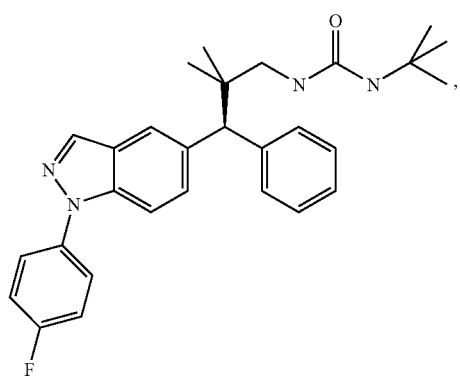
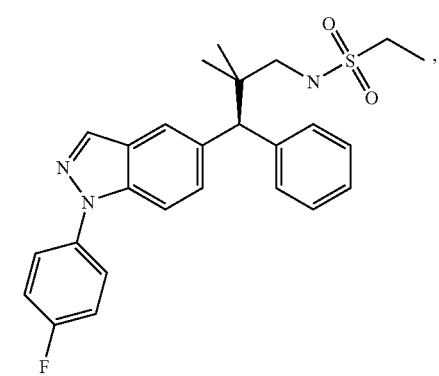
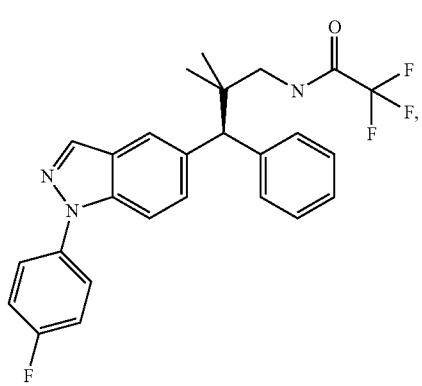
220
-continued
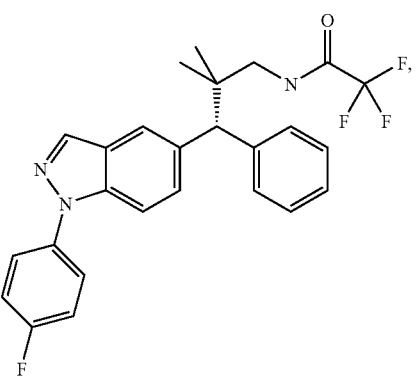
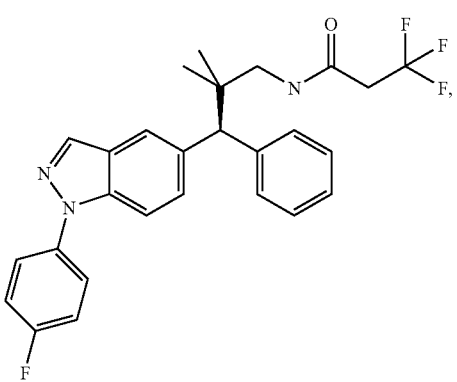
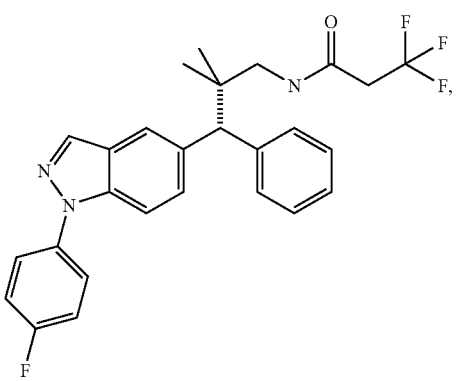
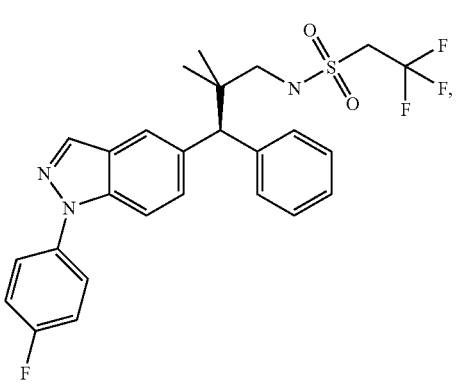

221
-continued
222
-continued
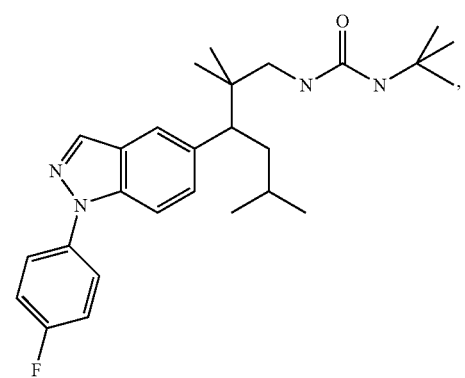
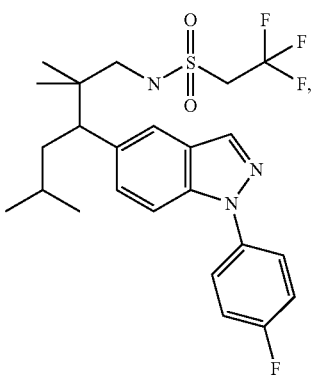

223
-continued
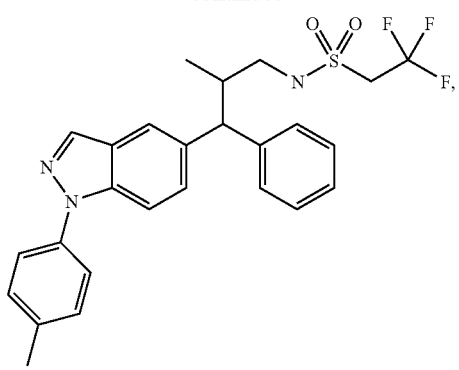
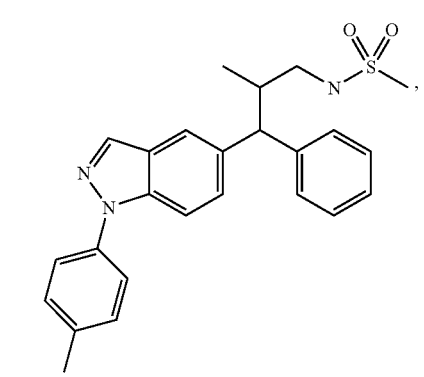
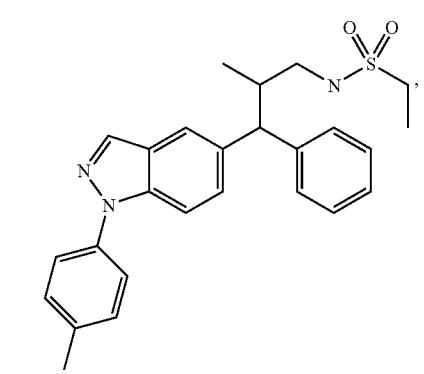
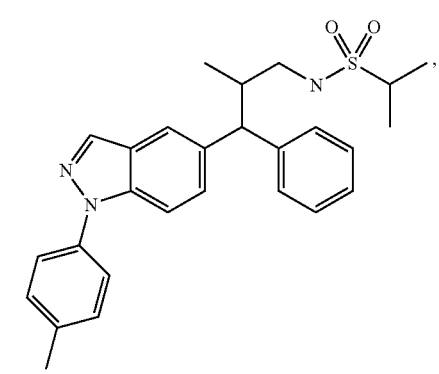
224
-continued
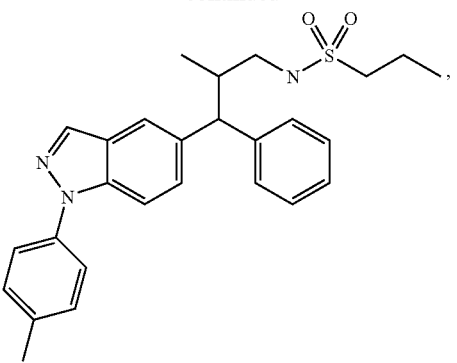
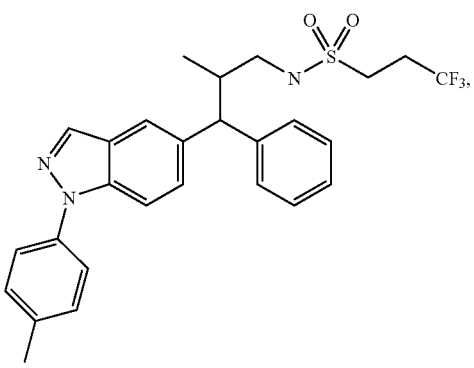
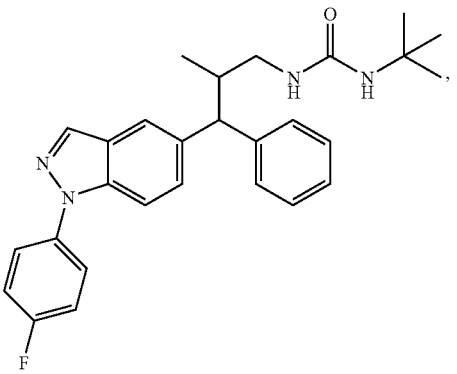
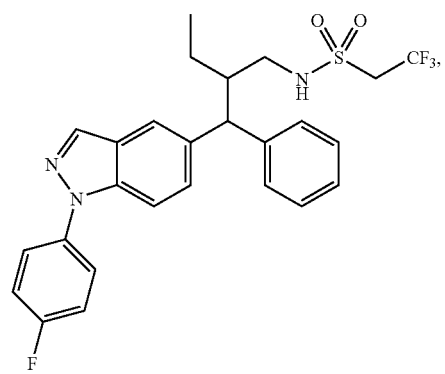

-continued

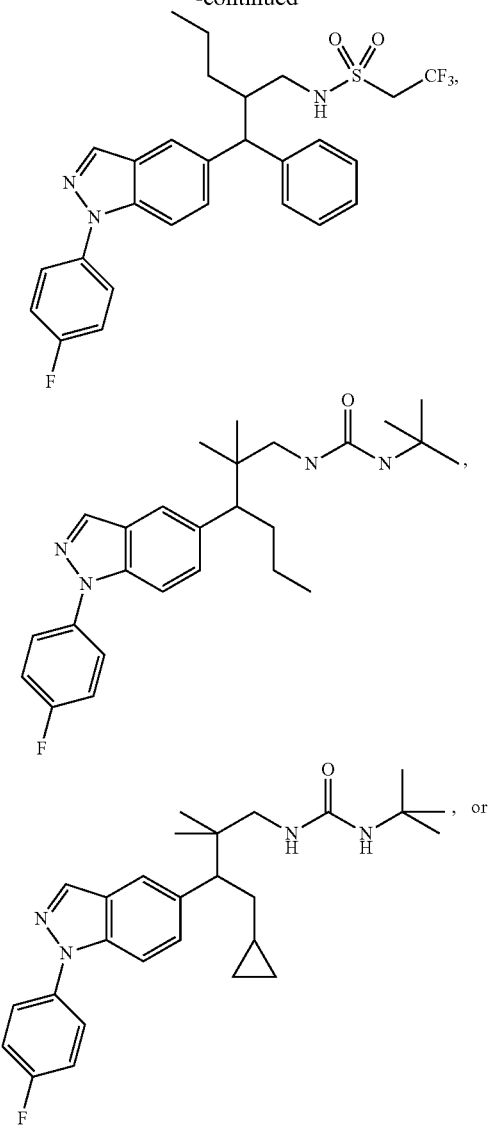

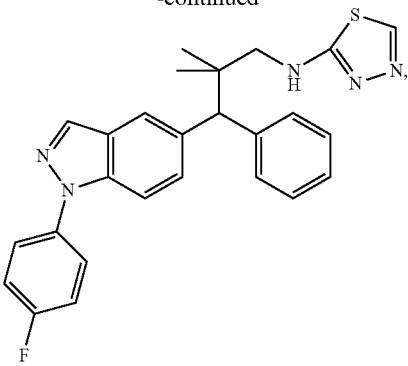

or a pharmaceutically acceptable salt thereof.

8. A pharmaceutical composition comprising a compound as defined in claim 1 and a pharmaceutically acceptable carrier therefor.

9. A pharmaceutical combination comprising a compound as defined in claim 1 and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid-lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, and wherein the antihypertensive agent is an ACE inhibitor, angiotensin II receptor antagonist, NEP/ACE inhibitor, calcium channel blocker and/or β-adrenergic blocker.

* * * * *

UNITED STATES PATENT AND TRADEMARK OFFICE
CERTIFICATE OF CORRECTION

PATENT NO. : 8,198,311 B2
APPLICATION NO. : 12/513232
DATED : June 12, 2012
INVENTOR(S) : James E. Sheppeck et al.

It is certified that error appears in the above-identified patent and that said Letters Patent is hereby corrected as shown below:

Claim 1:
Column 207, line 13, after "($R_z^3$)—", delete "and".
Column 208, line 42, change "where" to -- when --.

Claim 3:
Column 210, line 4, change "R6" to -- $R_6$ --.

Claim 4:
Column 211, line 23, change "$C_1$-$0_5$" to -- $C_1$-$C_5$ --.
Column 211, line 43, change "R6" to -- $R_6$ --.

Claim 7:
Column 222, lines 59 to 66, delete

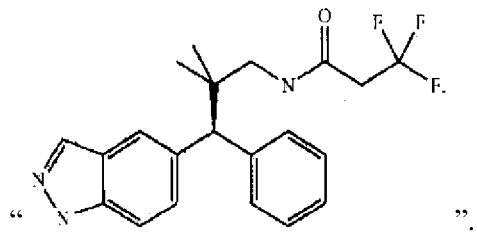

" ".

Signed and Sealed this
Ninth Day of October, 2012

David J. Kappos
*Director of the United States Patent and Trademark Office*